US012559673B2

(12) United States Patent
Ogawa et al.

(10) Patent No.: US 12,559,673 B2
(45) Date of Patent: Feb. 24, 2026

(54) ORGANIC ELECTROLUMINESCENT ELEMENT

(71) Applicant: NIPPON STEEL Chemical & Material Co., Ltd., Tokyo (JP)

(72) Inventors: Junya Ogawa, Tokyo (JP); Takahiro Kai, Tokyo (JP); Masashi Tada, Tokyo (JP); Kazunari Yoshida, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 1022 days.

(21) Appl. No.: 17/641,882

(22) PCT Filed: Sep. 16, 2020

(86) PCT No.: PCT/JP2020/034993

§ 371 (c)(1),
(2) Date: Mar. 10, 2022

(87) PCT Pub. No.: WO2021/065492

PCT Pub. Date: Apr. 8, 2021

(65) Prior Publication Data

US 2022/0348557 A1 Nov. 3, 2022

(30) Foreign Application Priority Data

Sep. 30, 2019 (JP) ................................ 2019-180499

(51) Int. Cl.

| | |
|---|---|
| ***C09K 11/06*** | (2006.01) |
| ***C07D 401/14*** | (2006.01) |
| ***C07D 405/14*** | (2006.01) |
| ***C07D 409/14*** | (2006.01) |
| ***C07D 487/04*** | (2006.01) |
| ***C07F 15/00*** | (2006.01) |
| ***H10K 50/11*** | (2023.01) |
| ***H10K 50/18*** | (2023.01) |
| ***H10K 71/16*** | (2023.01) |
| ***H10K 85/30*** | (2023.01) |
| ***H10K 85/60*** | (2023.01) |
| ***H10K 101/00*** | (2023.01) |

(52) U.S. Cl.

CPC ............ *C09K 11/06* (2013.01); *C07D 401/14* (2013.01); *C07D 405/14* (2013.01); *C07D 409/14* (2013.01); *C07D 487/04* (2013.01); *H10K 50/11* (2023.02); *H10K 85/615* (2023.02); *H10K 85/622* (2023.02); *H10K 85/631* (2023.02); *H10K 85/652* (2023.02); *H10K 85/654* (2023.02); *H10K 85/6572* (2023.02); *H10K 85/6574* (2023.02); *H10K 85/6576* (2023.02); *C07F 15/0033* (2013.01); *H10K 50/18* (2023.02); *H10K 71/164* (2023.02); *H10K 85/342* (2023.02); *H10K 2101/90* (2023.02)

(58) Field of Classification Search

CPC .. H10K 50/11; H10K 2101/90; H10K 85/615; H10K 85/622; H10K 85/631; H10K 85/652; H10K 85/654; H10K 85/6572; H10K 85/6574; H10K 85/6576; C07D 403/14; C07D 401/14; C07D 405/14; C07D 409/14; C07D 487/04; C07D 209/86; C09K 11/06; C09K 2211/1007; C09K 2211/1029; C09K 2211/1044; C09K 2211/1059

See application file for complete search history.

(56) References Cited

U.S. PATENT DOCUMENTS

| | | | | |
|---|---|---|---|---|
| 2002/0121860 | A1* | 9/2002 | Seo ........................ | H10K 50/11 313/506 |
| 2006/0103298 | A1* | 5/2006 | Lee ........................ | H10K 50/11 313/506 |
| 2007/0252516 | A1* | 11/2007 | Kondakova ............ | H10K 50/11 428/917 |
| 2009/0021146 | A1 | 1/2009 | Iida et al. | |
| 2010/0295444 | A1 | 11/2010 | Kuma et al. | |
| 2012/0235136 | A1 | 9/2012 | Ogawa et al. | |
| 2012/0241732 | A1 | 9/2012 | Endo et al. | |

(Continued)

FOREIGN PATENT DOCUMENTS

| | | | |
|---|---|---|---|
| CN | 102503937 | A | 6/2012 |
| JP | 2003133075 | A * | 5/2003 |

(Continued)

OTHER PUBLICATIONS

Ikenaga et al., machine translation WO-2016158363-A1 (2016) pp. 1-32. (Year: 2016).*

(Continued)

*Primary Examiner* — Dylan C Kershner

(74) *Attorney, Agent, or Firm* — Birch, Stewart, Kolasch & Birch, LLP

(57) ABSTRACT

To provide an organic electroluminescent device having high efficiency and high driving stability while having a low driving voltage. The organic electroluminescent device has one or more light-emitting layers between an anode and a cathode opposed to each other, wherein at least one of the light-emitting layers is a light-emitting layer composed of a vapor deposition layer containing a first host, a second host and a light-emitting dopant material; the first host is selected from oligopyridine compounds represented by the general formula (1); and the second host is selected from carbazole compounds having two or more carbazole rings, indolocarbazole compounds having an indolocarbazole ring or compounds having a carbazole ring and an indolocarbazole ring.

10 Claims, 1 Drawing Sheet

(56) References Cited

U.S. PATENT DOCUMENTS

| | | | | |
|---|---|---|---|---|
| 2014/0077172 | A1* | 3/2014 | So | H10K 50/11 438/46 |
| 2014/0306207 | A1 | 10/2014 | Nishimura et al. | |
| 2014/0374728 | A1 | 12/2014 | Adamovich et al. | |
| 2015/0021577 | A1 | 1/2015 | Kadoma et al. | |
| 2018/0083201 | A1 | 3/2018 | Ogawa et al. | |
| 2018/0138420 | A1 | 5/2018 | Tada et al. | |
| 2018/0254426 | A1 | 9/2018 | Ikenaga et al. | |

FOREIGN PATENT DOCUMENTS

| | | | | | |
|---|---|---|---|---|---|
| JP | 2006-232813 | A | | 9/2006 | |
| JP | 2010215759 | A | * | 9/2010 | |
| KR | 10-2012-0109585 | A | | 10/2012 | |
| KR | 10-2014-0028640 | A | | 3/2014 | |
| KR | 10-2015-0010603 | A | | 1/2015 | |
| WO | WO 2010/134350 | A1 | | 11/2010 | |
| WO | WO 2011/070963 | A1 | | 6/2011 | |
| WO | WO 2011/136755 | A1 | | 11/2011 | |
| WO | WO 2013/062075 | A1 | | 5/2013 | |
| WO | WO 2016/158191 | A1 | | 10/2016 | |
| WO | WO-2016158363 | A1 | * | 10/2016 | C09K 11/06 |
| WO | WO 2016/194604 | A1 | | 12/2016 | |

OTHER PUBLICATIONS

Tominaga et al., machine translation JP-2003133075-A (2003) pp. 1-9. (Year: 2003).*

Nishizeki et al., machine translation JP-2010215759-A (2010) pp. 1-178. (Year: 2010).*

* cited by examiner

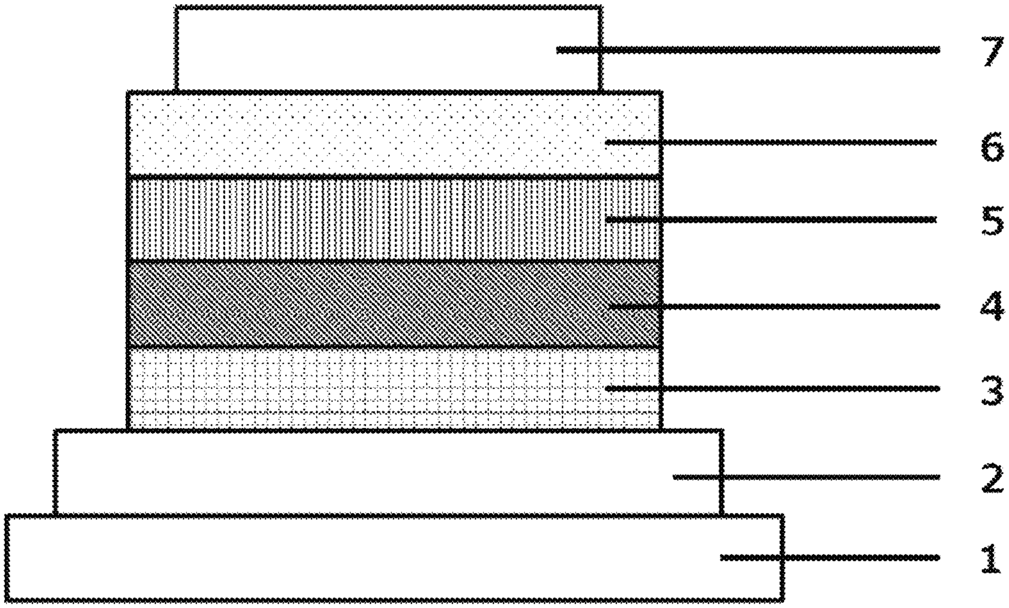
7
6
5
4
3
2
1

ORGANIC ELECTROLUMINESCENT ELEMENT

TECHNICAL FIELD

The present invention relates to an organic electroluminescent device (organic EL device). More specifically, the present invention relates to an organic electroluminescent device using a material for organic electroluminescent device composed of an oligopyridine compound.

BACKGROUND ART

Application of a voltage to an organic electroluminescent device allows injection of holes and electrons from an anode and a cathode, respectively, into a light-emitting layer. Then, in the light-emitting layer, injected holes and electrons recombine to generate excitons. At this time, according to statistical rules of electron spins, singlet excitons and triplet excitons are generated at a ratio of 1:3. Regarding a fluorescence-emitting organic electroluminescent device using light emission from singlet excitons, it is said that the internal quantum efficiency thereof has a limit of 25%. Meanwhile, regarding a phosphorescent organic electroluminescent device using light emission from triplet excitons, it is known that intersystem crossing is efficiently performed from singlet excitons, the internal quantum efficiency is enhanced to 100%.

However, extending the life of a phosphorescent organic electroluminescent device has been a technical challenge.

Recently, highly efficient organic electroluminescent devices utilizing delayed fluorescence have been developed. For example, Patent Literature 1 discloses an organic electroluminescent device utilizing a TTF (Triplet-Triplet Fusion) mechanism, which is one of delayed fluorescence mechanisms. The TTF mechanism utilizes a phenomenon in which singlet excitons are generated due to collision of two triplet excitons, and it is thought that the internal quantum efficiency can be theoretically raised to 40%. However, since the efficiency is lower compared to phosphorescent organic electroluminescent devices, further improvement in efficiency is required.

Patent Literature 2 discloses an organic electroluminescent device utilizing a TADF (Thermally Activated Delayed Fluorescence) mechanism. The TADF mechanism utilizes a phenomenon in which reverse intersystem crossing from triplet excitons to singlet excitons is generated in a material having a small energy difference between a singlet level and a triplet level, and it is thought that the internal quantum efficiency can be theoretically raised to 100%. However, further improvement in lifespan characteristics is required as in the case of phosphorescent devices.

CITATION LIST

Patent Literature

Patent Literature 1: WO2010/134350A
Patent Literature 2: WO2011/070963A
Patent Literature 3: WO2013/062075A
Patent Literature 4: US2014/0374728A
Patent Literature 5: WO2011/136755A
Patent Literature 6: WO2011/070963A
Patent Literature 7: JP2006-232813A
Patent Literature 8: KR2014-0028640A
Patent Literature 9: CN102503937A Patent Literatures 3 and 4 disclose use of a biscarbazole compound as a mixed host.

Patent Literature 5 discloses use of a host material in which a plurality of hosts containing an indolocarbazole compound is premixed.

Patent Literature 6 discloses to use an indolocarbazole compound as a thermally activated delayed fluorescence-emitting dopant material.

Patent Literature 7 discloses use of a bipyridine compound as a host material.

Patent Literature 8 discloses use of a terpyridine compound.

Patent Literature 9 discloses use of a quaterpyridine compound as a host material.

However, none of these can be said to be sufficient, and further improvement is desired.

SUMMARY OF INVENTION

In order to apply organic electroluminescent devices to display devices such as flat panel displays, or light sources, it is necessary to improve the luminous efficiency of devices and at the same time, to sufficiently secure the stability during driving. An object of the present invention is to provide an organic electroluminescent device having high efficiency and high driving stability while having a low driving voltage, and a material for organic electroluminescent device suitable therefor.

As a result of intensive studies, the present inventors have found that use of a specific oligopyridine compound as a first host provides an organic electroluminescent device exhibiting excellent characteristics, and have completed the present invention.

The present invention is an organic electroluminescent device comprising one or more light-emitting layers between an anode a cathode opposed to each other, wherein at least one of the light-emitting layers contains a first host selected from a compound represented by the following general formula (1) and a second host selected from a compound represented by the following general formula (2), general formula (3), general formula (4) or general formula (5).

[C1]

(1)

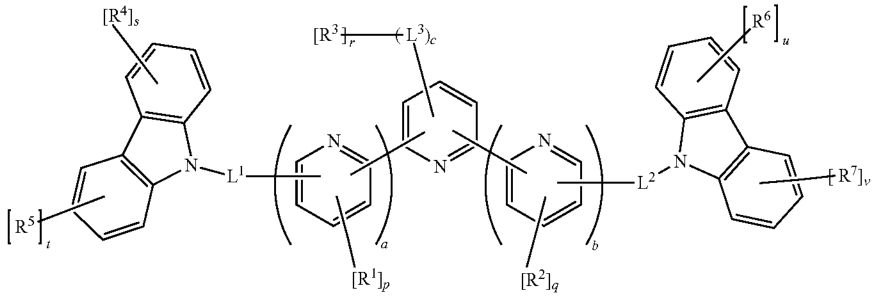

In the formula, $L^1$ to $L^3$ each represent a single bond, a substituted or unsubstituted aromatic hydrocarbon group having 6 to 30 carbon atoms, or a linked aromatic group in which 2 to 10 thereof are linked to each other, $R^1$ to $R^7$ independently represent hydrogen, deuterium, an aliphatic hydrocarbon group having 1 to 10 carbon atoms, a substituted or unsubstituted aromatic hydrocarbon group having 6 to 10 carbon atoms or an aromatic heterocyclic group having 3 to 12 carbon atoms. a, b and c represent the number of repetitions, wherein $a+b \geq 1$, and each independently represent an integer of 0 to 3. p, q, r, s, t, u and v represent the number of substitutions and each independently represent an integer of 1 to 3.

[C2]

(2)

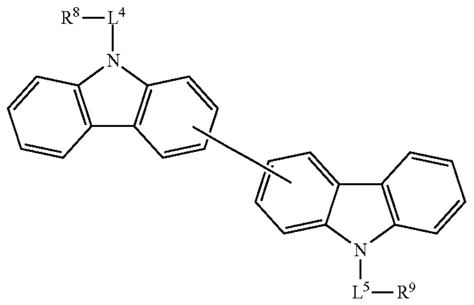

In the formula, $R^8$ and $R^9$ independently represent hydrogen, an aromatic hydrocarbon group having 6 to 14 carbon atoms, or a group in which two of the aromatic hydrocarbon groups are linked to each other. $L^4$ and $L^5$ independently represent a phenylene group.

[C3]

(3)

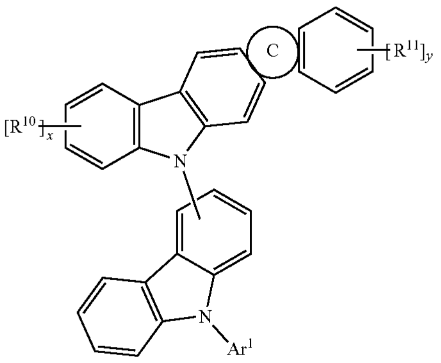

(3a)

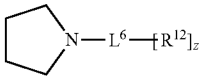

In the formula, a ring C is a heterocycle represented by formula (3a) and the ring C is fused to an adjacent ring at any position; $R^{10}$ to $R^{12}$ independently represent hydrogen, deuterium, an aliphatic hydrocarbon group having 1 to 10 carbon atoms, an aromatic hydrocarbon group having 6 to 10 carbon atoms, or an aromatic heterocyclic group having 3 to 12 carbon atoms; $L^6$ represents a single bond, an aromatic hydrocarbon group having 6 to 10 carbon atoms, an aromatic heterocyclic group having 3 to 12 carbon atoms, or a linked aromatic group in which 2 to 10 thereof are linked to each other; and $Ar^1$ represents an aromatic hydrocarbon group having 6 to 10 carbon atoms or an aromatic heterocyclic group having 3 to 12 carbon atoms. x, y and z each independently represent an integer of 0 to 3.

[C4]

(4)

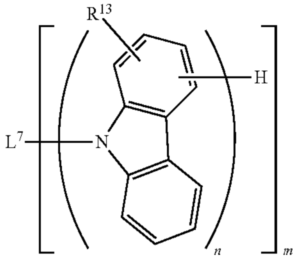

In the formula, $L^7$ is an m-valent aromatic hydrocarbon group having 6 to 30 carbon atoms, an aromatic heterocyclic group having 3 to 16 carbon atoms, or a linked aromatic group in which 2 to 10 of the aromatic rings are linked to each other, provided that $L^7$ is not a group containing a carbazole ring. $R^{13}$ is each independently hydrogen, an alkyl group having 1 to 10 carbon atoms, or a cycloalkyl group having 3 to 11 carbon atoms. m is the number of substitutions and represents an integer of 1 to 3. n is the number of repetitions and is each independently an integer of 1 to 4, provided that at least one n is an integer of 2 to 4.

[C5]

(5)

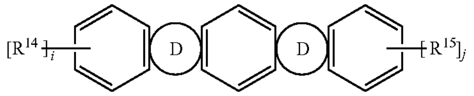

(5a)

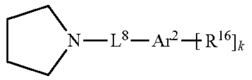

In the formula, a ring D is a heterocycle represented by formula (5a) and the ring D is fused to an adjacent ring at any position; $R^{14}$ to $R^{16}$ are independently hydrogen, deuterium, an aliphatic hydrocarbon group having 1 to 10 carbon atoms, an aromatic hydrocarbon group having 6 to 30 carbon atoms, or an aromatic heterocyclic group having 3 to 12 carbon atoms; $L^8$ is a single bond, an aromatic hydrocarbon group having 6 to 10 carbon atoms, or a linked aromatic group in which 2 to 10 thereof are linked to each other; and Are is an aromatic hydrocarbon group having 6 to 30 carbon atoms. i, j and k each independently represent an integer of 0 to 3.

Preferred aspects of the above general formula (1), (2), (3), (4) or (5) are shown below:

The general formula (2) is the following formula (6):

[C6]

(6)

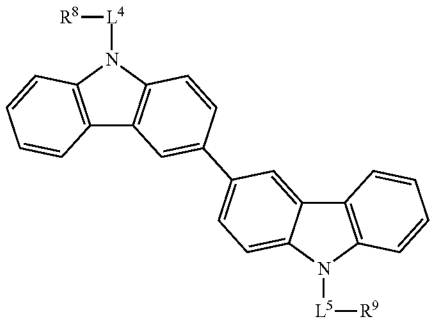

wherein $R^8$, $R^9$, $L^4$ and $L^5$ are as defined for the general formula (2).

The general formula (3) is the following formula (7) or (8):

[C7]

(7)

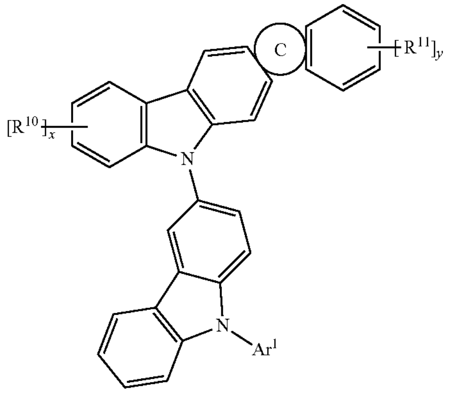

-continued (8)

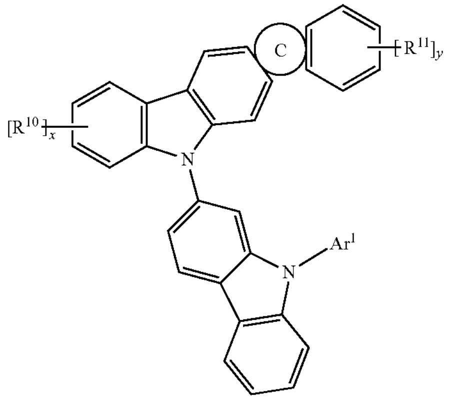

wherein a ring C, $R^{10}$, $R^{11}$, $Ar^1$, x and y are as defined for the general formula (3).

The general formula (4) has at least one binding structure represented by formula (c1) or formula (c2):

[C8]

(c1)

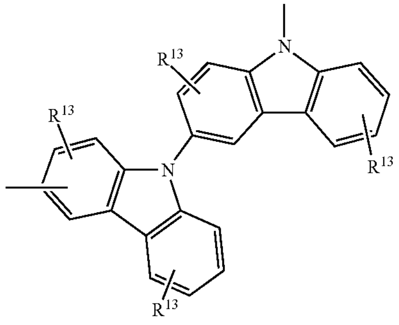

(c2)

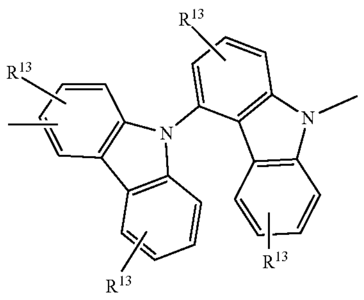

wherein $R^{13}$ is as defined for the general formula (4).

The general formula (1) is any one of the following formulas (9) to (11):

[C9]

(9)

(10)

(11)

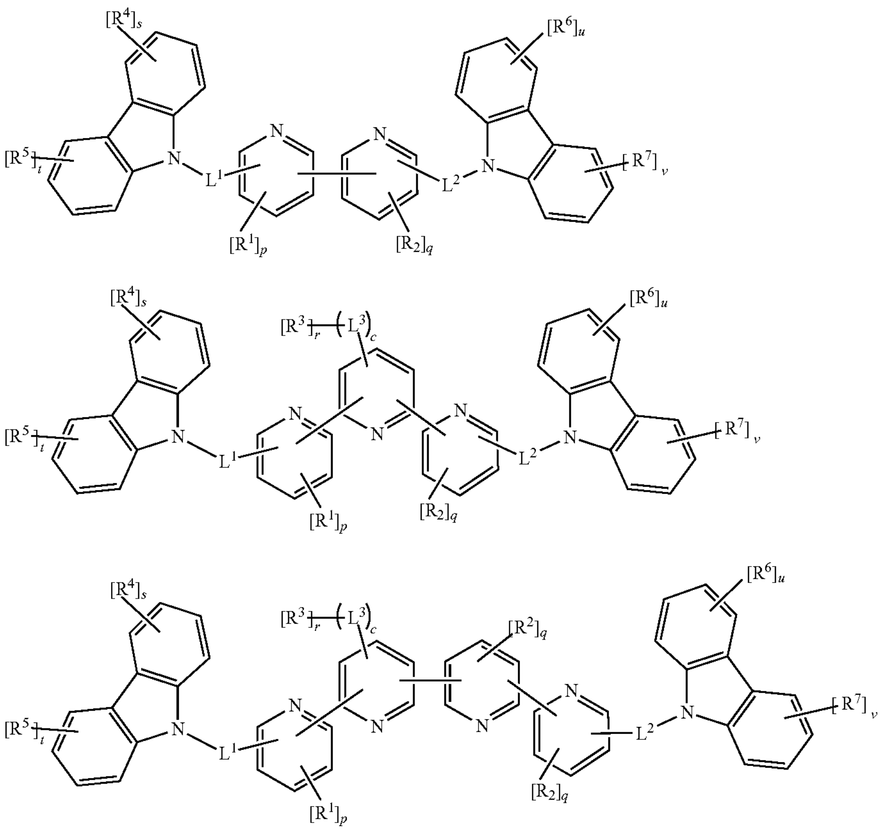

wherein $L^1$ to $L^3$, $R^1$ to $R^7$ and c and p to v are as defined for the general formula (1).

Preferred aspects of the organic electroluminescent device are shown below:

- The proportion of the first host is larger than 20 wt % and less than 55 wt % based on the first host and the second host in total;
- The light-emitting dopant material is an organic metal complex containing at least one metal selected from the group consisting of ruthenium, rhodium, palladium, silver, rhenium, osmium, iridium, platinum and gold, or a thermally activated delayed fluorescence-emitting dopant material;
- A hole blocking layer is provided adjacent to the light-emitting layer, and a compound represented by the general formula (1) is contained in the hole blocking layer.

In addition, the present invention is a method for producing the above organic electroluminescent device, including a step of mixing a first host and a second host to prepare a premixture, and then vapor-depositing a host material containing the premixture to form a light-emitting layer.

In the above method for producing the organic electroluminescent device, it is suitable that a difference in 50% weight reduction temperatures of the first host and the second host is within 20° C.

For improvement of device characteristics, a higher durability of a material used for an organic layer against charges is needed, and particularly, in the light-emitting layer, it is important to reduce leakage of excitons and charges to surrounding layers. For leakage reduction of charges/excitons, it is effective to improve deviation of a light emission area in the light-emitting layer. For this purpose, it is necessary to control amounts of both charges (electrons/holes) injected into the light-emitting layer or amounts of both charges transported in the light-emitting layer within a preferred range.

An oligopyridine compound represented by formula (1) used in the present invention has a structure in which a plurality of pyridine rings are bonded and two or more carbazole rings are bonded thereto. The both charges-injection transport ability of a material used for an organic layer significantly depends on the magnitude of the energy level of molecular orbital of the material and the intermolecular interaction. The oligopyridine compound especially has a high electron injection transport ability, but introduction of a carbazole ring thereinto causes a steric hindrance effect to thereby enable the proximity of oligopyridine sites to be suppressed. Then, changing a kind of substituent or a binding position of a pyridine ring group allows a high-level control of the intermolecular interaction of molecular orbital, which makes a large contribution to electron injection transport to a light-emitting layer.

Meanwhile, a carbazole compound represented by the general formulas (2) to (5) especially has a high hole injection transport ability, and changing the binding form of a carbazole ring or the kind or number of substituents to a skeleton thereof allows a high-level control of hole injection transport properties. Then, mixing the above oligopyridine compound and carbazole compound and using the mixture can control amounts of both charges injected into an organic layer within a preferred range, so that more favorable device characteristics can be expected. In particular, in the case of a delayed fluorescence-emitting EL device or a phosphorescent EL device, they have a lowest excited triplet energy sufficiently high to confine the excitation energy generated in the light-emitting layer and therefore, they have no outflow of energy from the inside of the light-emitting layer and they can achieve high efficiency and extended life at a low voltage.

BRIEF DESCRIPTION OF DRAWING

The sole drawing FIGURE is a schematic cross-sectional view showing one example of an organic electroluminescent device.

DESCRIPTION OF EMBODIMENTS

An organic electroluminescent device of the present invention has a structure wherein an anode, an organic layer and a cathode laminated on a substrate, wherein at least one layer of the organic layer contains a material for the above organic electroluminescent device.

This organic electroluminescent device has an organic layer composed of a plurality of layers between the anode and the cathode opposed to each other; and at least one layer of the plurality of layers is a light-emitting layer, and there may be a plurality of light-emitting layers. Then, at least one of the light-emitting layers is a light-emitting layer composed of a vapor deposition layer containing a first host, a second host and a light-emitting dopant material.

An organic electroluminescent device is characterized in that the first host contained in the light-emitting layer is selected from the compounds represented by the general formula (1), and the second host is selected from the compounds represented by the general formula (2), general formula (3), general formula (4) or general formula (5).

The first host is selected from oligopyridine compounds represented by the general formula (1).

In the general formula (1), $R^1$ to $R^7$ independently represent hydrogen, deuterium, an aliphatic hydrocarbon group having 1 to 10 carbon atoms, an aromatic hydrocarbon group having 6 to 30 carbon atoms, or an aromatic heterocyclic group having 3 to 12 carbon atoms; preferably, an aliphatic hydrocarbon group having 1 to 8 carbon atoms, a phenyl group or an aromatic heterocyclic group having 3 to 12 carbon atoms; and more preferably an aliphatic hydrocarbon group having 1 to 6 carbon atoms, a phenyl group or a carbazole ring group.

In the present specification, it is understood that an aromatic hydrocarbon group, an aromatic heterocyclic group and a linked aromatic group generated by linking of these aromatic rings with a single bond may have a substituent unless they are not specified as being unsubstituted. The same applies to an aliphatic hydrocarbon group.

Specific examples of the aliphatic hydrocarbon group include methyl, ethyl, propyl, butyl, pentyl, hexyl, heptyl, octyl, nonyl, and decyl. An alkyl group having 1 to 4 carbon atoms is preferred.

Specific examples of the aromatic hydrocarbon groups and the aromatic heterocyclic groups include aromatic groups generated by removing one H from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, dibenzofuran, dibenzothiophene, dibenzoselenophene, and carbazole. Preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, and benzothiadiazole. More preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, and oxadiazole.

$L^1$ to $L^3$ independently represent a single bond, a substituted or unsubstituted aromatic hydrocarbon group having 6 to 10 carbon atoms, or a linked aromatic group in which 2 to 10 thereof are linked to each other. Preferred examples of the aromatic hydrocarbon group include divalent groups generated from benzene and naphthalene. Preferred examples of the linked aromatic group include divalent groups generated from biphenyl and terphenyl.

a, b and c represent the number of repetitions, and each independently represent an integer of 0 to 3, preferably an integer of 0 or 1, provided that $a+b \geq 1$.

p to v represent the number of substitutions, and each independently represent an integer of 1 to 3, preferably an integer of 1 or 2.

Preferred aspects of the compounds represented by the general formula (1) include compounds represented by any of the general formulas (9) to (11). In the general formulas (9) to (11), the same symbols as in the general formula (1) have the same meaning.

Specific examples of the compounds represented by the general formula (1) are described below, but the compounds are not limited to these exemplified compounds.

[C10]
1-1
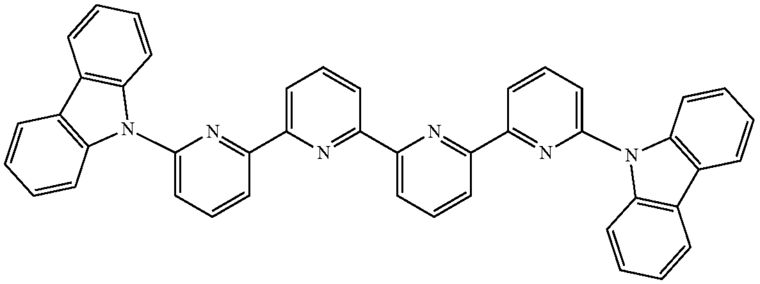
1-2
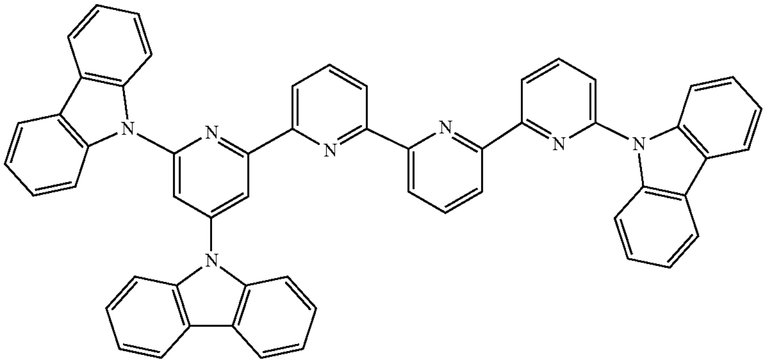
1-3
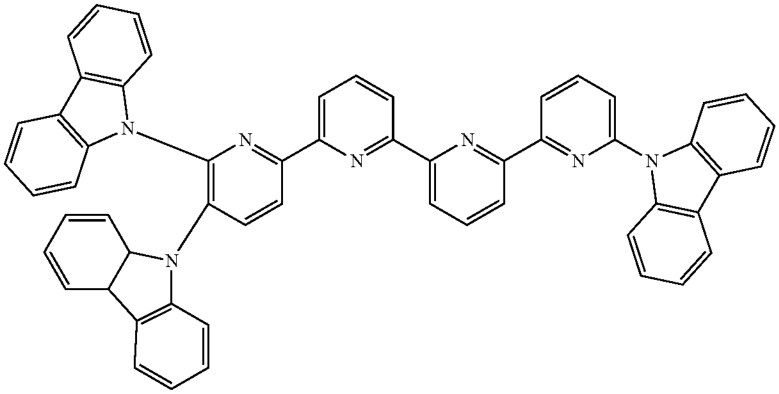
1-4
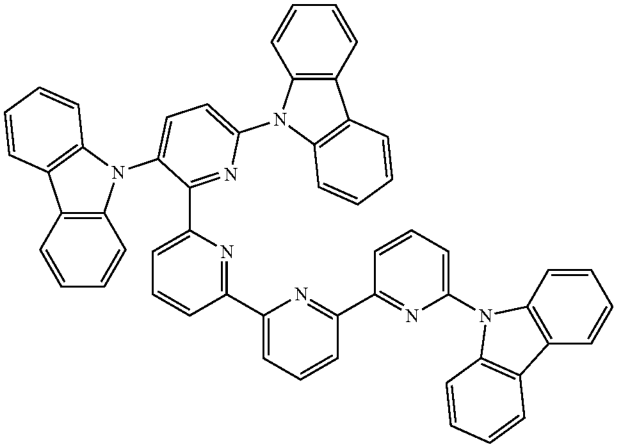

-continued
1-5
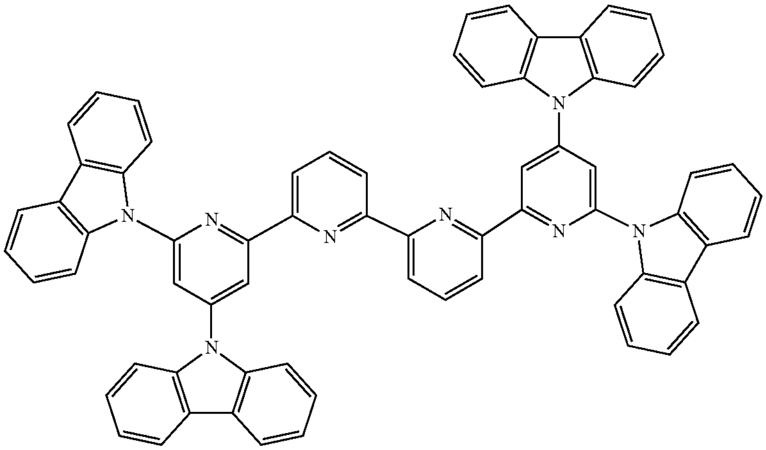
1-6
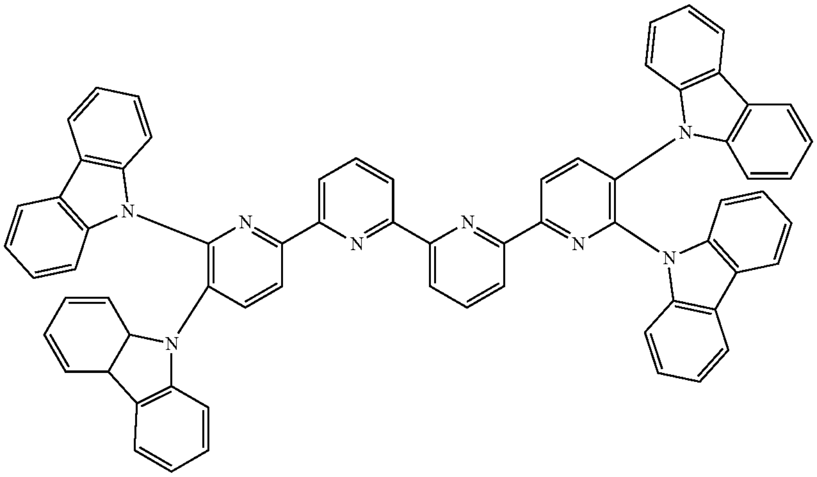
1-7
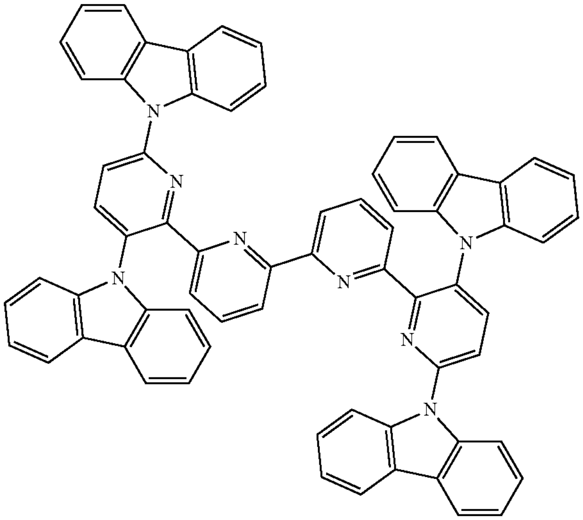

-continued
1-8
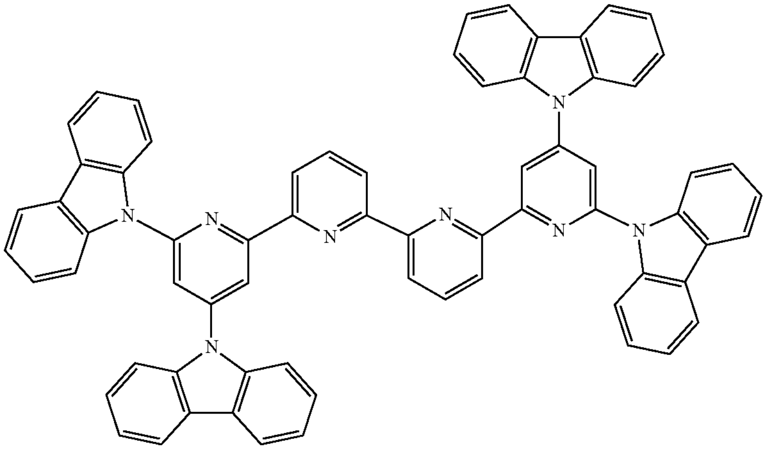
1-9
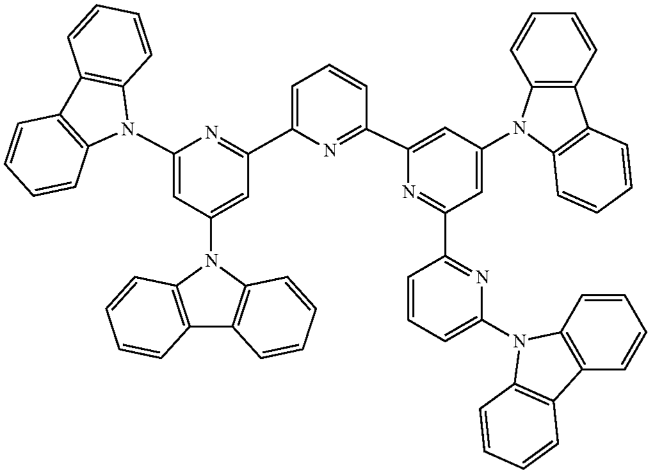
1-10
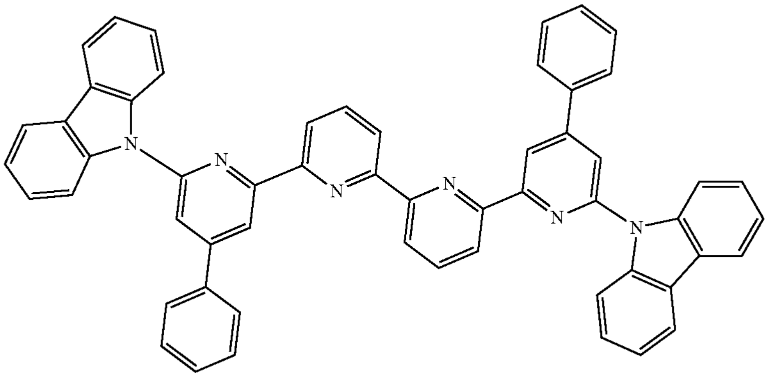

-continued
1-11
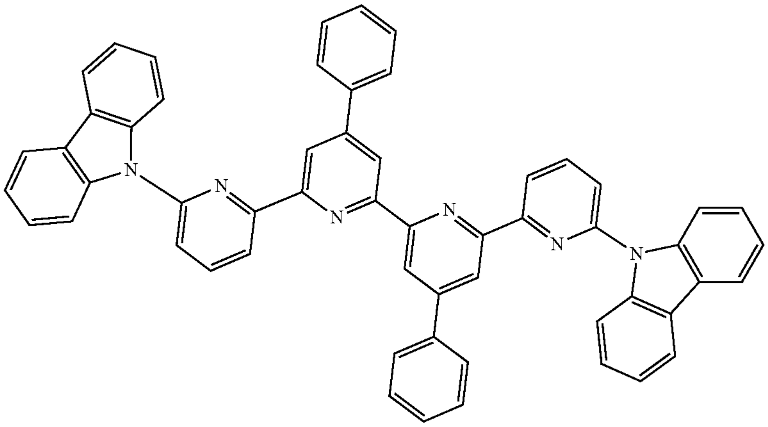
1-12
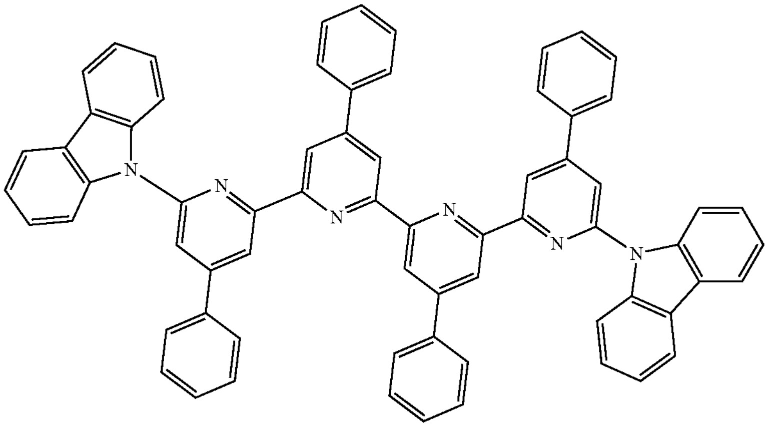
1-13
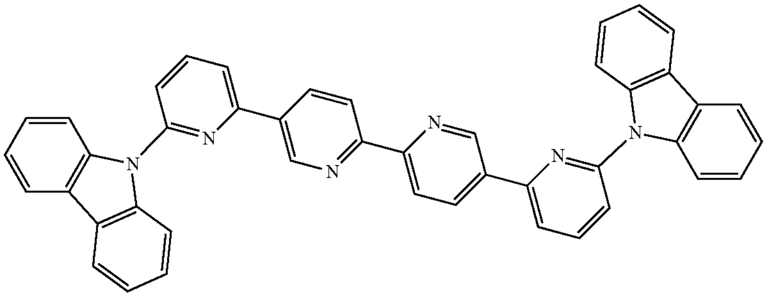
1-14
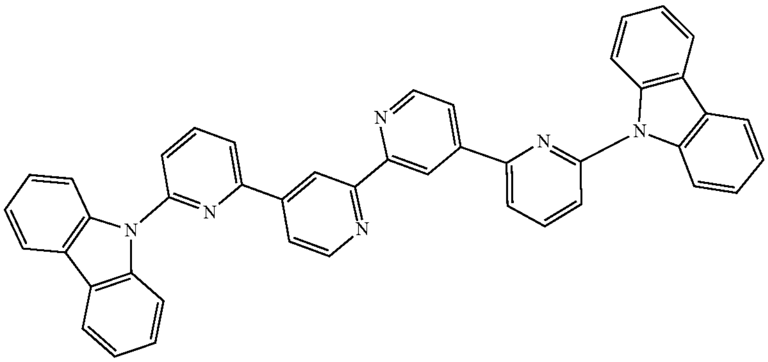

-continued
1-15
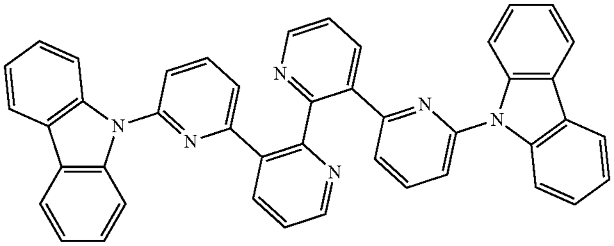
1-16
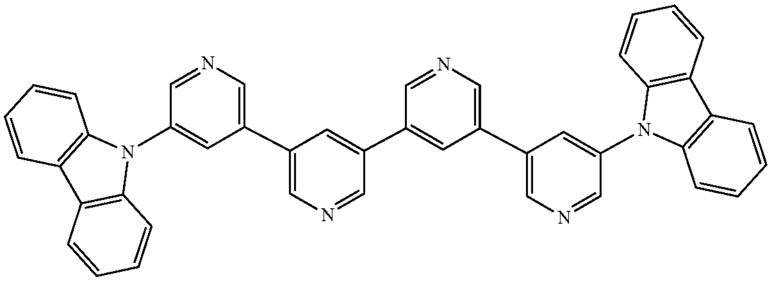
1-17
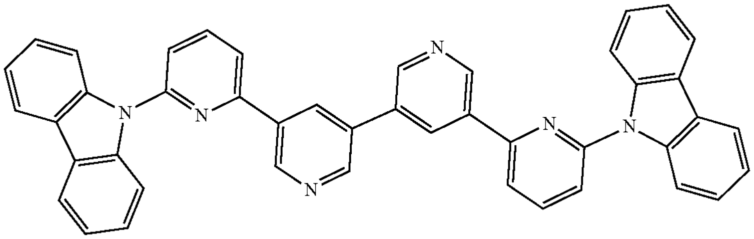
1-18
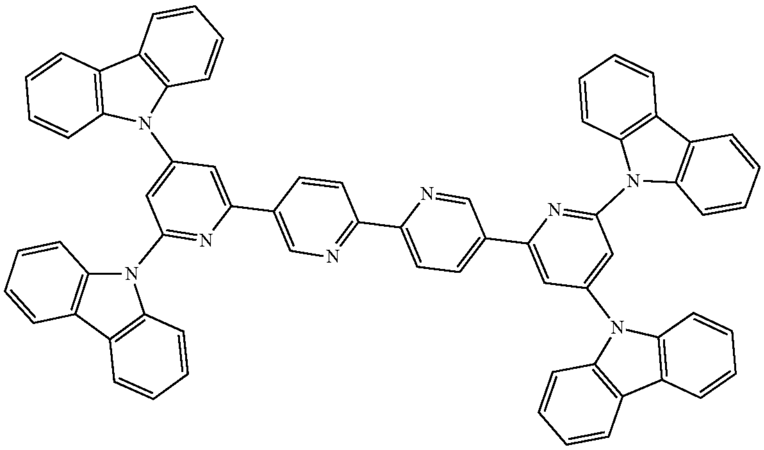

-continued
1-19
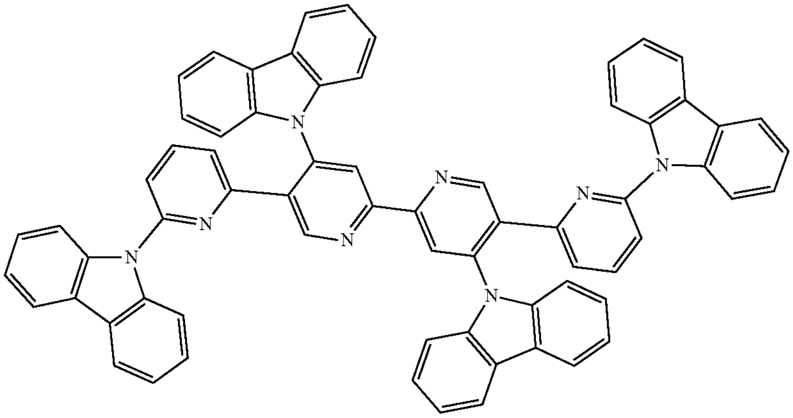
1-20
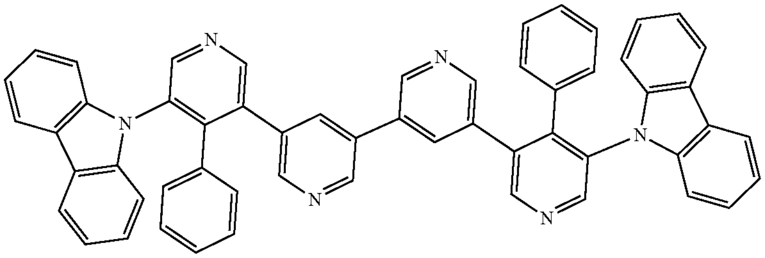
1-21
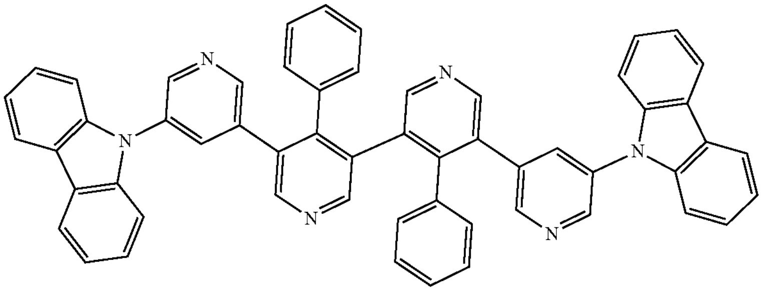
[C11]
1-22
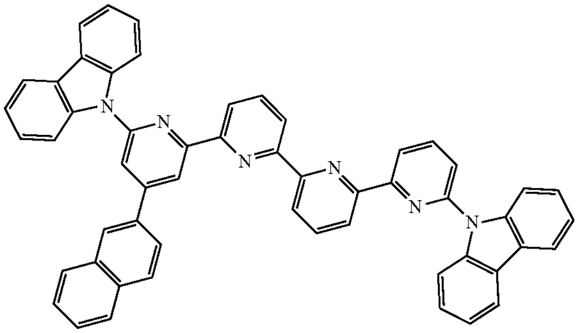
1-23
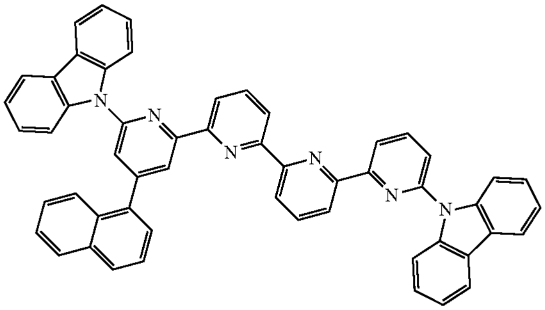

-continued
1-24
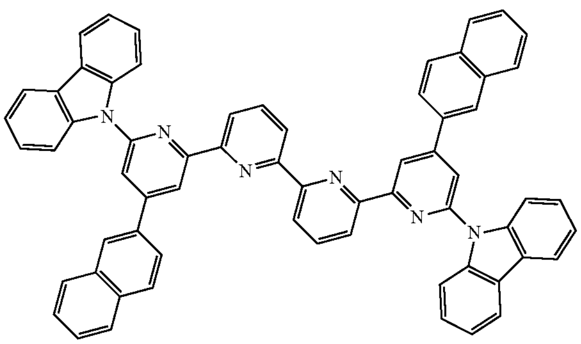
1-25
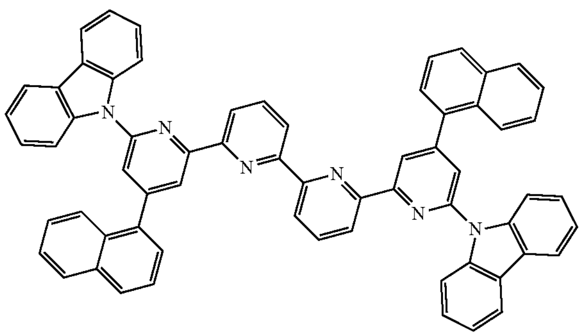
1-26
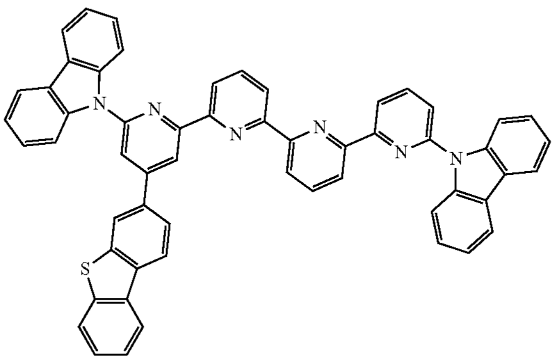
1-126
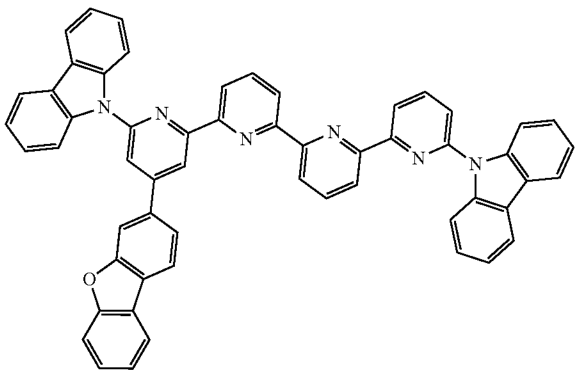
1-27
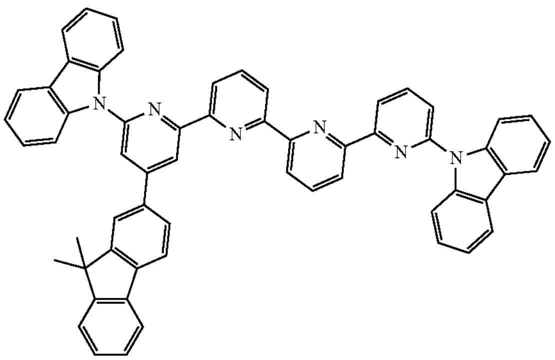
1-28
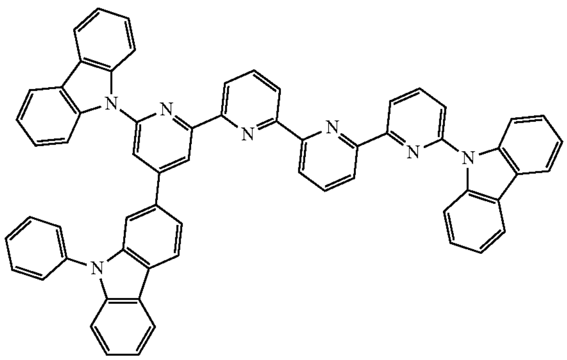
1-29
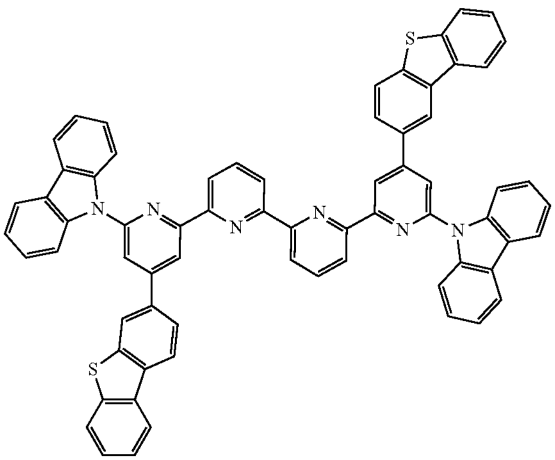
1-129
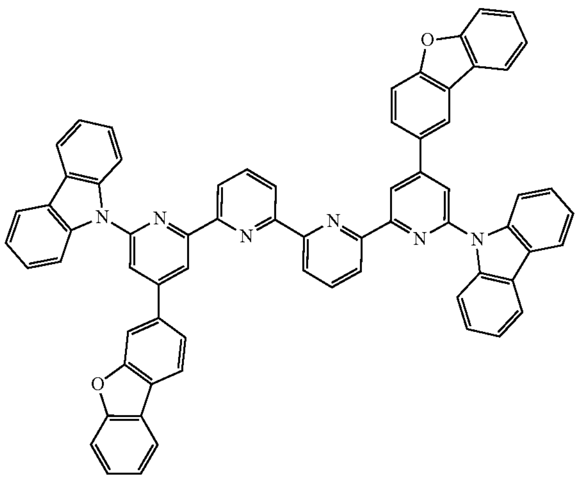

-continued
1-30
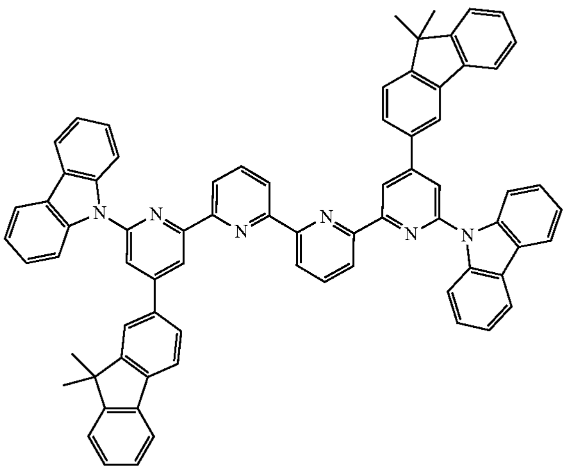
1-31
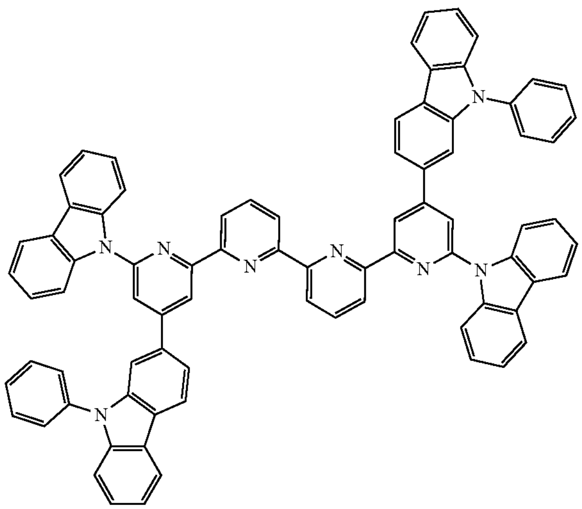
1-32
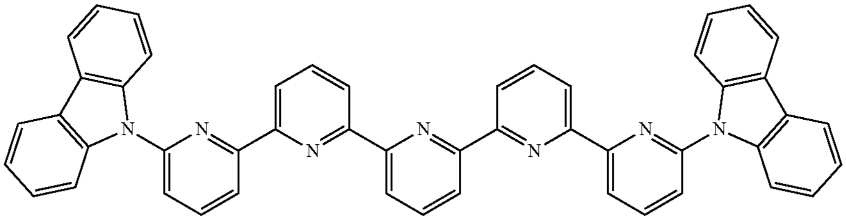
1-33
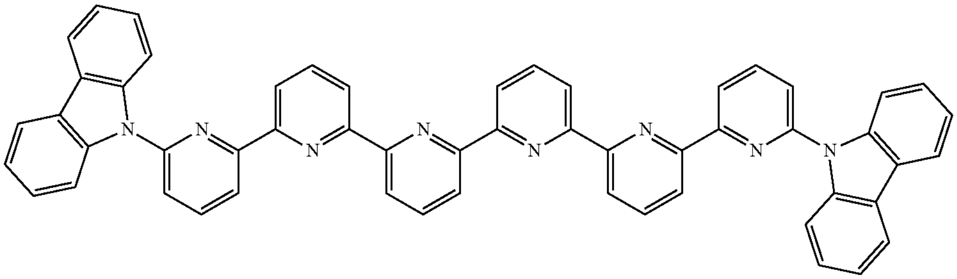
1-34
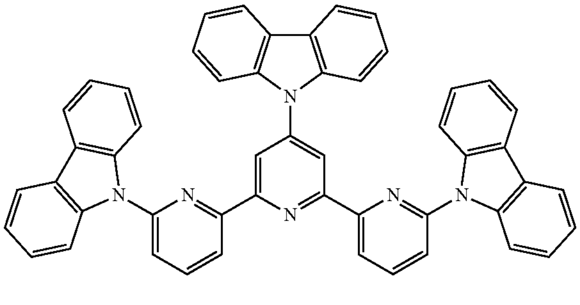
1-35
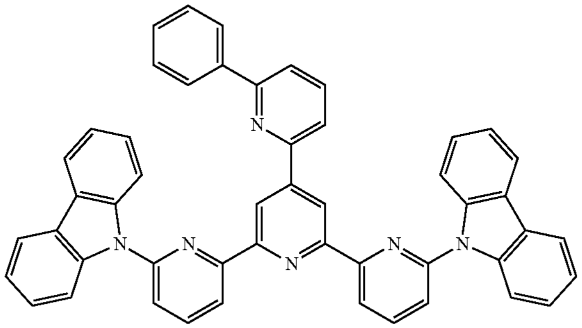

-continued
1-36
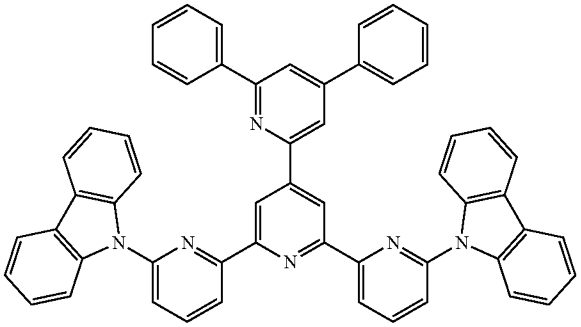
1-37
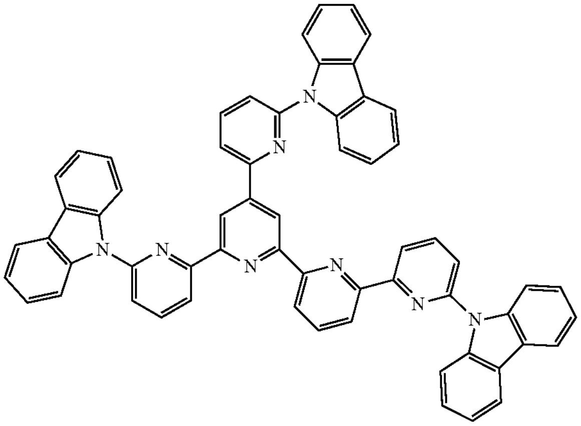
1-38
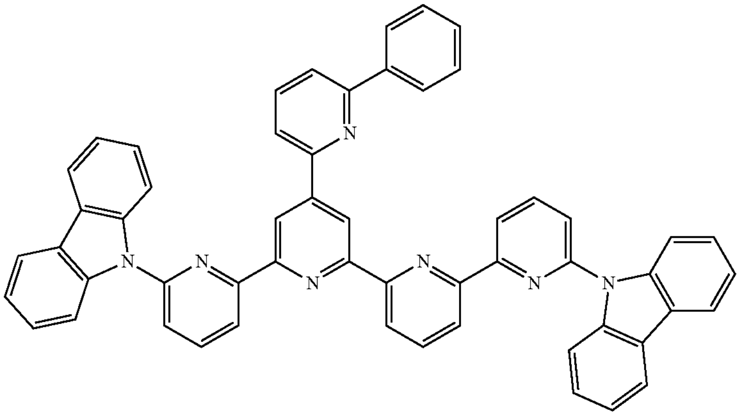
1-39
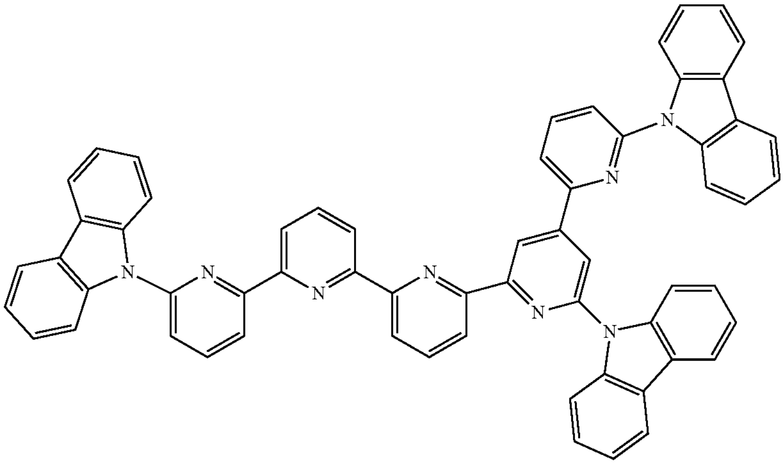

-continued
1-40
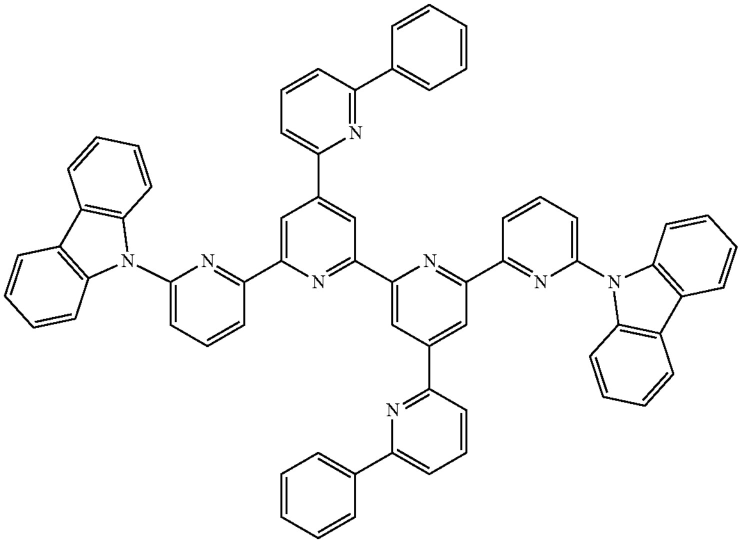
[C12]
1-41
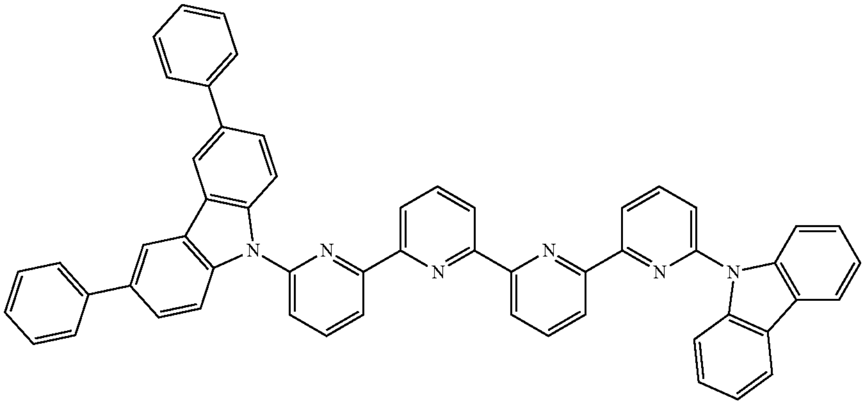
1-42
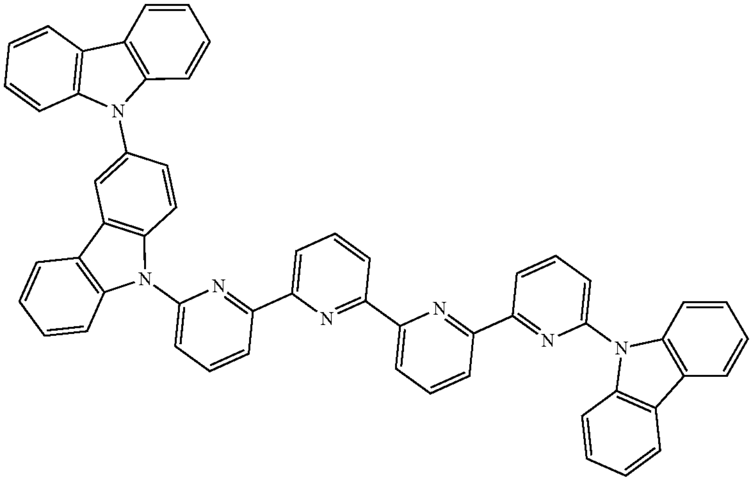

-continued
1-43
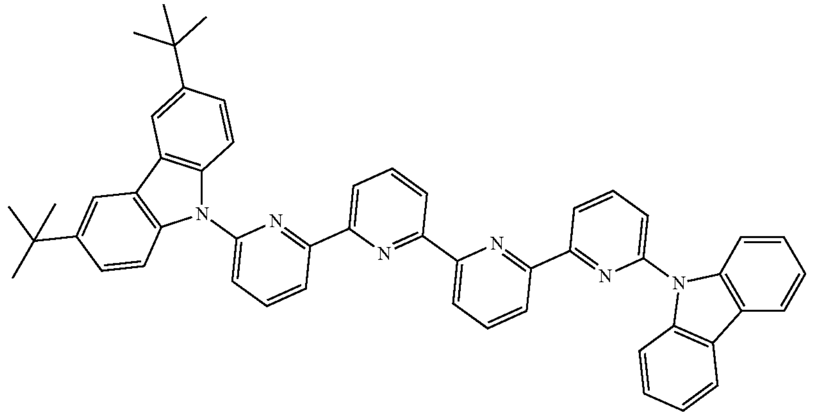
1-44
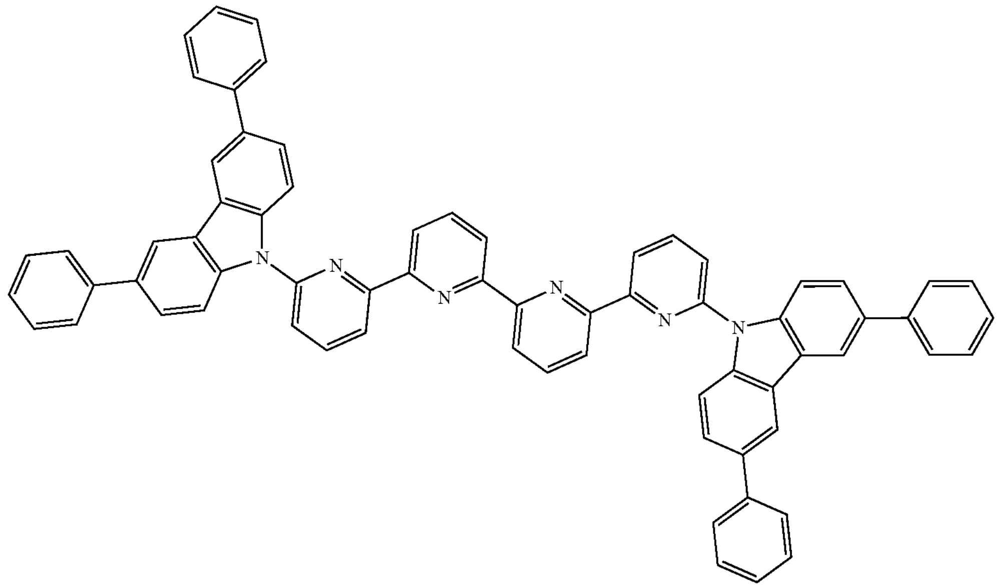
1-45
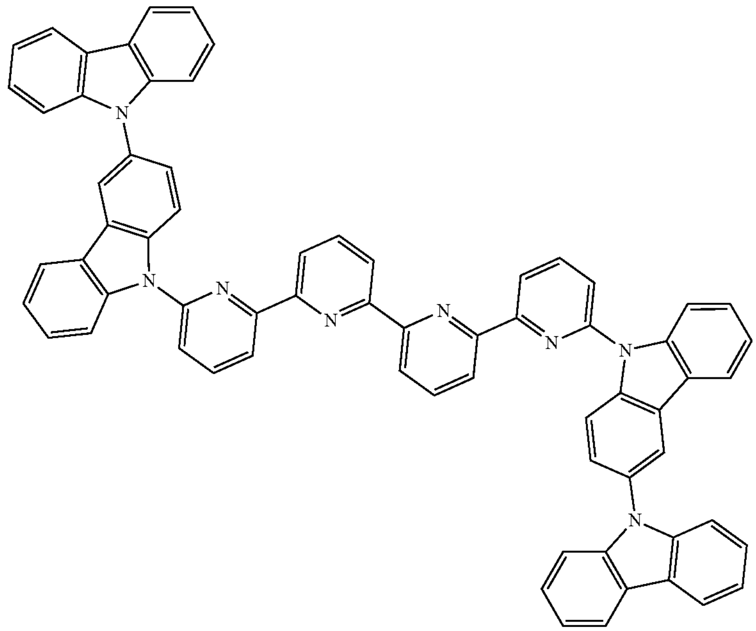

-continued
1-46
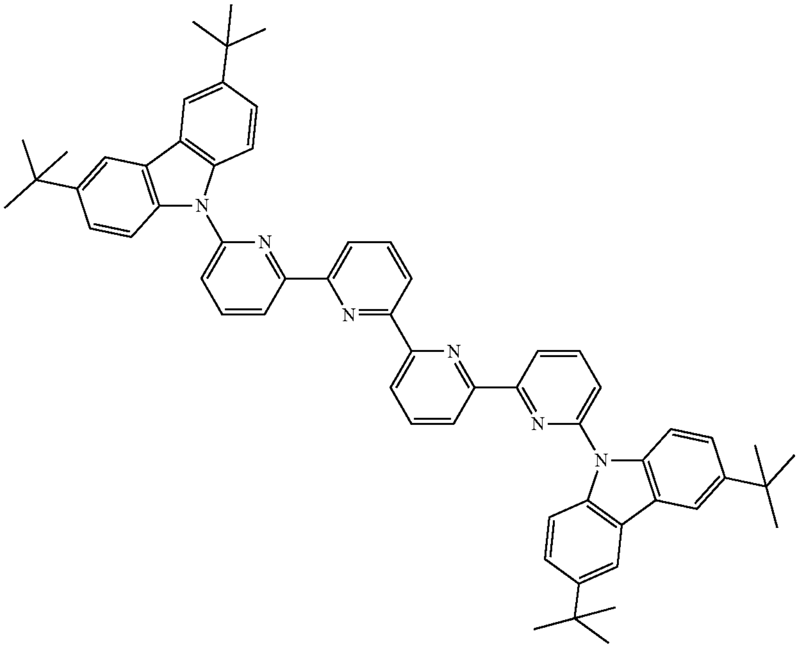
1-47
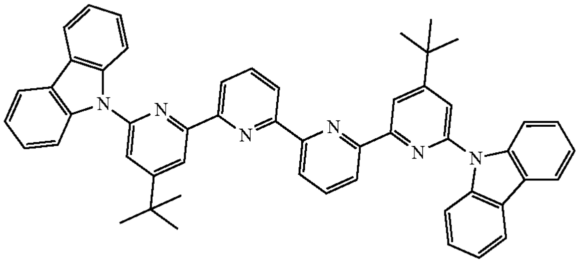
1-48
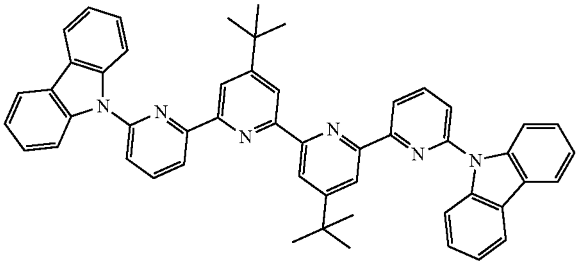
1-49
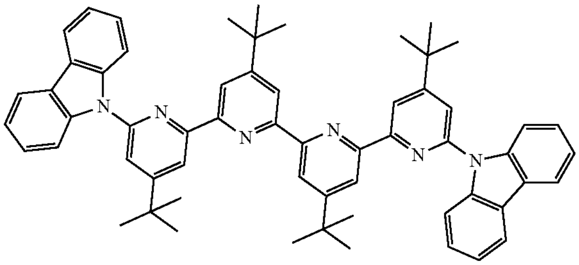
1-50
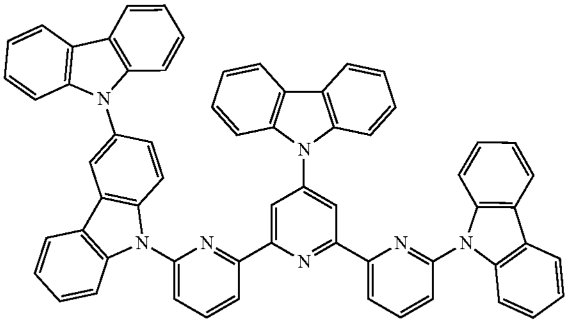
1-51
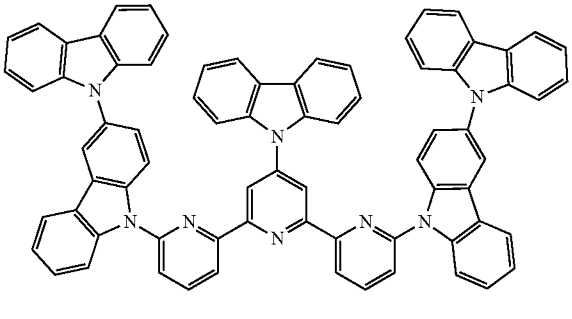
1-52
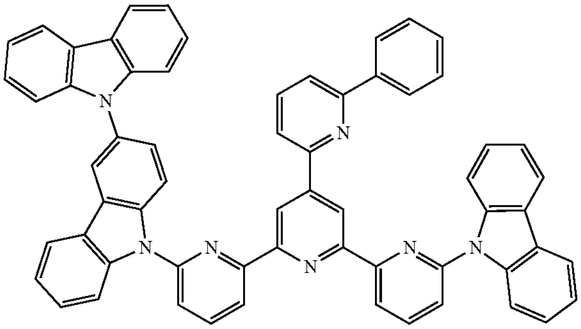

-continued
1-53
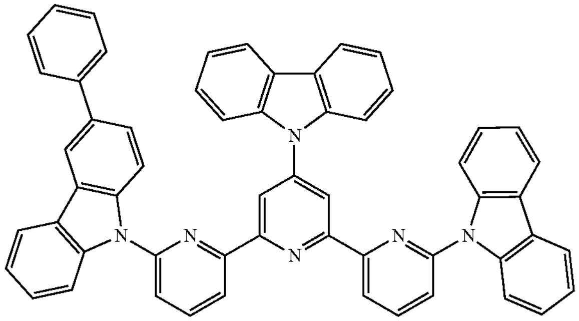
1-54
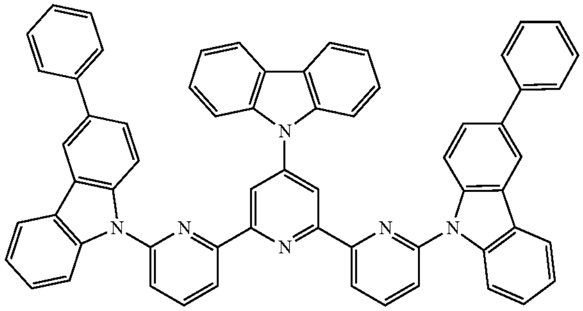
1-55
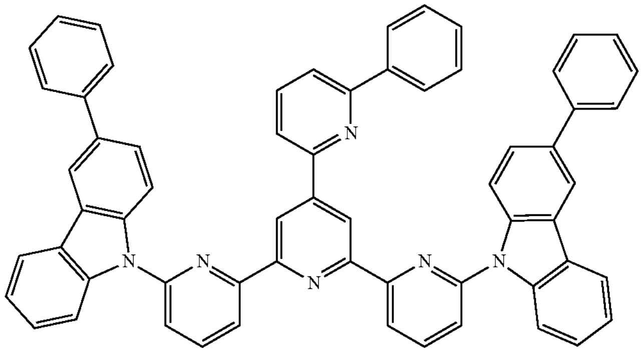
1-56
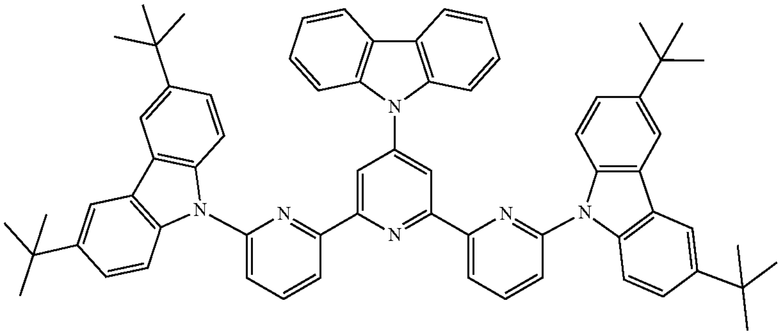
1-57
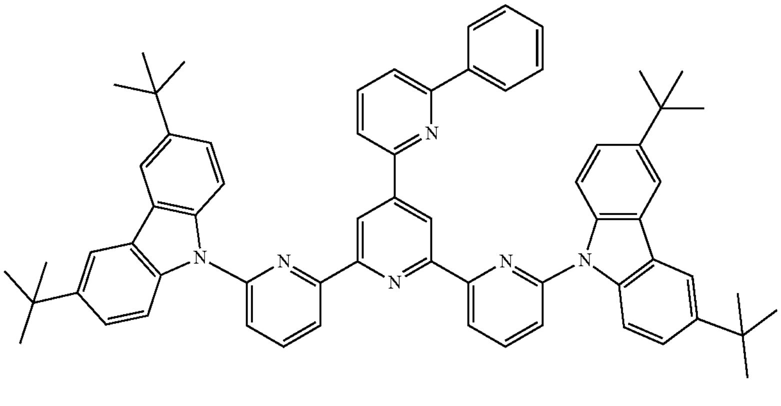

-continued
1-58
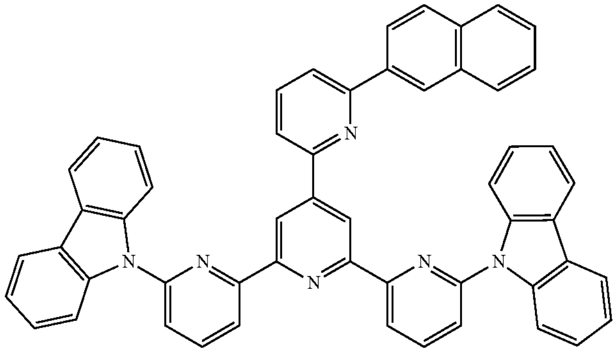
1-59
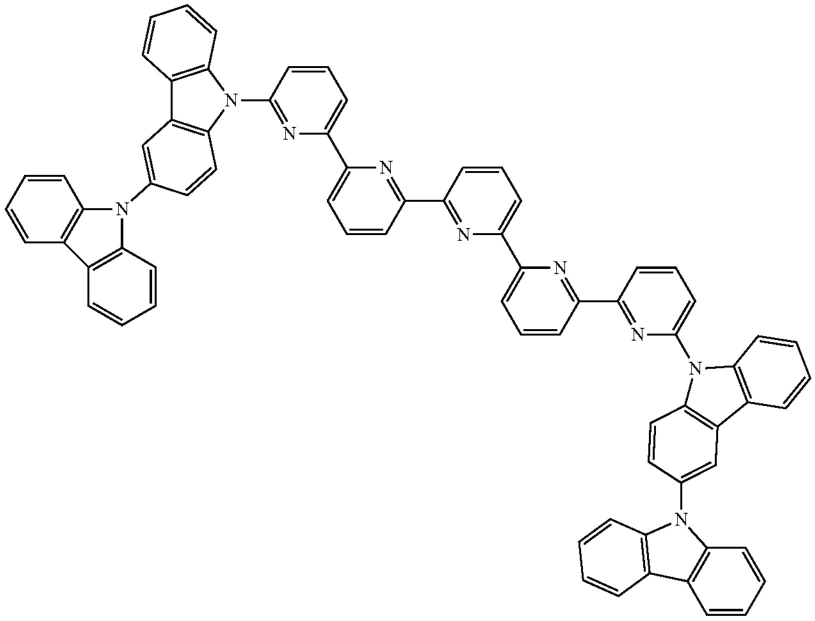
1-60
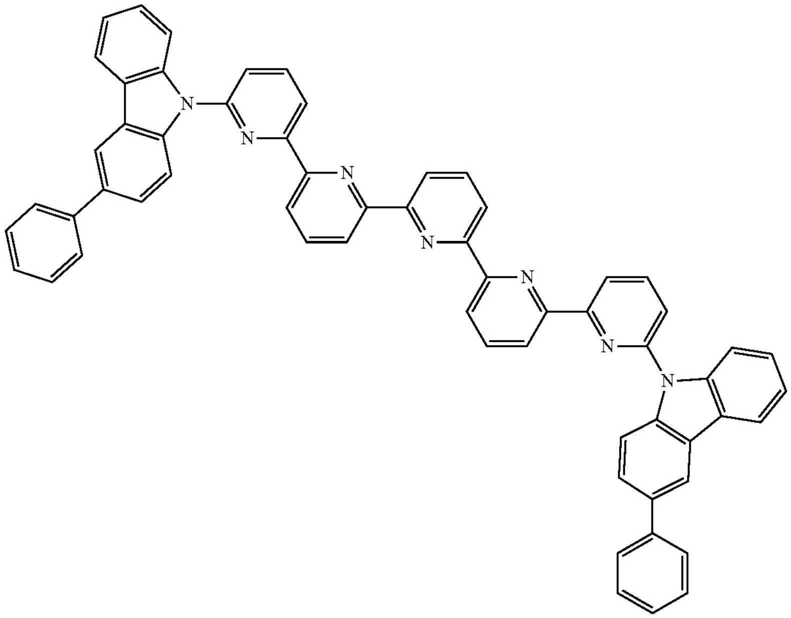

-continued
1-61
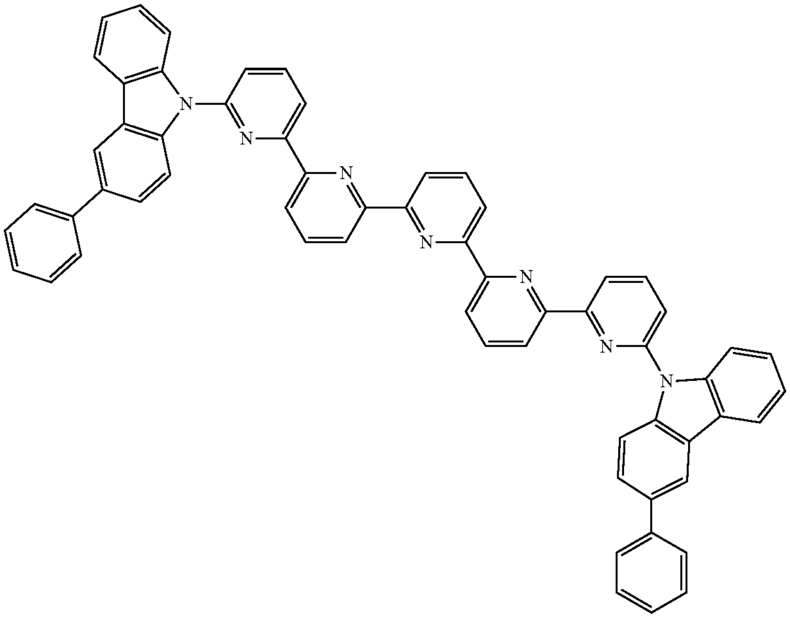
[C13]
1-62
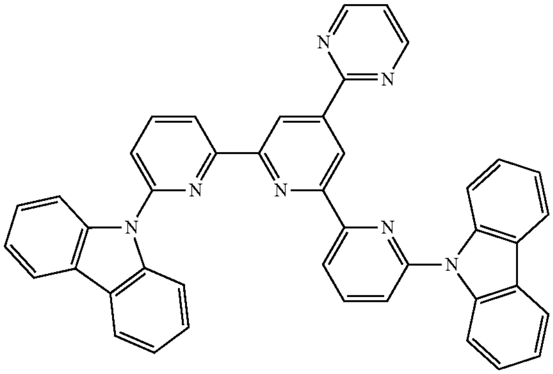
1-63
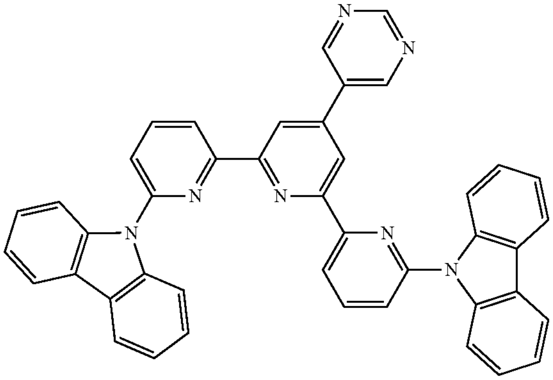
1-64
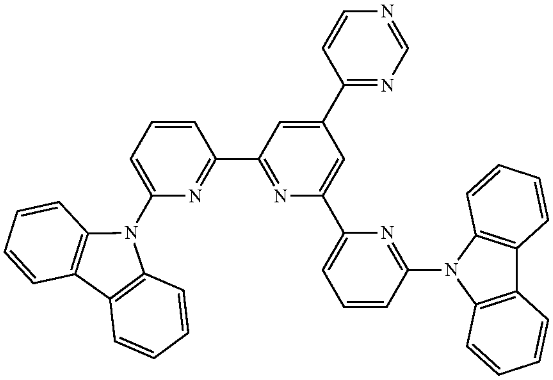
1-65
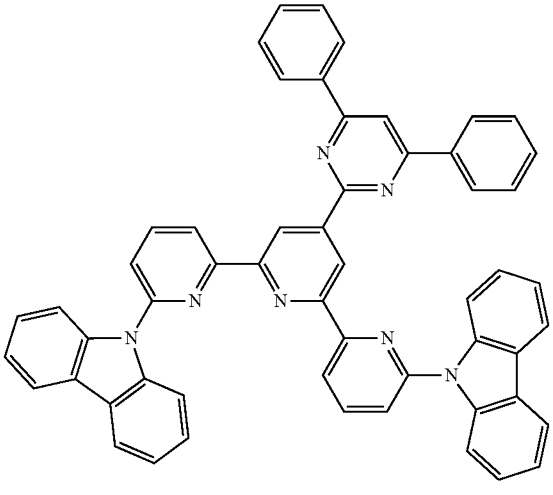

-continued
1-66
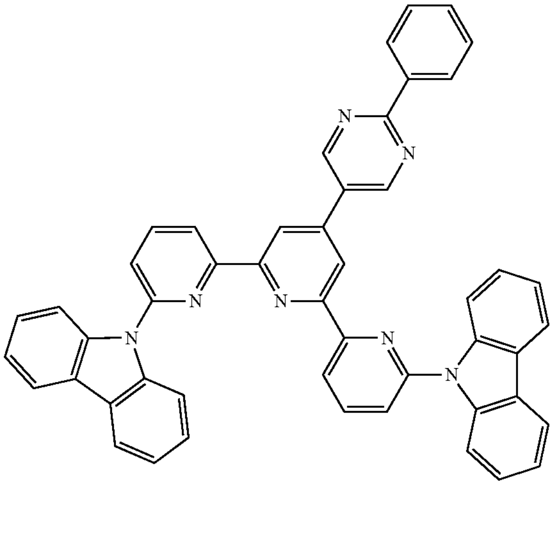
1-67
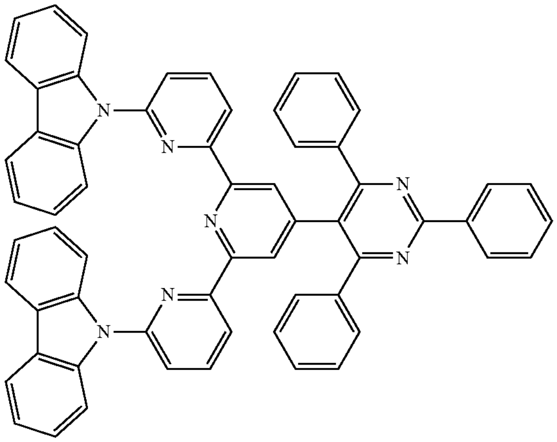
1-68
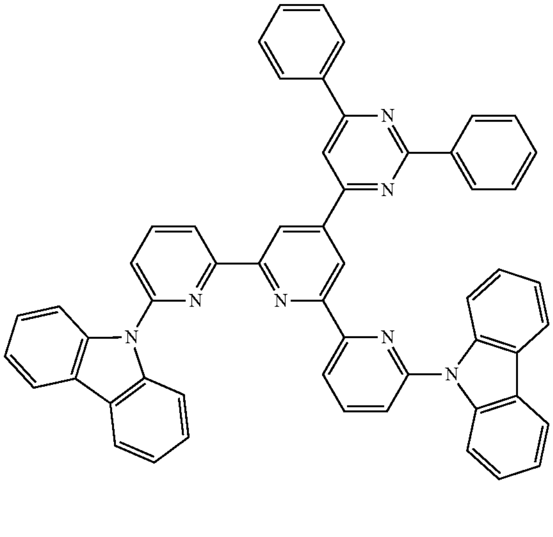
1-69
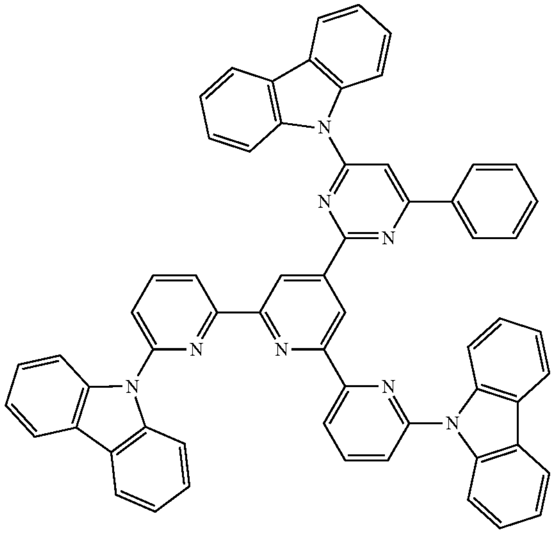
1-70
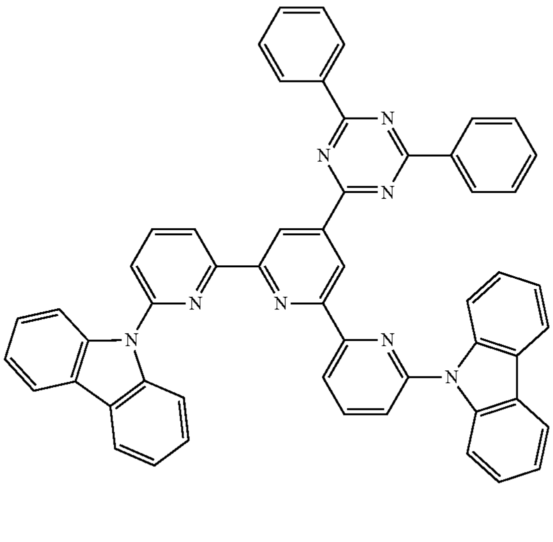
1-71
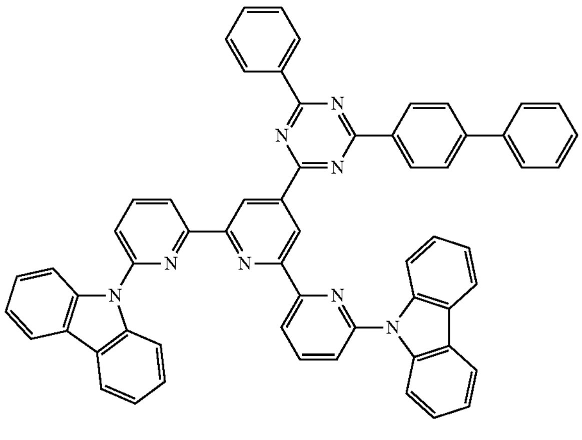

-continued
1-72
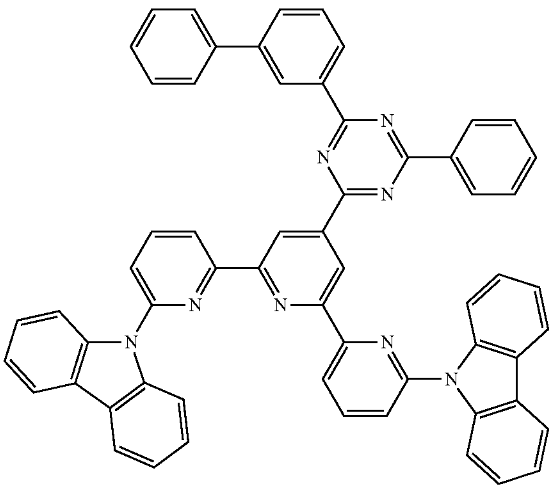
1-73
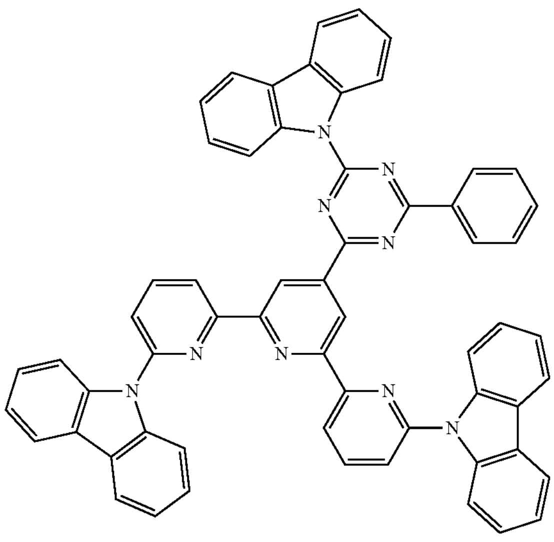
1-74
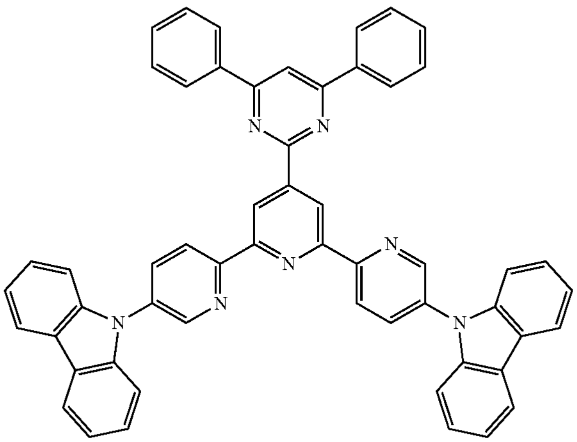
1-75
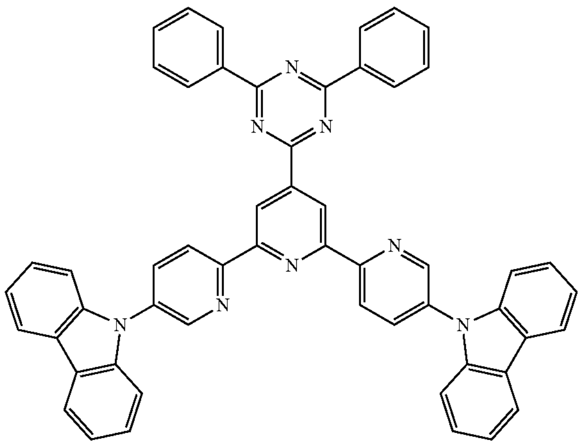
1-76
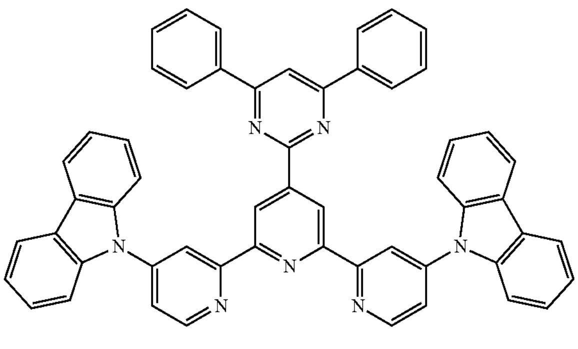
1-77
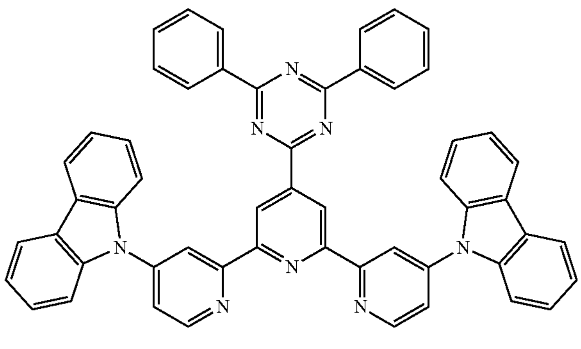

-continued
1-78
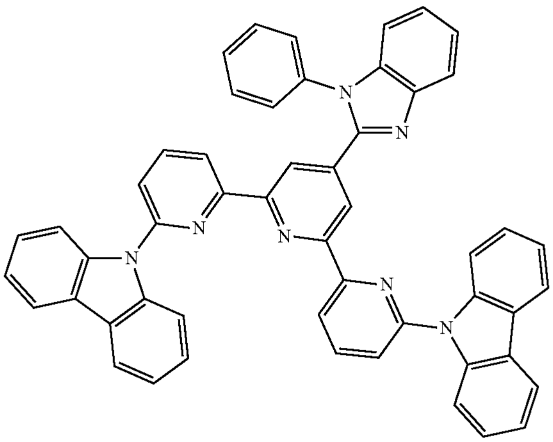
1-79
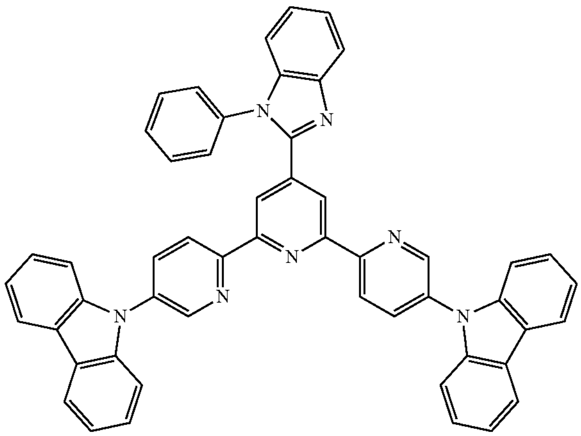
1-80
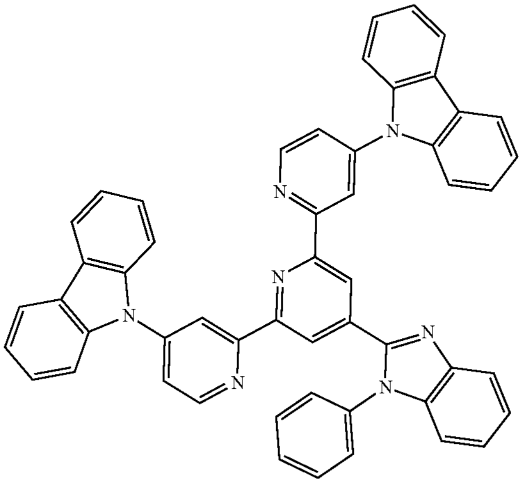
1-81
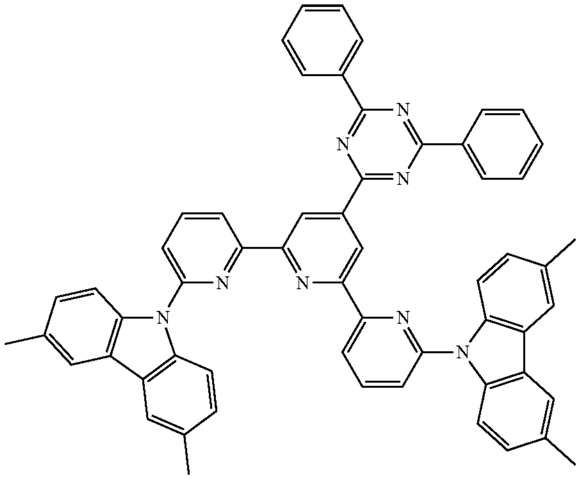
1-82
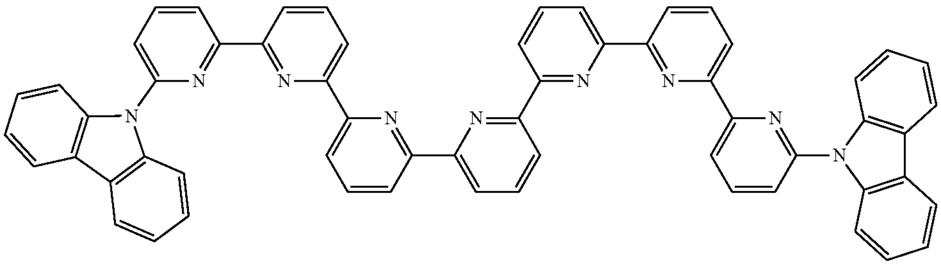
1-83
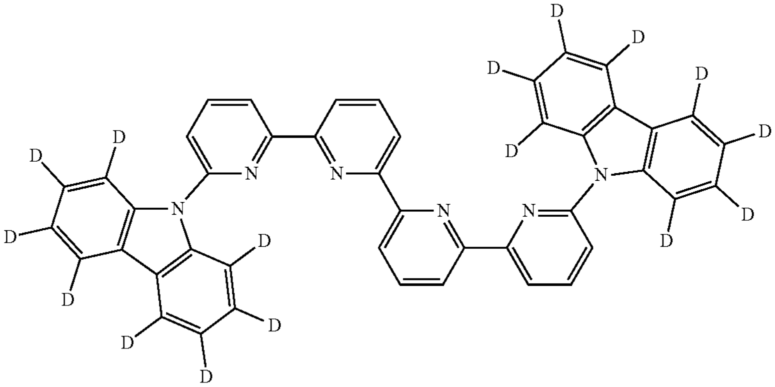

-continued
1-84
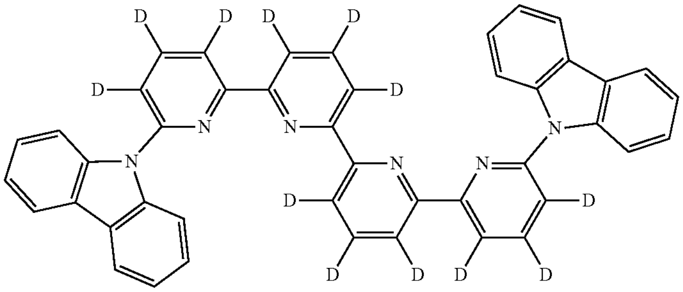
[C14]
1-85
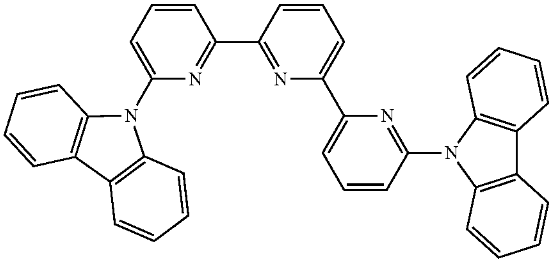
1-86
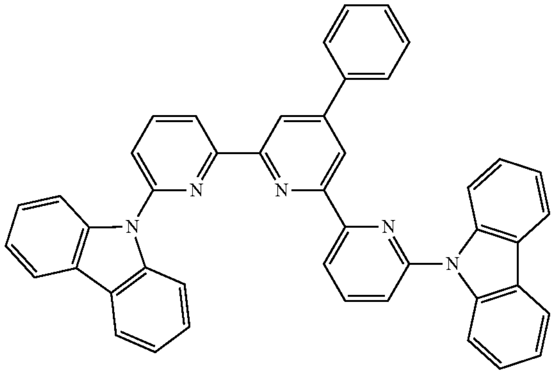
1-87
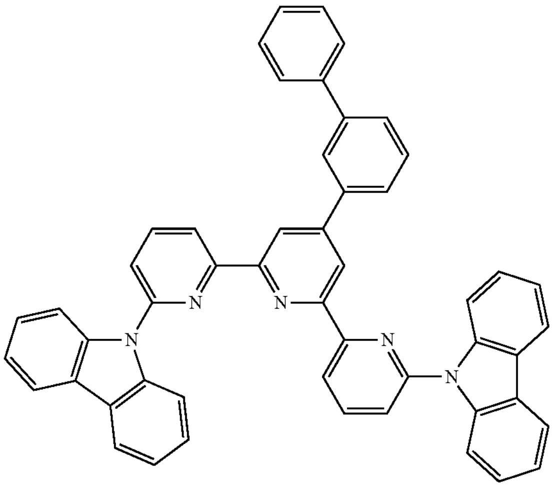
1-88
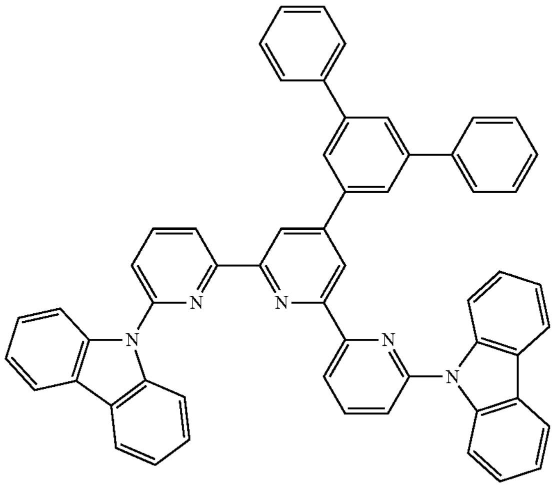
1-89
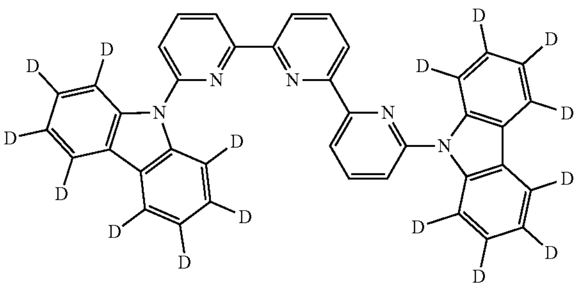
1-90
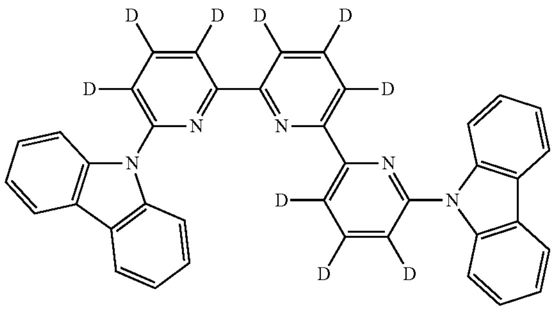

-continued
1-91
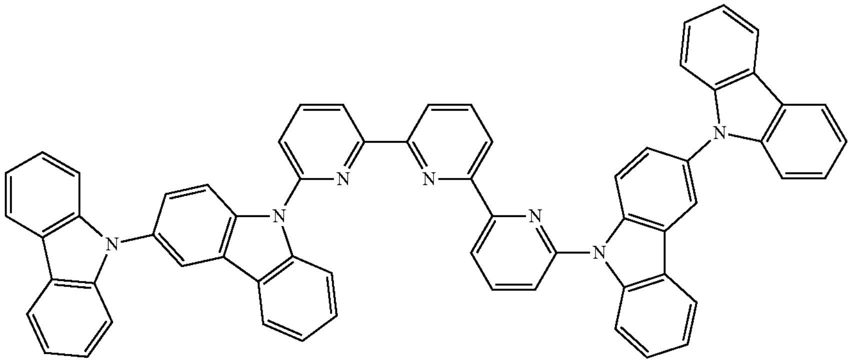
1-92
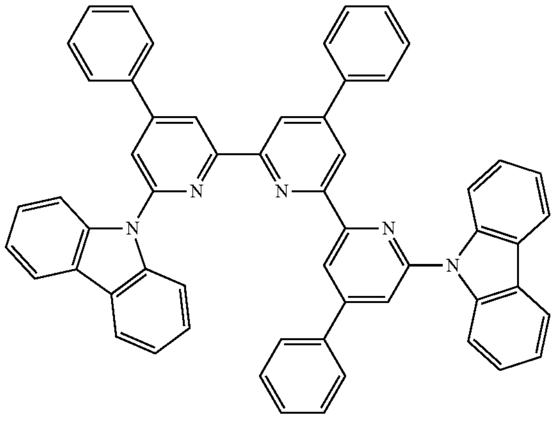
1-93
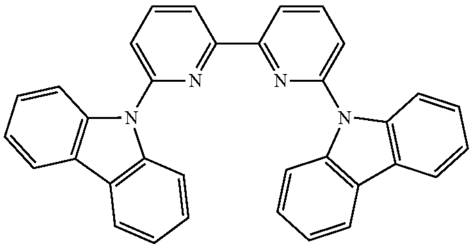
1-94
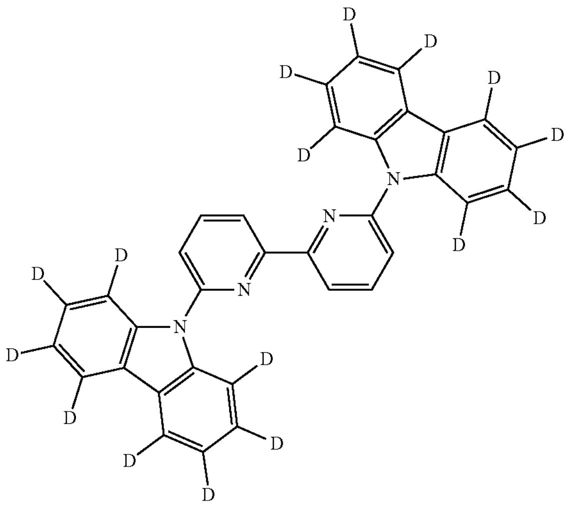
1-95
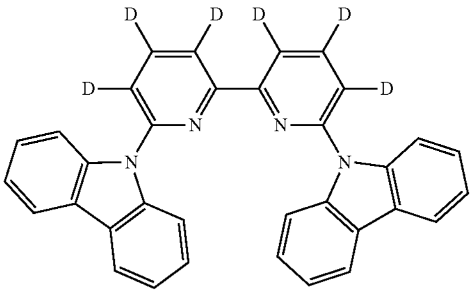

-continued
1-195
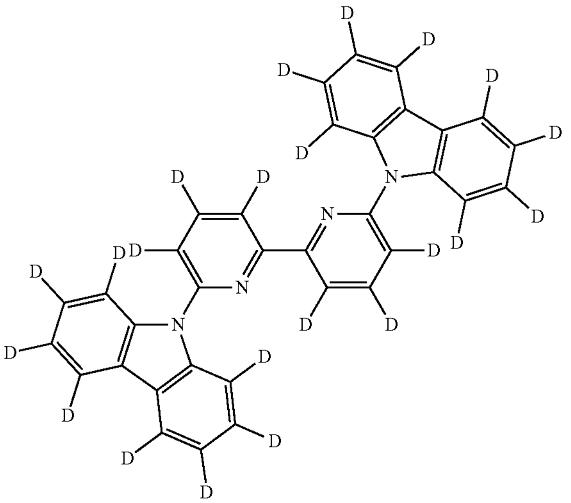
1-96
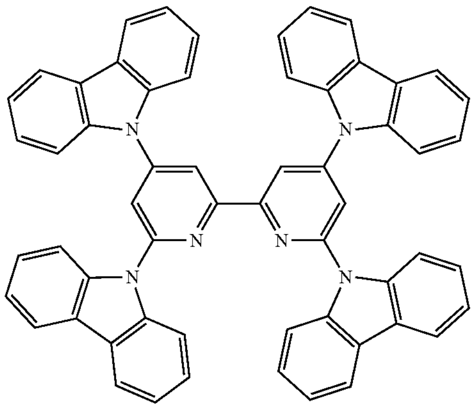
1-97
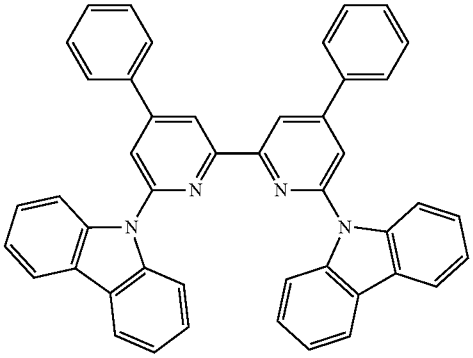
1-98
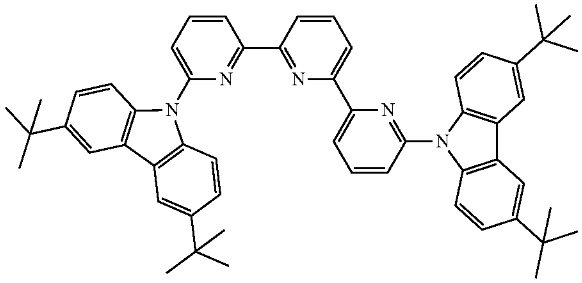
1-99
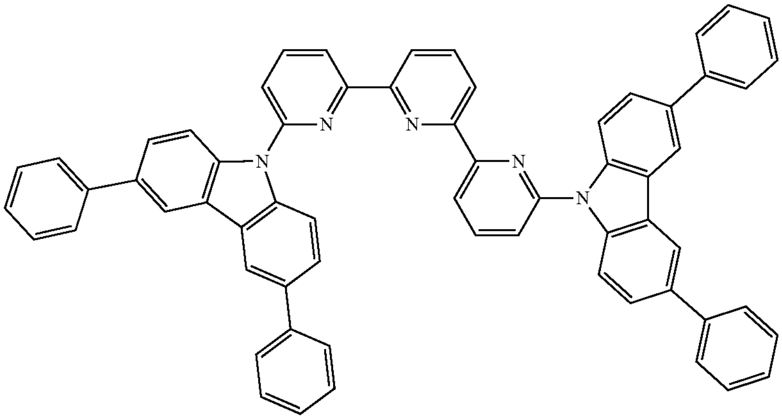
1-100
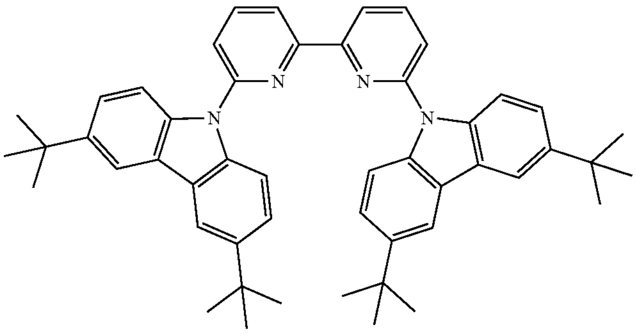

-continued 1-101

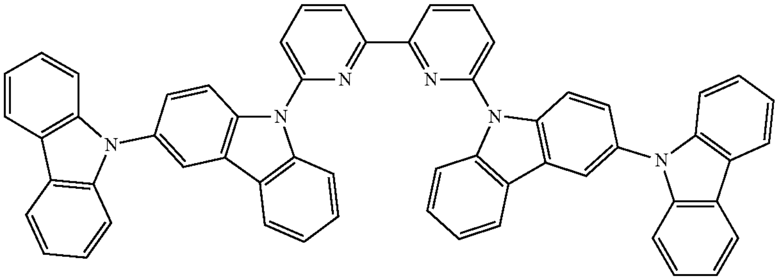

1-102

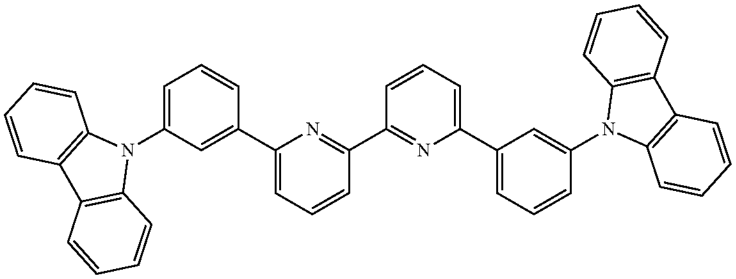

1-103

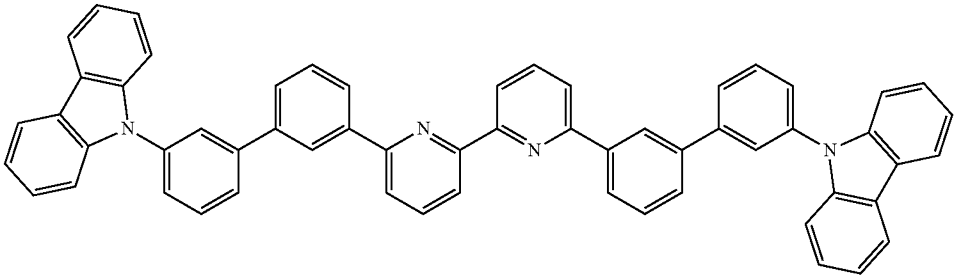

1-104

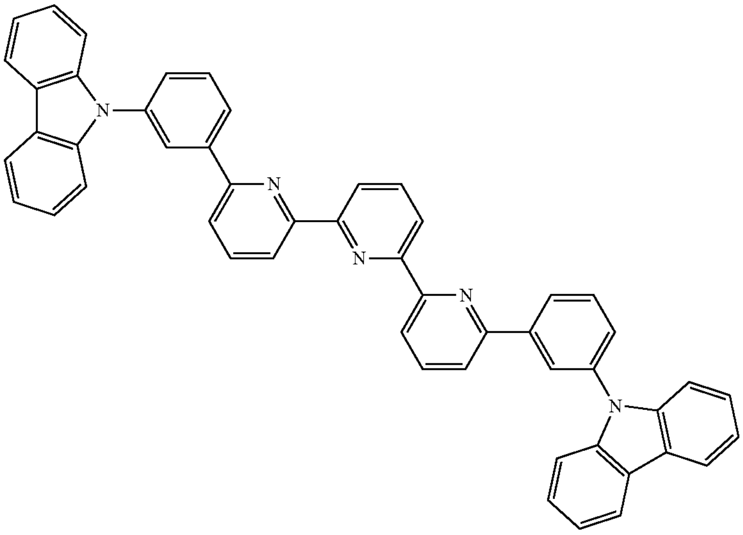

The second host is selected from compounds represented by the general formula (2), (3), (4) or (5).

The general formula (2) representing the second host and formula (6) representing preferred aspects thereof will be described. In the general formula (2) and formula (6), the same symbols have the same meaning.

$R^8$ and $R^9$ independently represent hydrogen, an aromatic hydrocarbon group having 6 to 14 carbon atoms, or a linked aromatic group in which two aromatic rings of the aromatic hydrocarbon group are linked; preferably, hydrogen or an aromatic hydrocarbon group having 6 to 12 carbon atoms; and more preferably an aromatic hydrocarbon group having 6 to 10 carbon atoms. It is a preferred embodiment that: $R^8$ is hydrogen; or $R^8$ is hydrogen and $R^9$ is the above aromatic hydrocarbon group or linked aromatic group.

In the case of $R^8$ and $R^9$ being an aromatic hydrocarbon group or a linked aromatic group, specific examples thereof include aromatic hydrocarbons such as benzene, naphthalene, anthracene, phenanthrene, fluorene and biphenyl, or an aromatic group or linked aromatic group generated by removing one H from a compound in which two aromatic rings of these aromatic hydrocarbons are linked. Preferred are aromatic groups generated from benzene, naphthalene, anthracene, phenanthrene, or linked aromatic groups in which two of the aromatic groups are linked to each other. More preferred are aromatic groups generated from benzene, naphthalene, phenanthrene or biphenyl. It is further preferred that $R^8$ and $R^9$ are a phenyl group.

$R^8$ and $R^9$ may be hydrogen; but in that case, one of them is preferably the aromatic group or linked aromatic group. It is further preferred that $R^8$ is hydrogen and $R^9$ is a phenyl group. In addition, the aromatic group or linked aromatic group may have a substituent, and preferred substituents are an alkyl group having 1 to 12 carbon atoms or an alkoxy group having 1 to 12 carbon atoms.

$L^4$ and $L^5$ are a phenylene group, and the phenylene group may be any of o-phenylene group, m-phenylene group and p-phenylene group. Preferred is p-phenylene group or m-phenylene group. Then, $L^4$ and $L^5$ are preferably different from each other. In this case, when $R^8$ and $R^9$ are hydrogen, they are treated as a phenyl group, different from a phenylene group.

Specific examples of the compounds represented by the general formulas (2) and (6) are described below, but the compounds are not limited to these exemplified compounds.

[C15]

2-1

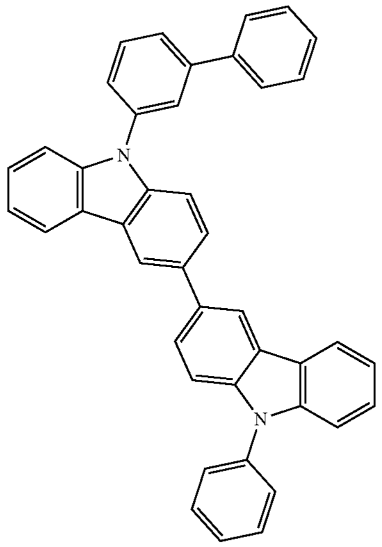

-continued 2-2

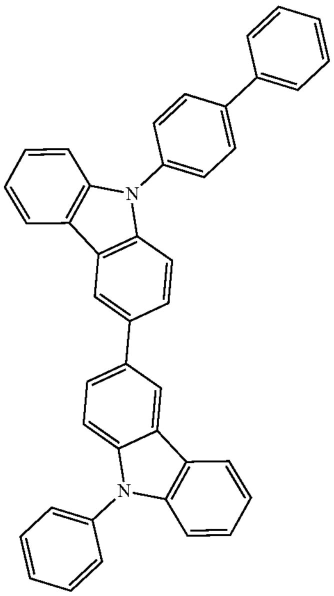

2-3

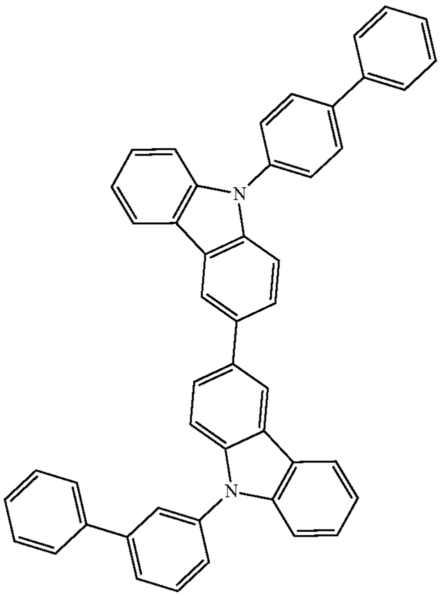

2-4

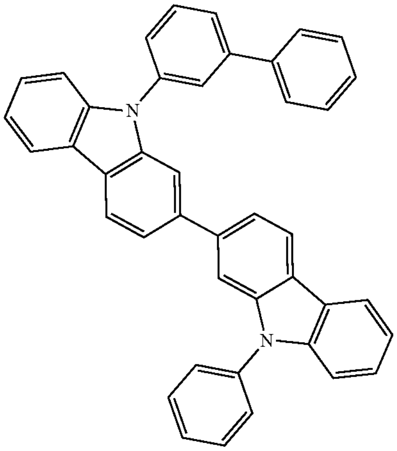

-continued
2-5
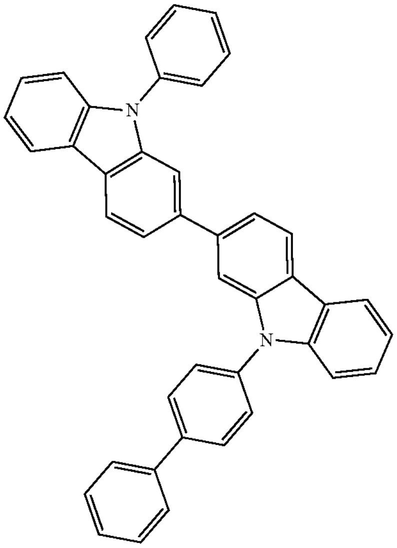
2-6
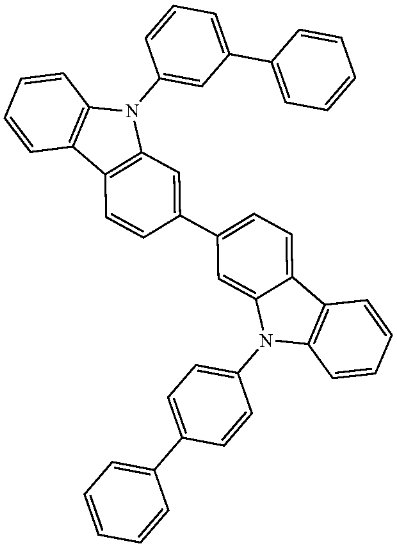
2-7
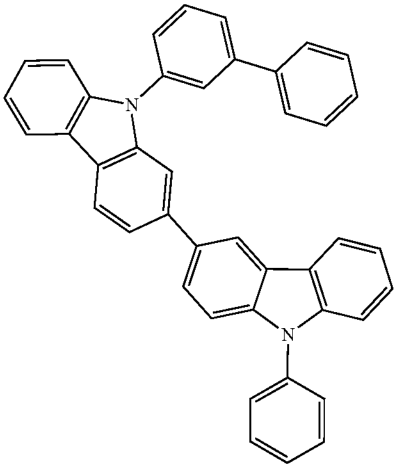
-continued
2-8
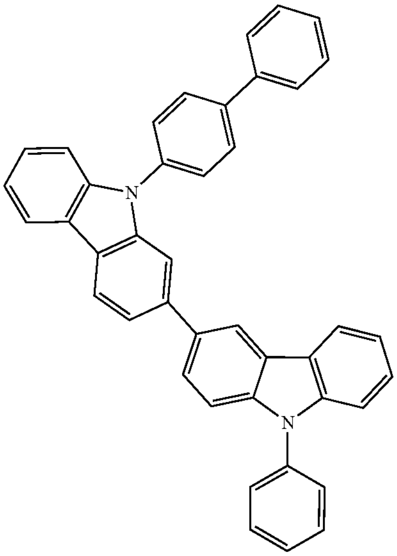
2-9
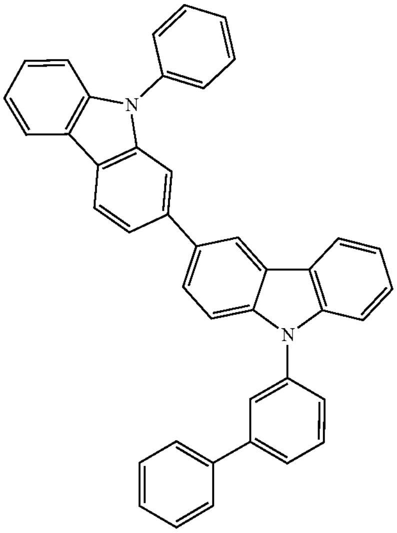
2-10
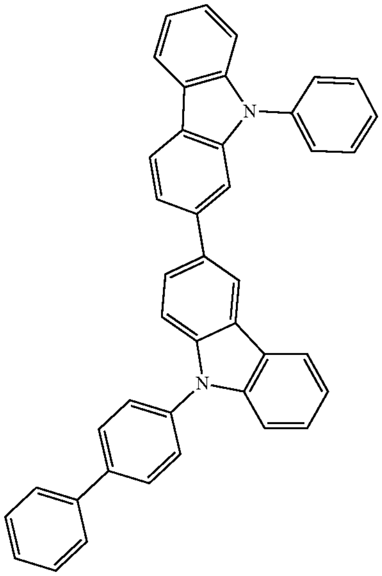

-continued
2-11
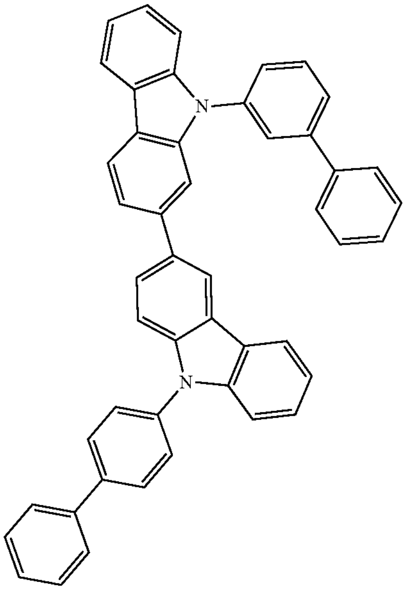
2-12
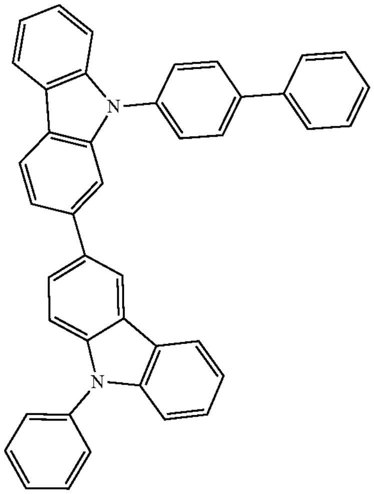
[C16]
2-13
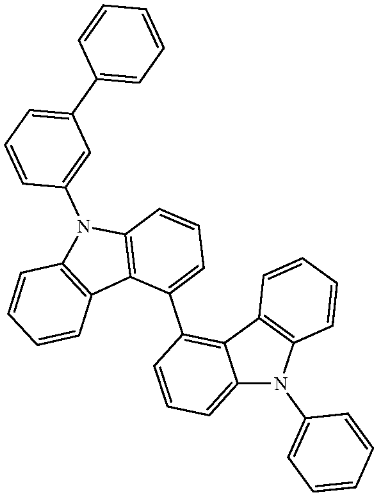
-continued
2-14
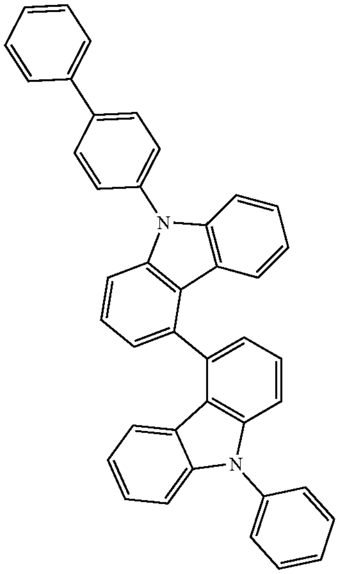
2-15
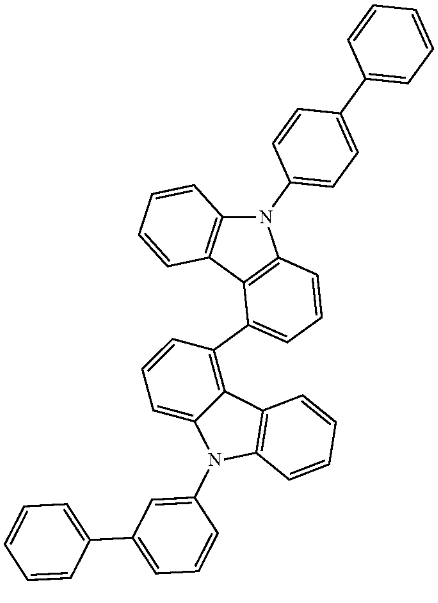
2-16
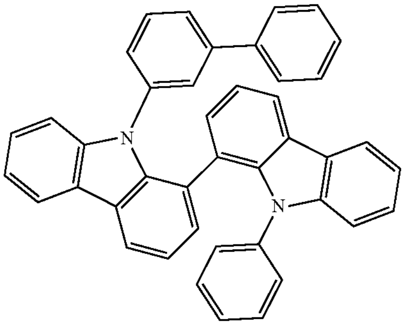

-continued
2-17
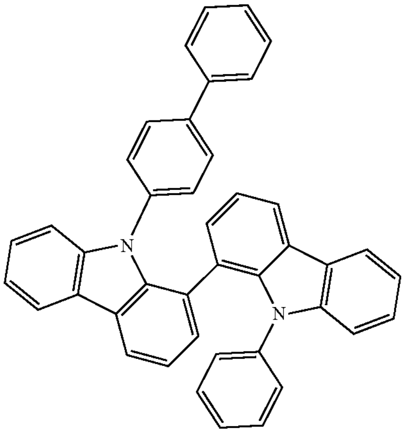
2-18
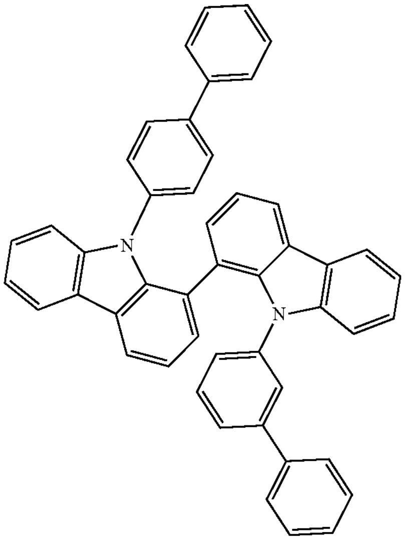
2-19
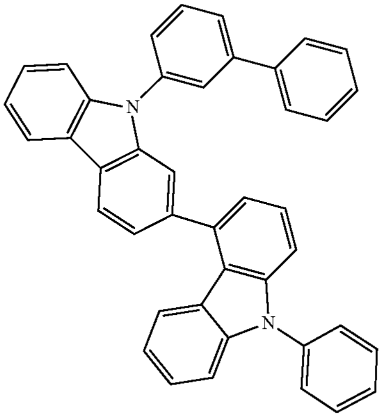
-continued
2-20
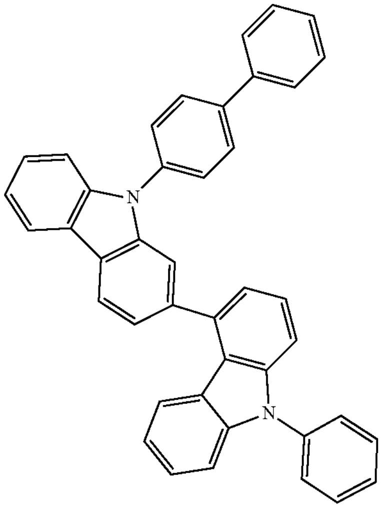
2-21
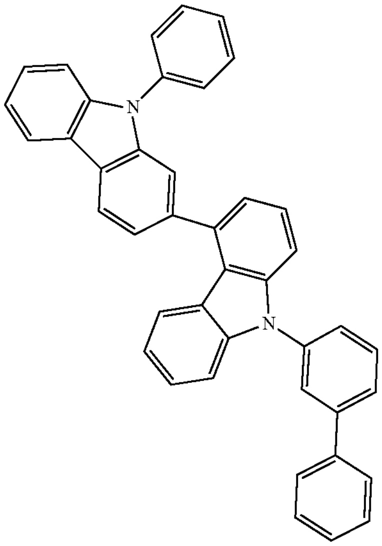
2-22
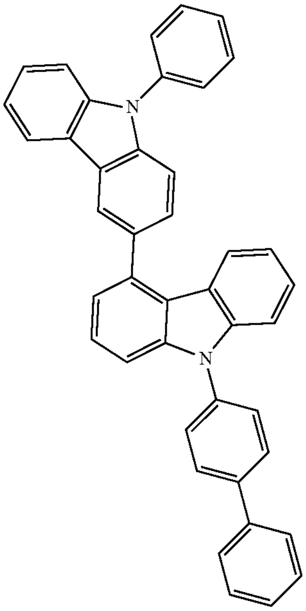

-continued
2-23
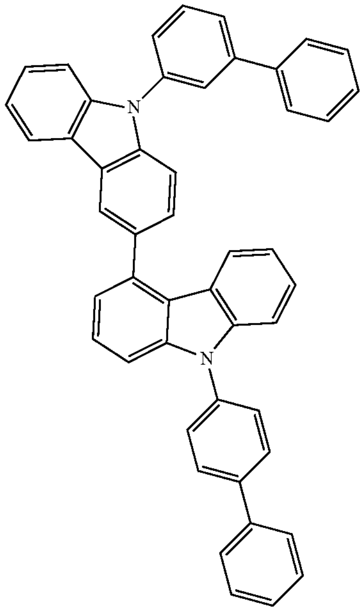
2-24
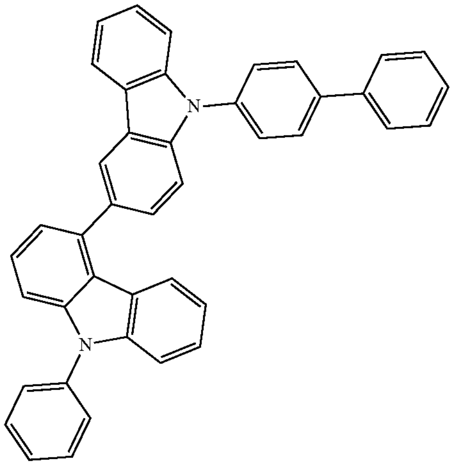
[C17]
2-25
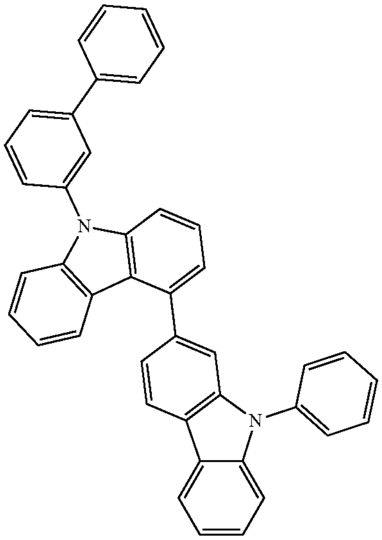
-continued
2-26
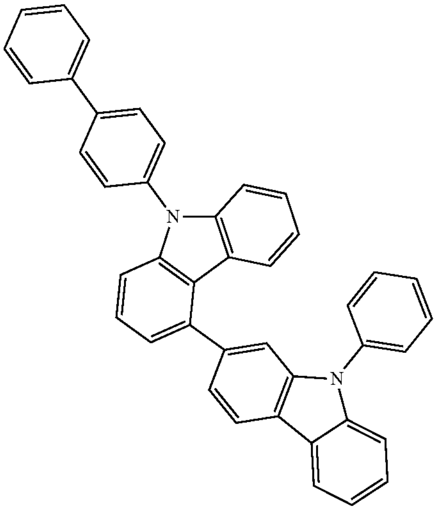
2-27
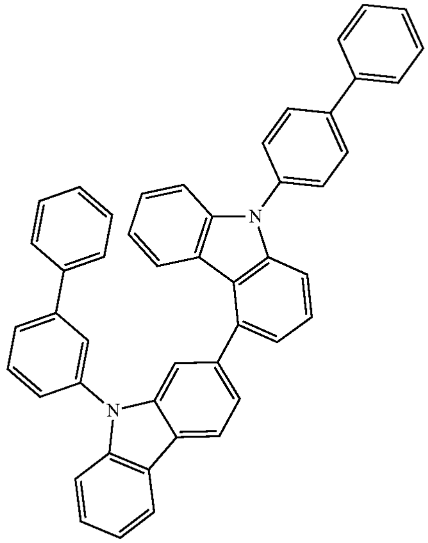
2-28
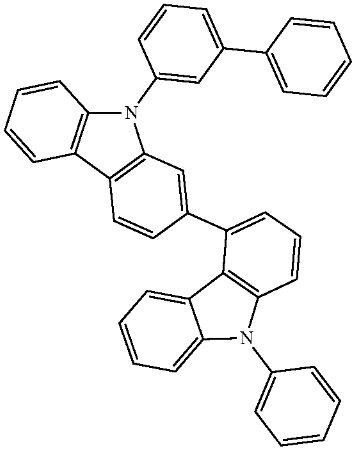

-continued
2-29
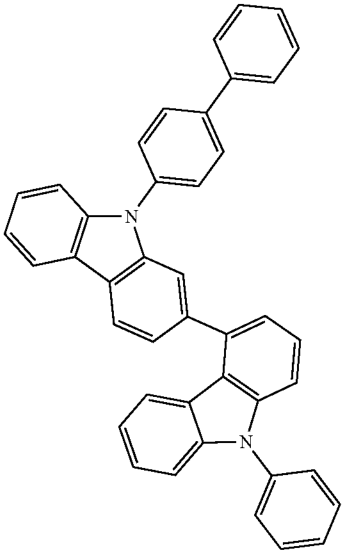
2-30
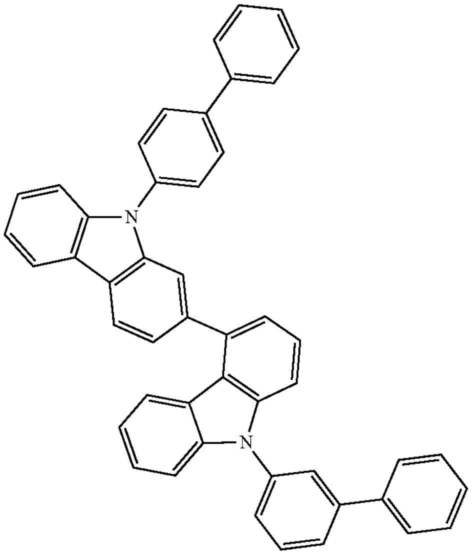
2-31
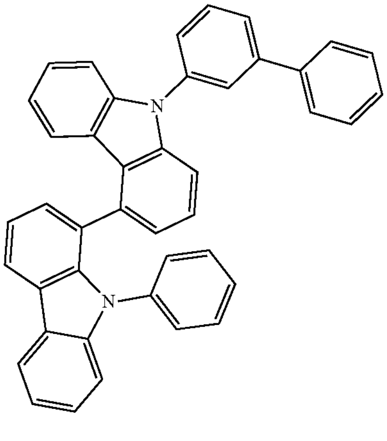
-continued
2-32
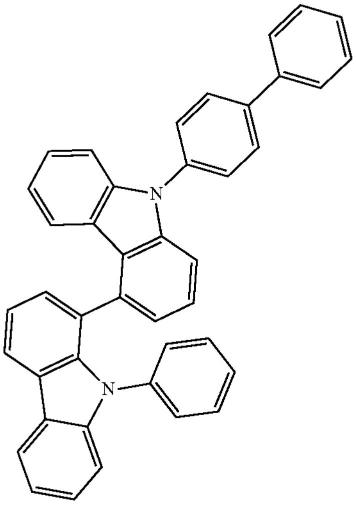
2-33
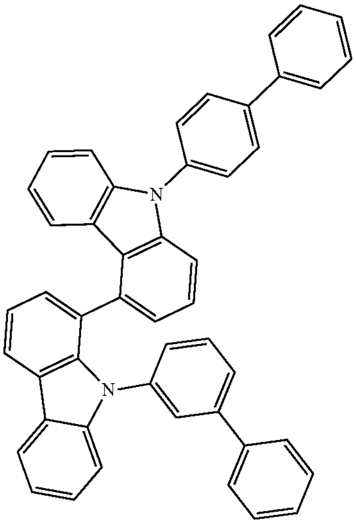
2-122
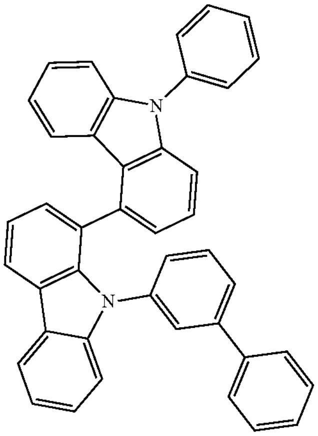

-continued
2-123
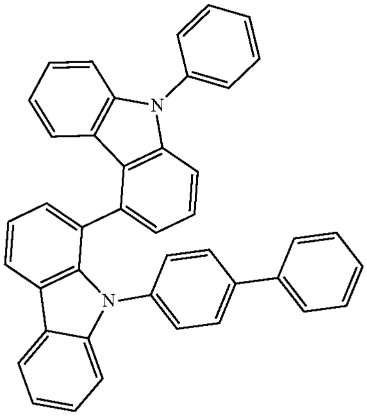
2-124
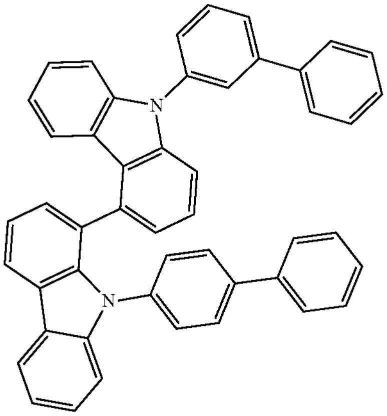
[C18]
2-125
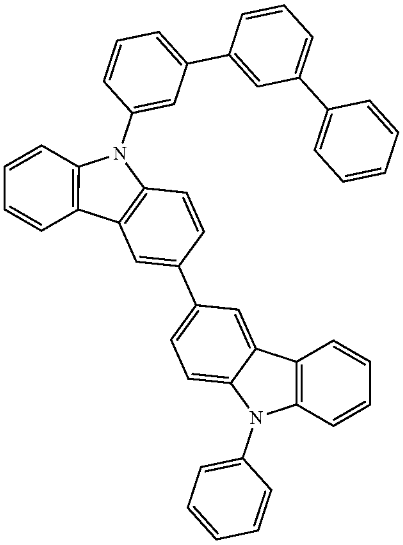
-continued
2-126
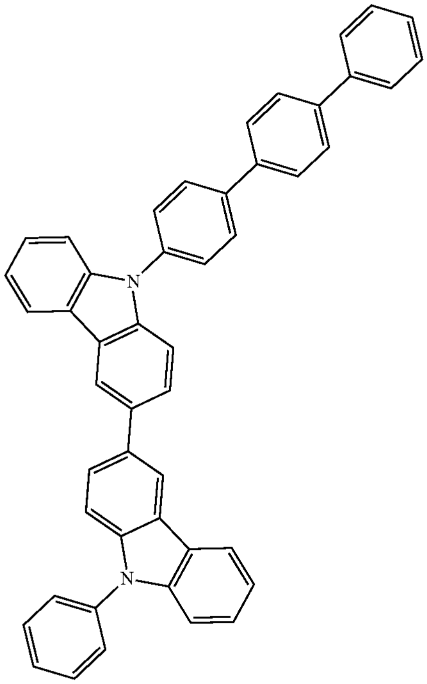
2-127
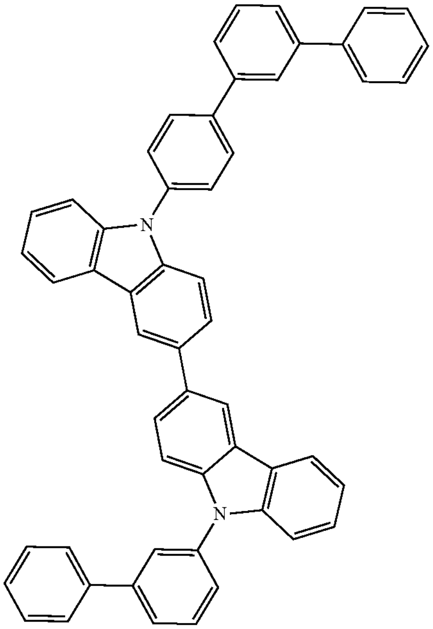

-continued
2-128
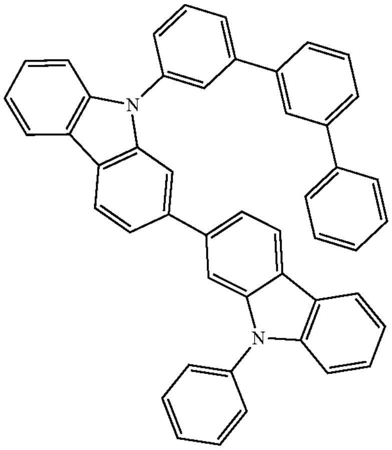
2-129
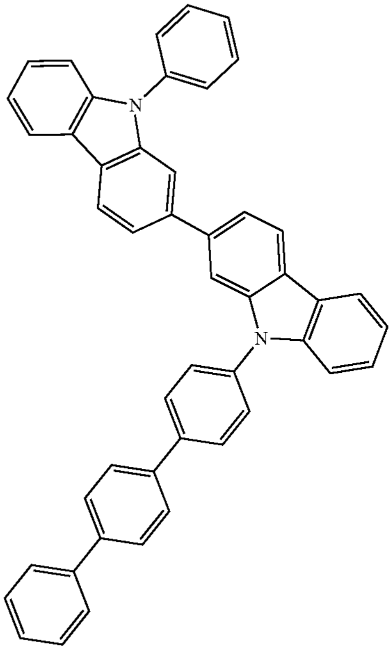
-continued
2-130
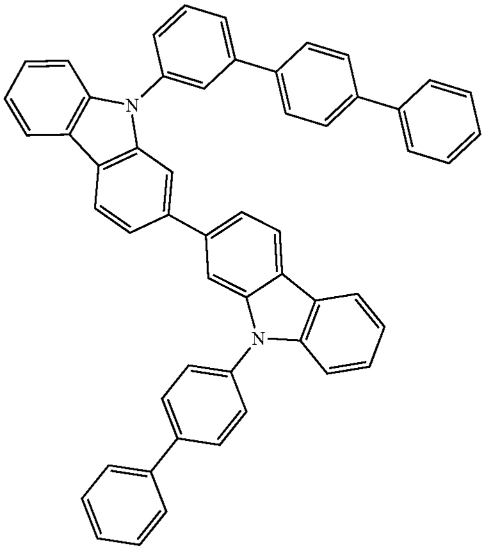
2-131
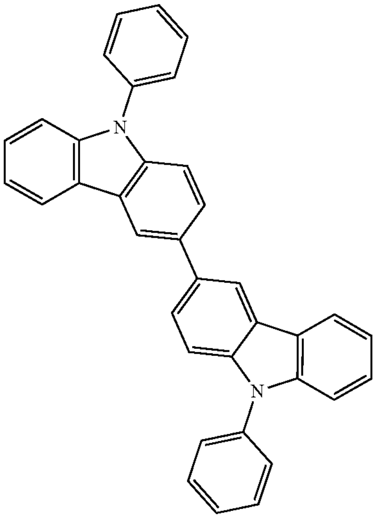
2-132
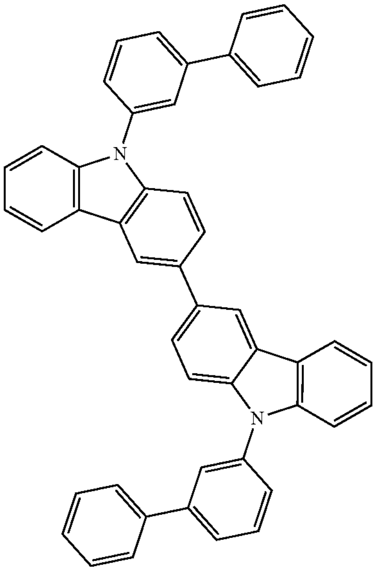

-continued
2-133
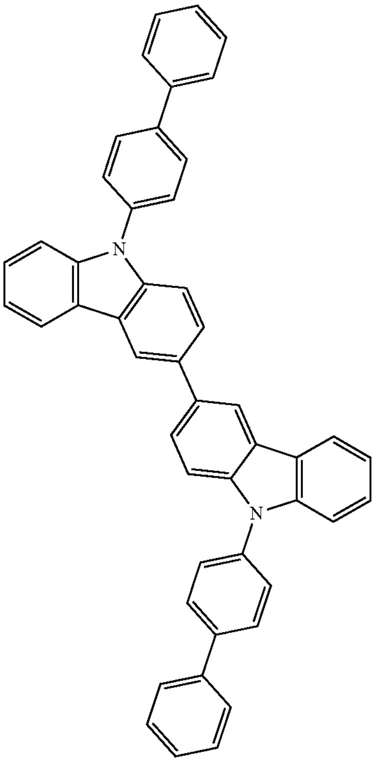
[C19]
2-34
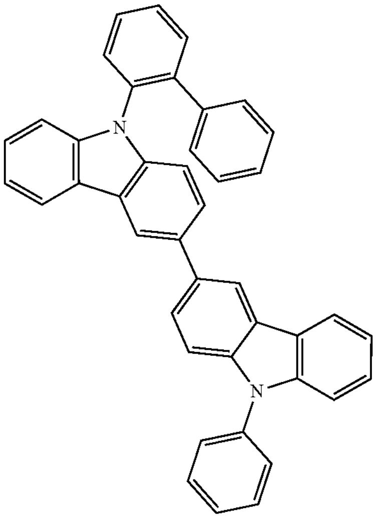
-continued
2-35
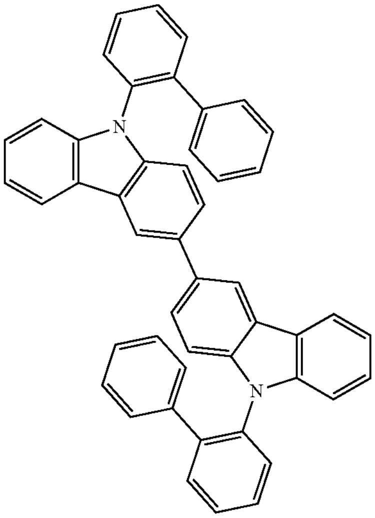
2-36
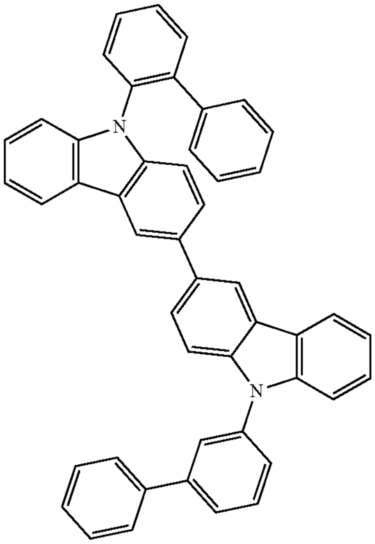

-continued
2-37
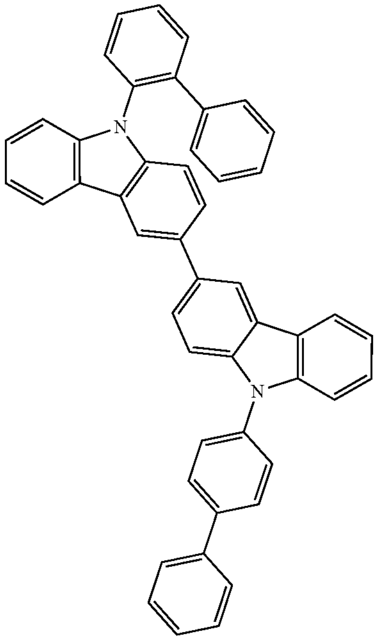
2-38
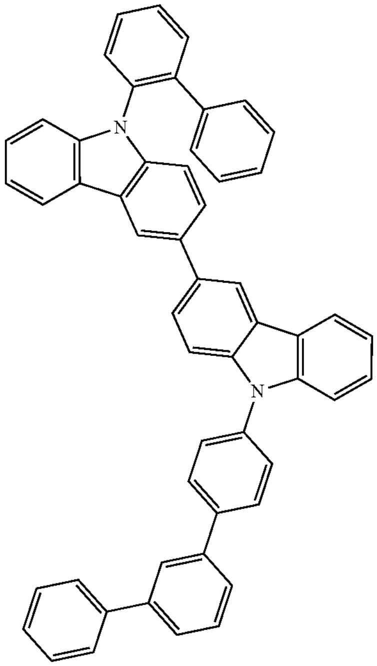
2-39
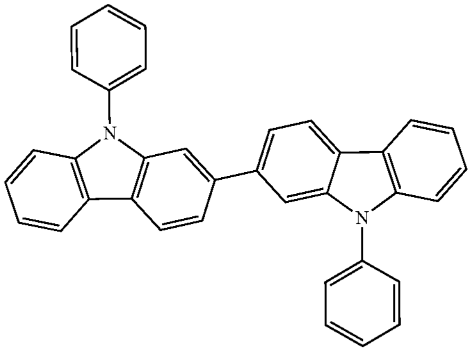
-continued
2-40
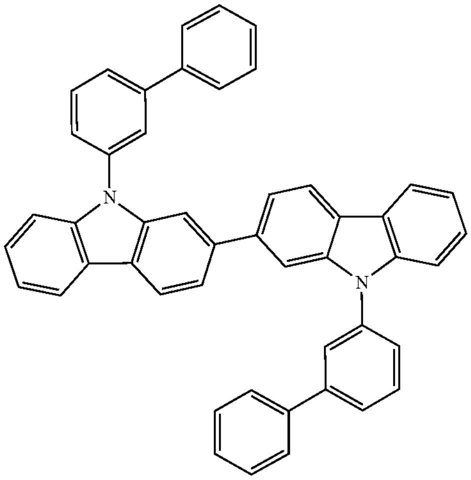
2-41
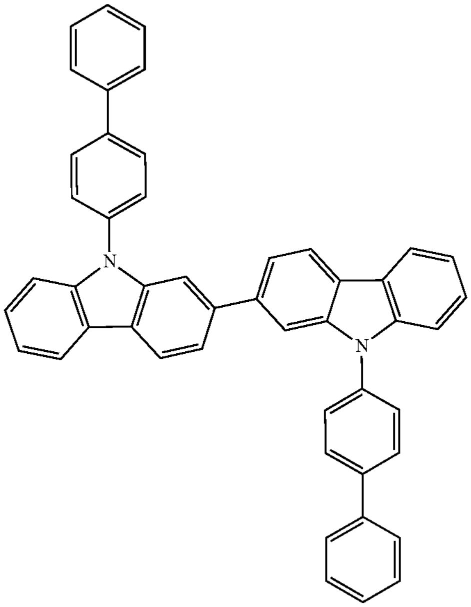
2-42
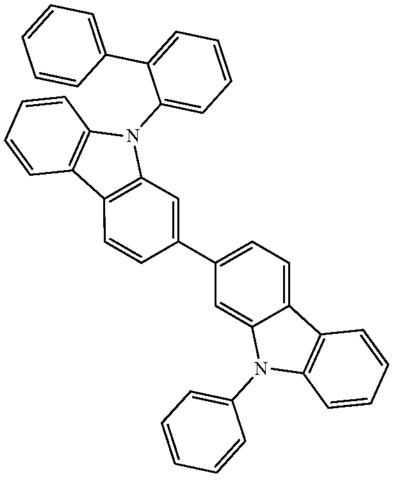

-continued 2-43

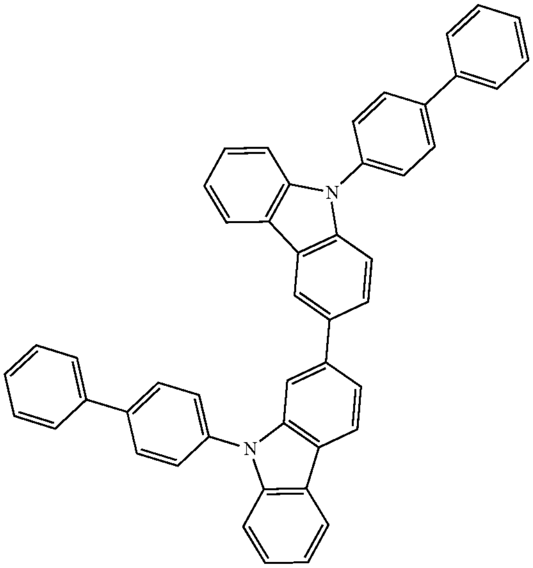

2-44

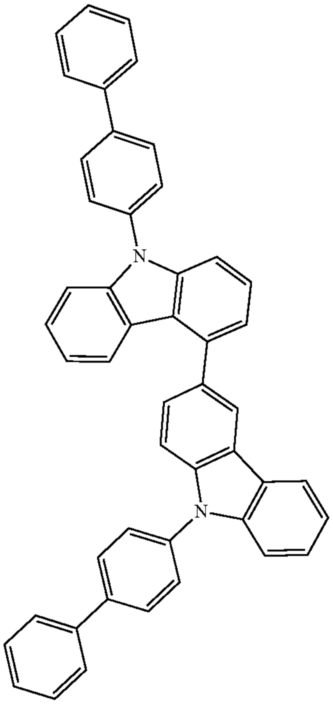

-continued 2-45

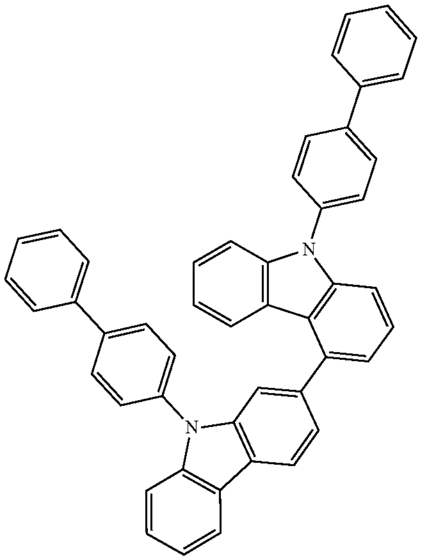

Next, the general formula (3) will be described.

In the general formula (3), the ring C is a heterocycle represented by formula (3a) and the ring C is fused to an adjacent ring at any position.

$R^{10}$ to $R^{12}$ are independently hydrogen, deuterium, an aliphatic hydrocarbon group having 1 to 10 carbon atoms, an aromatic hydrocarbon group having 6 to 10 carbon atoms or an aromatic heterocyclic group having 3 to 12 carbon atoms. Preferred is an aliphatic hydrocarbon group having 1 to 8 carbon atoms, a phenyl group or an aromatic heterocyclic group having 3 to 9 carbon atoms. More preferred is an aliphatic hydrocarbon group having 1 to 6 carbon atoms, a phenyl group or an aromatic heterocyclic group having 3 to 6 carbon atoms.

Specific examples of the aliphatic hydrocarbon group include methyl, ethyl, propyl, butyl, pentyl, hexyl, heptyl, octyl, nonyl, and decyl. Preferred is an alkyl group having 1 to 4 carbon atoms.

Specific examples of the aromatic hydrocarbon group or aromatic heterocyclic group include aromatic groups generated by removing one H from benzene, naphthalene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, dibenzofuran, dibenzothiophene, dibenzoselenophene, and carbazole. Preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, oxadiazole, thiadiazole, benzotriazine, phthalazine, tetrazole, indole, benzofuran, benzothiophene, benzoxazole, benzothiazole, indazole, benzimidazole, benzotriazole, benzisothiazole, and benzothiadiazole. More preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, and oxadiazole.

$L^6$ is independently a single bond, an aromatic hydrocarbon group having 6 to 10 carbon atoms or an aromatic heterocyclic group having 3 to 12 carbon atoms, or a linked aromatic group in which 2 to 10 thereof are linked to each other. Preferred examples of the aromatic hydrocarbon group or aromatic heterocyclic group are the same as in the case where $R^{10}$ is of these groups except that these groups are a divalent group.

$Ar^1$ is an aromatic hydrocarbon group having 6 to 10 carbon atoms or an aromatic heterocyclic group having 3 to 12 carbon atoms. Preferred examples of the aromatic hydrocarbon group or aromatic heterocyclic group are the same as in the case where $R^{10}$ is of these groups except that these groups are a divalent group.

f, g and h each independently represent an integer of 0 to 3.

The compound represented by the general formula (3) is preferably the compound represented by the formula (7) or (8).

In formula (7) or (8), ring B, $R^{10}$ to $R^{13}$, $Ar^1$, x and y are as defined for the general formula (3).

Specific examples of the indolocarbazole compound represented by the general formula (3) are described below, but the compound is not limited thereto.

[C20]

3-1

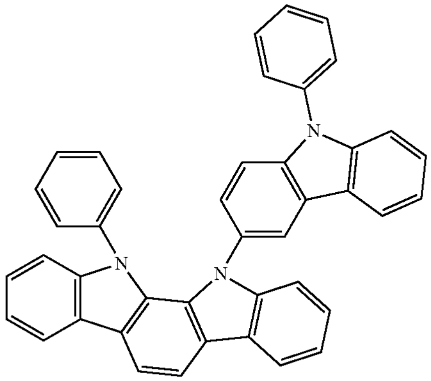

3-2

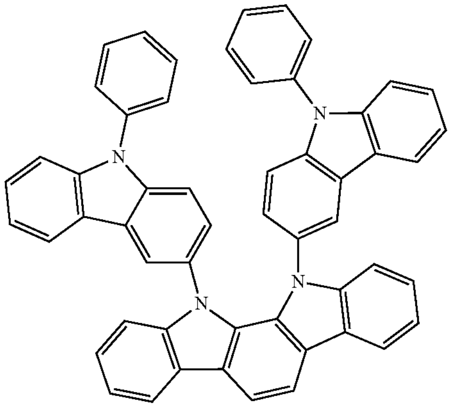

-continued 3-3

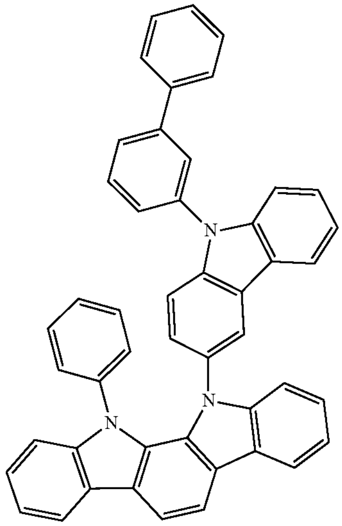

3-4

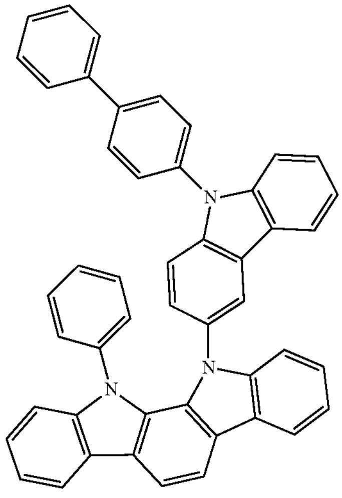

3-5

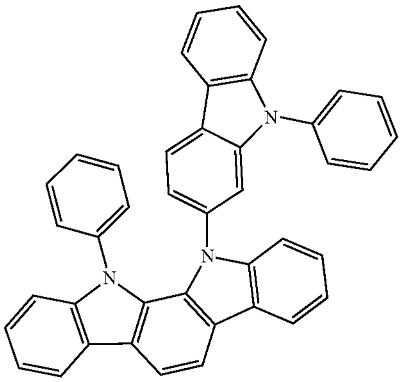

-continued
3-6
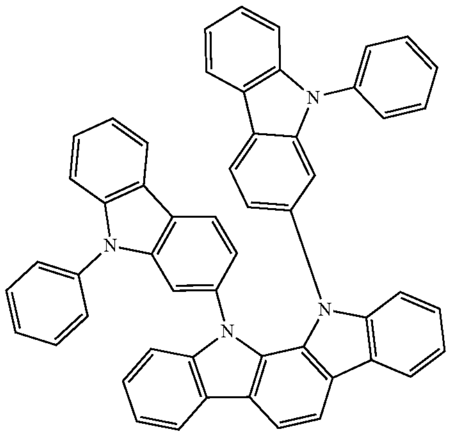
3-7
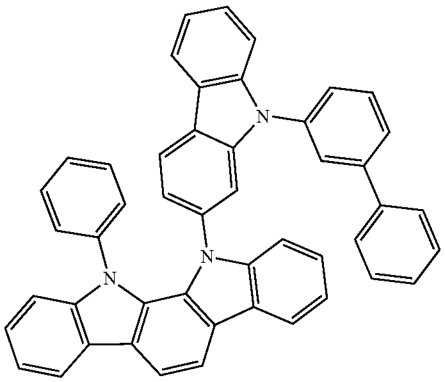
3-8
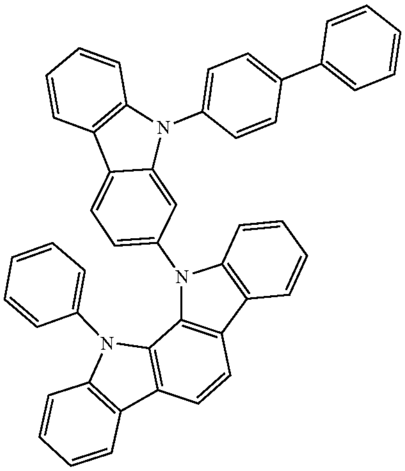
-continued
3-9
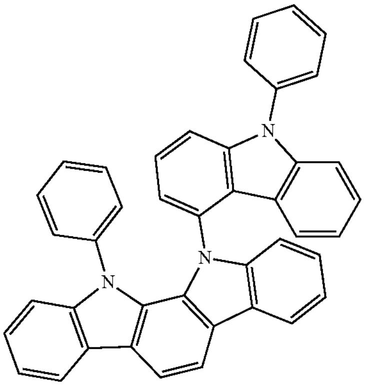
3-10
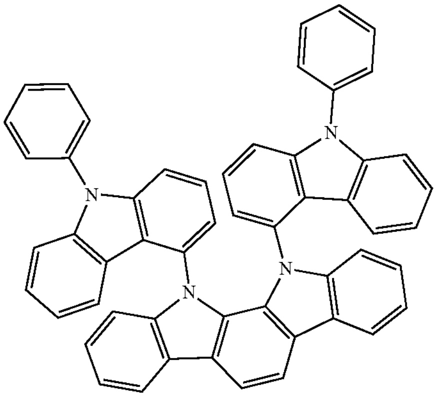
3-11
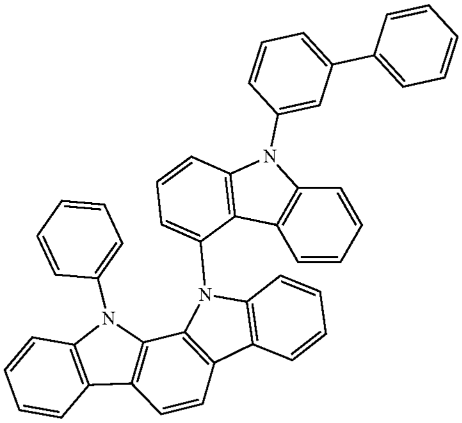

-continued
3-12
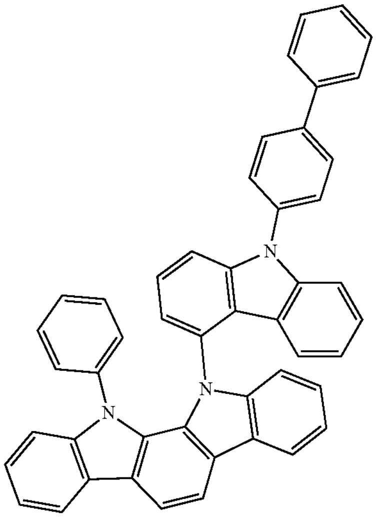
3-13
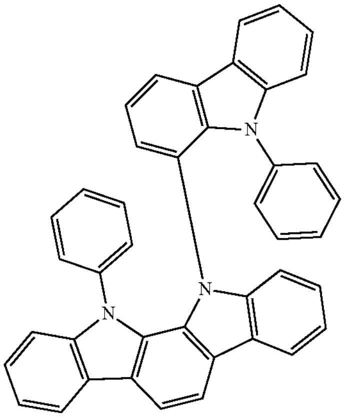
3-14
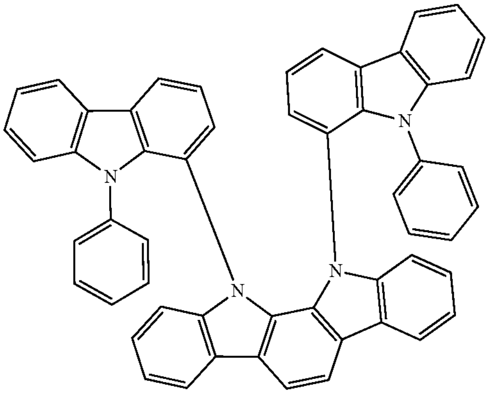
-continued
3-15
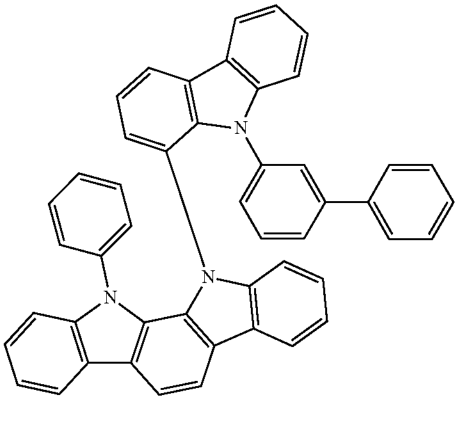
3-16
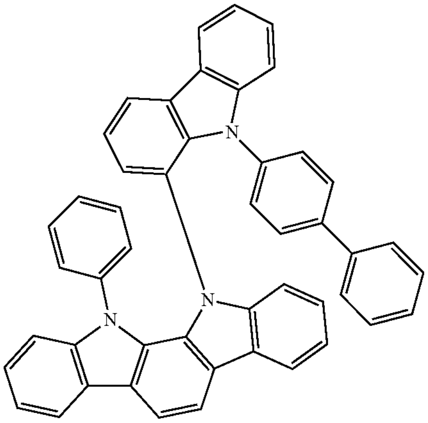
3-17
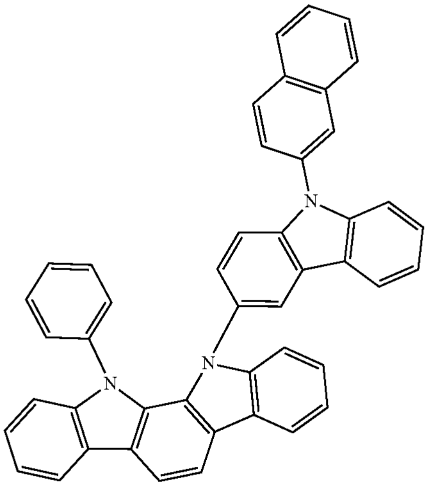

-continued
3-18
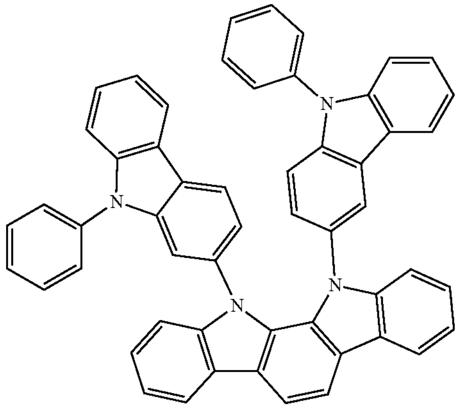
3-19
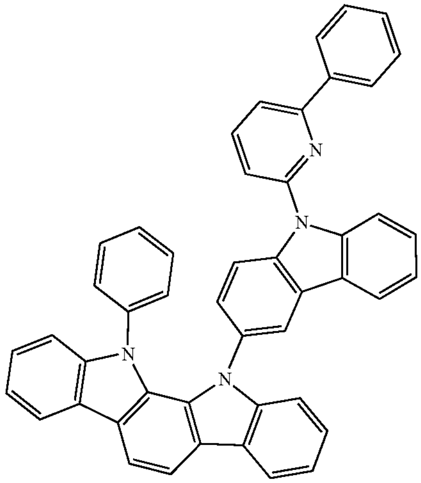
3-20
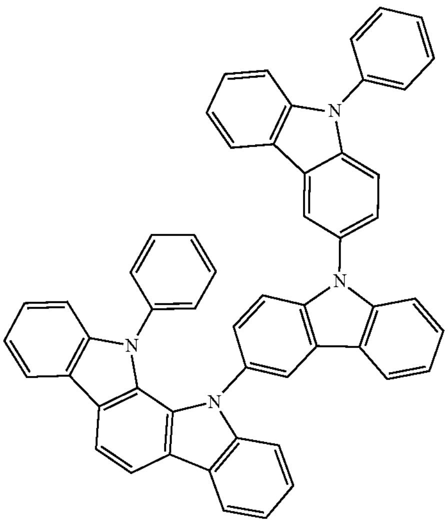
-continued
[C21]
3-21
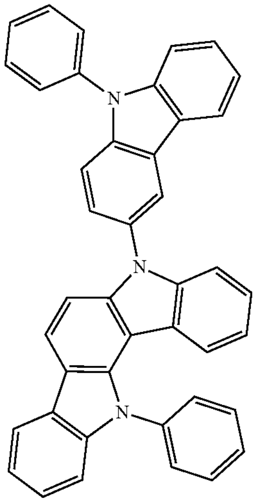
3-22
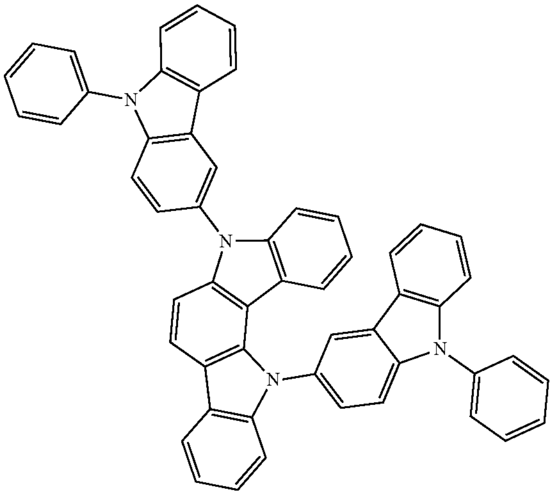
3-23
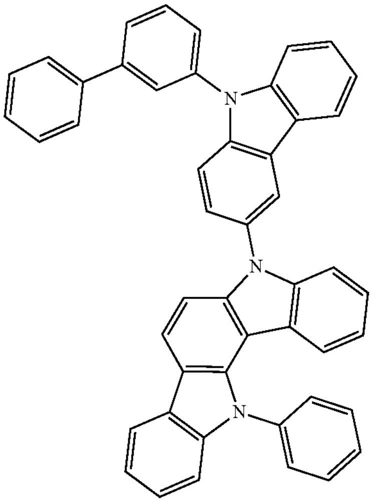

-continued
3-24
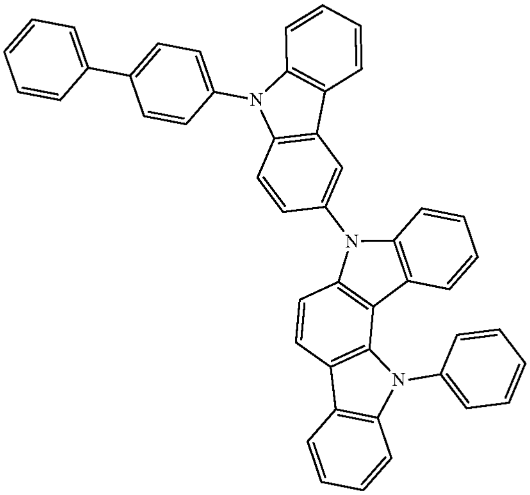
3-25
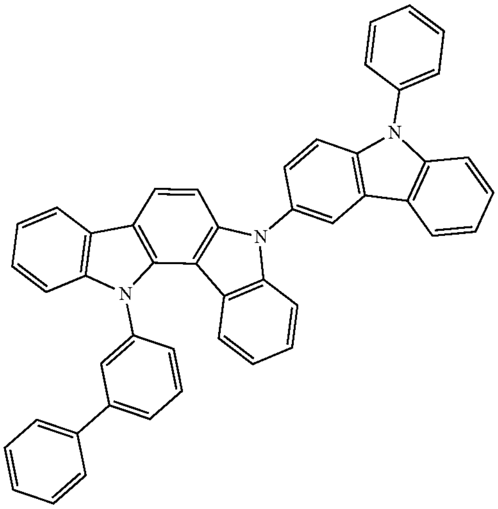
3-26
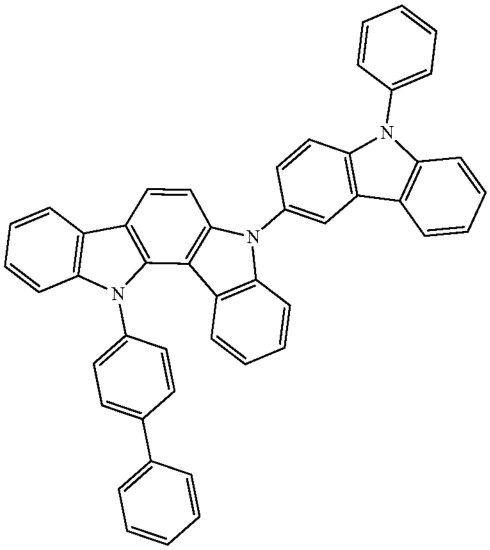
-continued
3-27
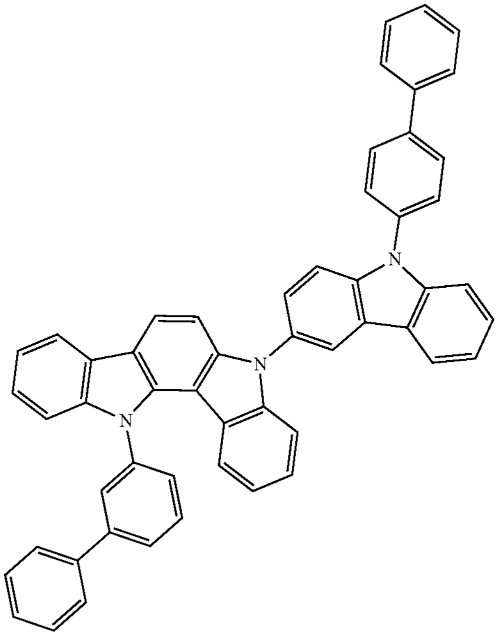
3-28
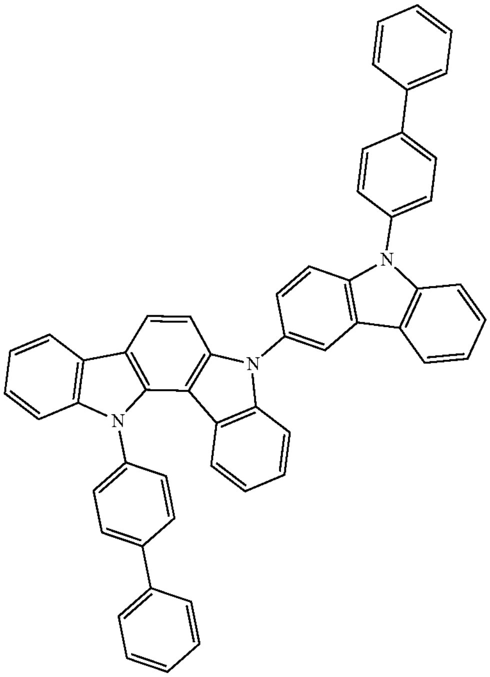

-continued
3-29
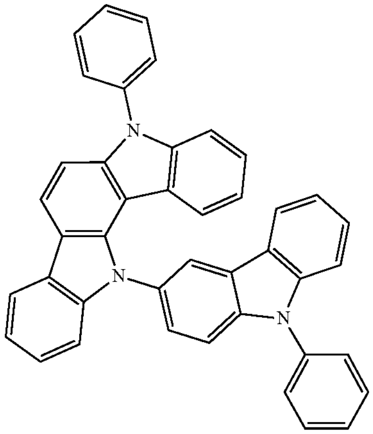
3-30
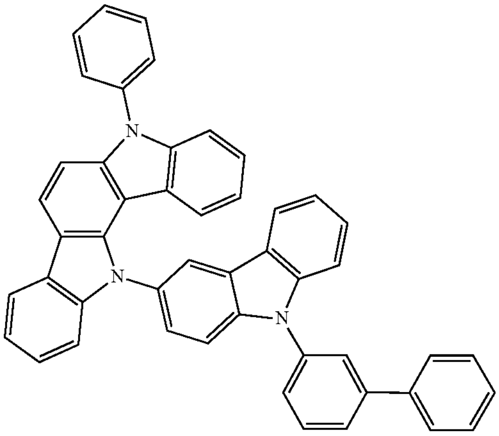
3-31
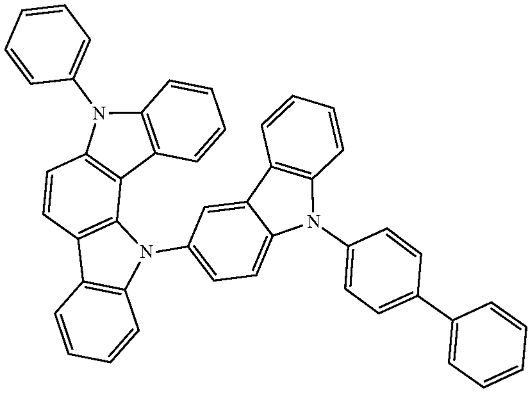
-continued
3-32
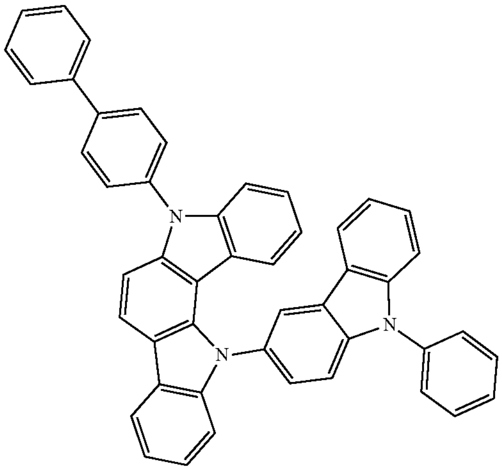
3-33
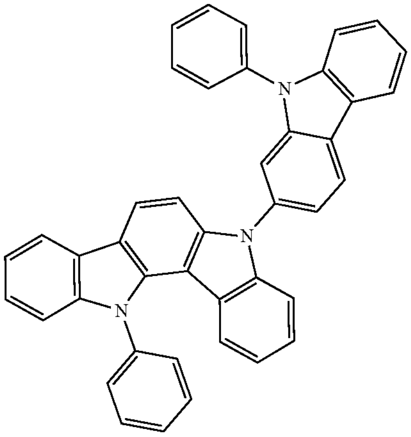
3-34
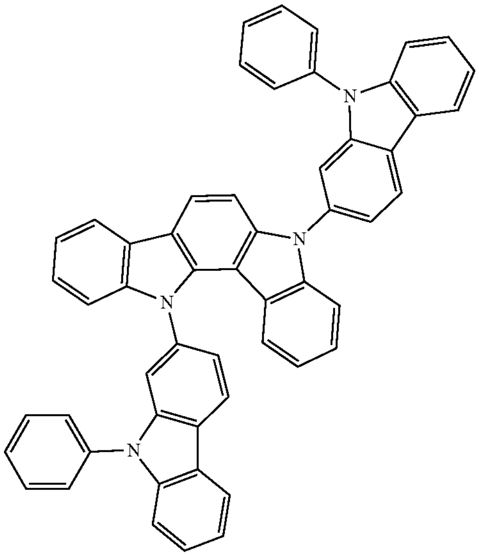

-continued
3-35
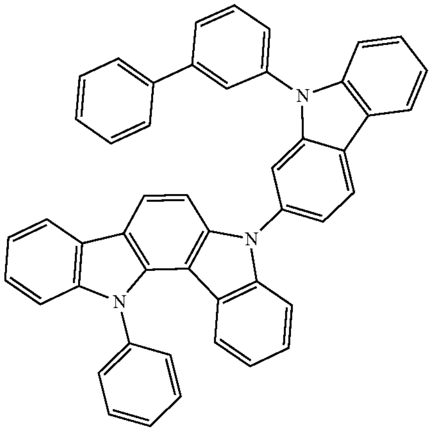
3-36
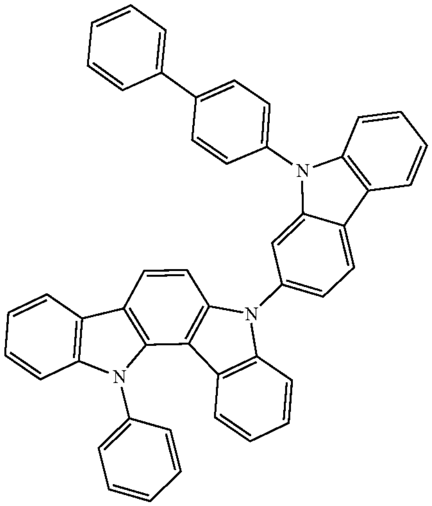
3-37
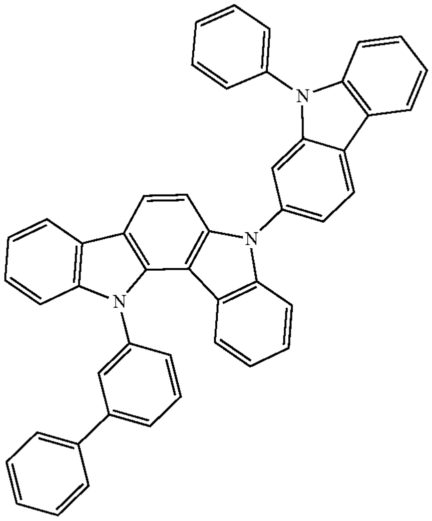
-continued
3-38
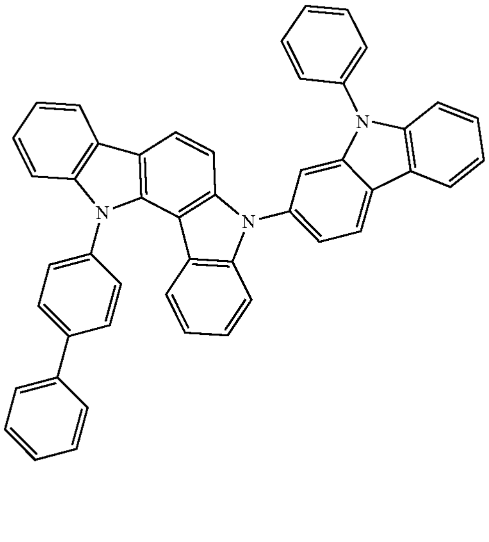
3-39
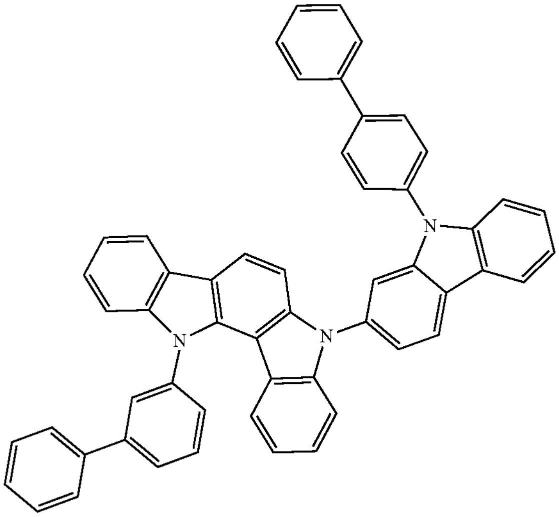
3-40
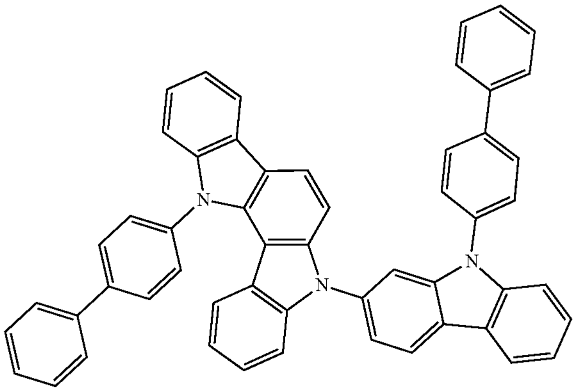

-continued
[C22]
3-41
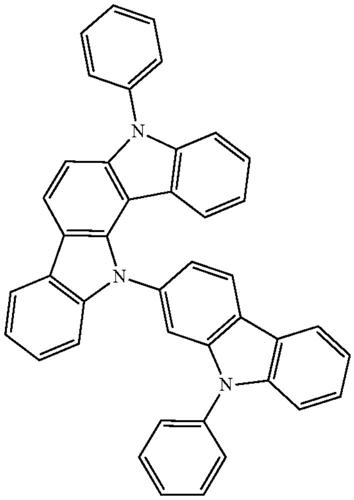
3-42
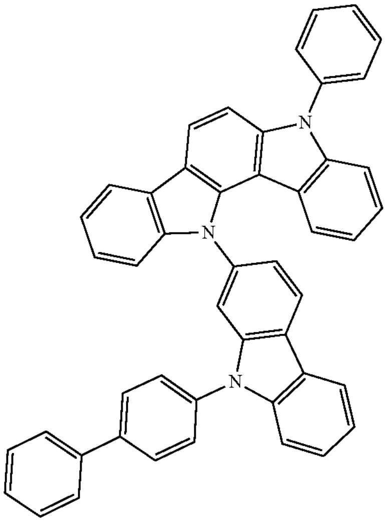
3-43
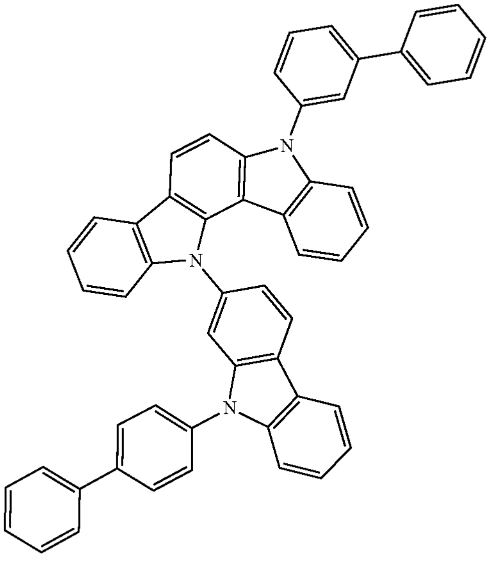
-continued
3-44
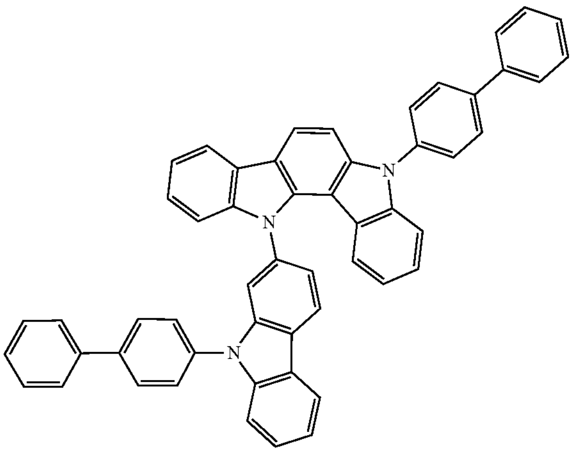
3-45
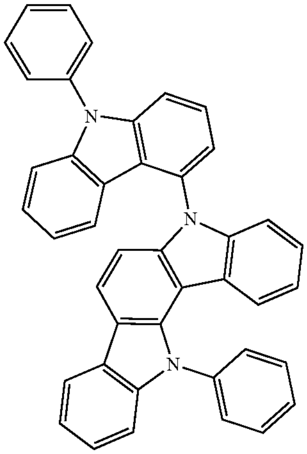
3-46
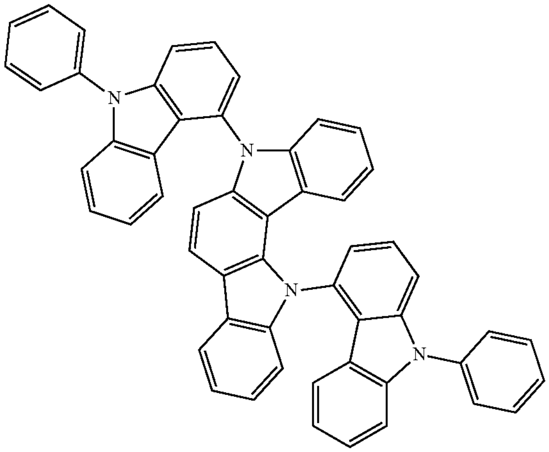

-continued
3-47
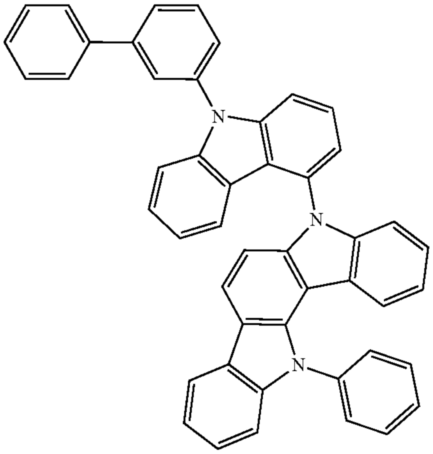
3-48
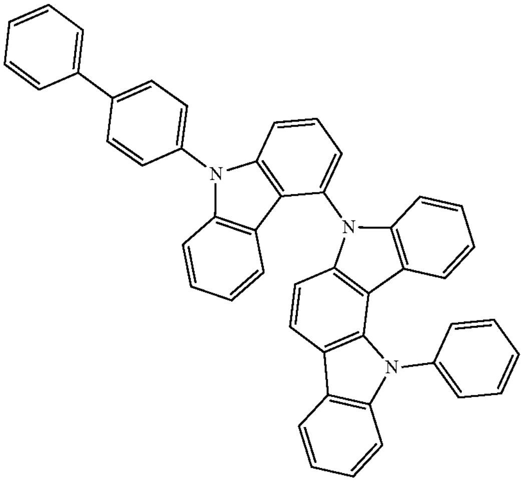
3-49
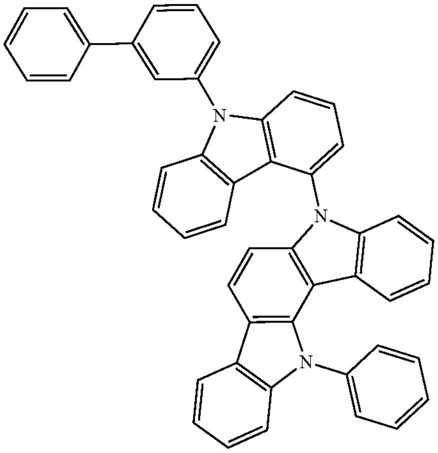
-continued
3-50
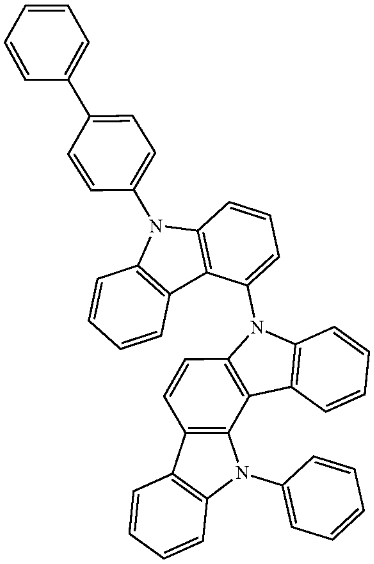
3-51
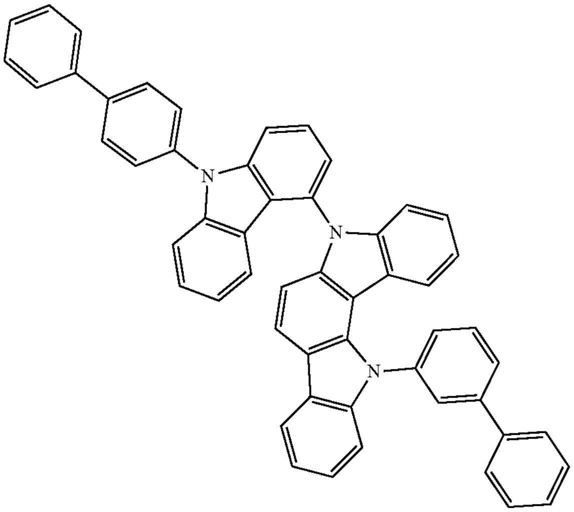
3-52
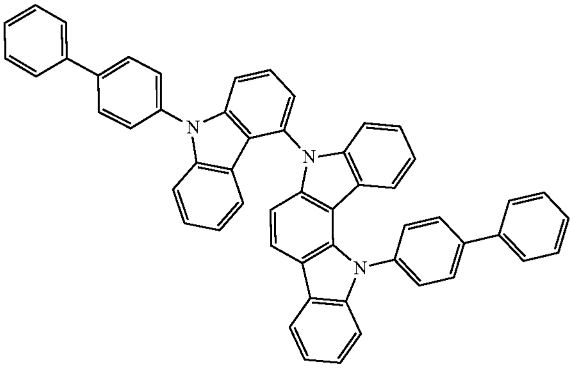

-continued
3-53
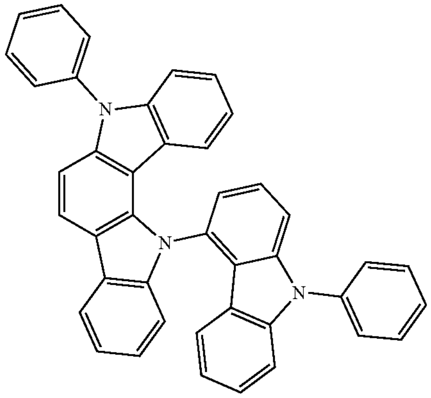
3-54
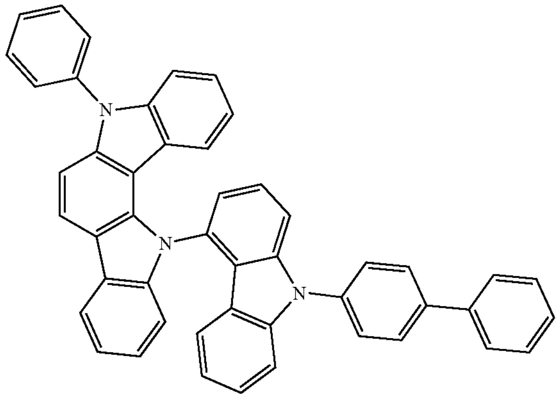
3-55
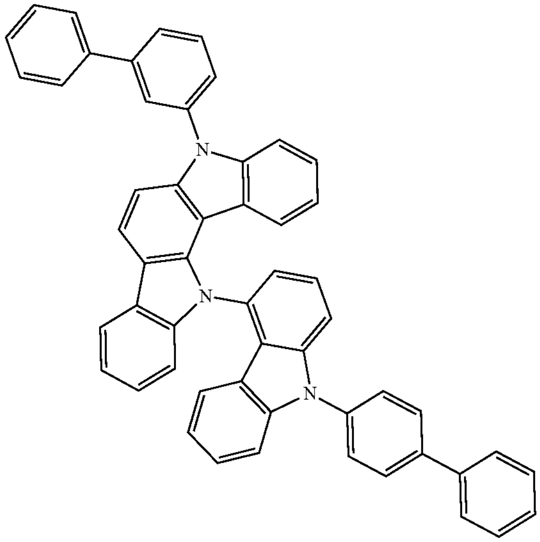
-continued
3-56
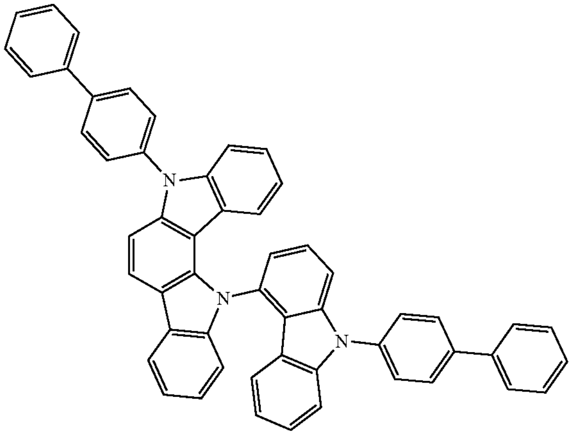
3-57
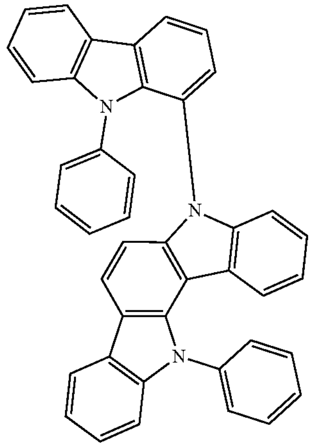
3-58
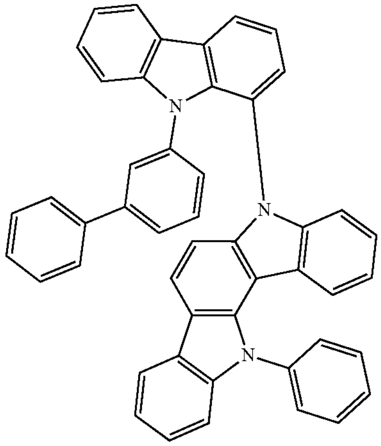

3-59
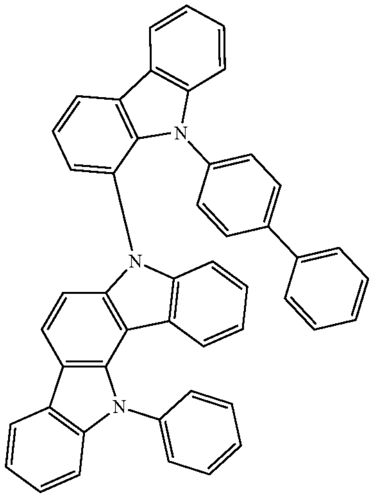
3-60
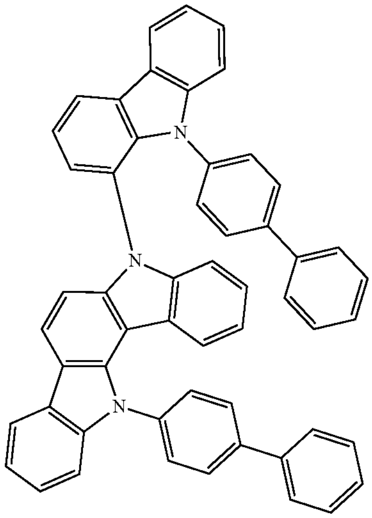
[C23]
3-61
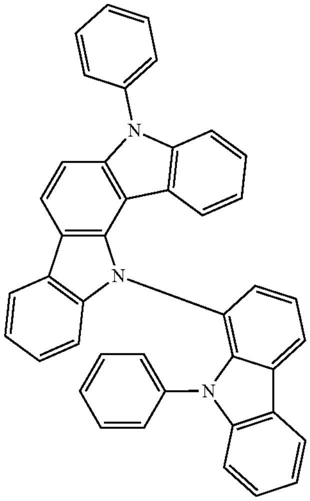
3-62
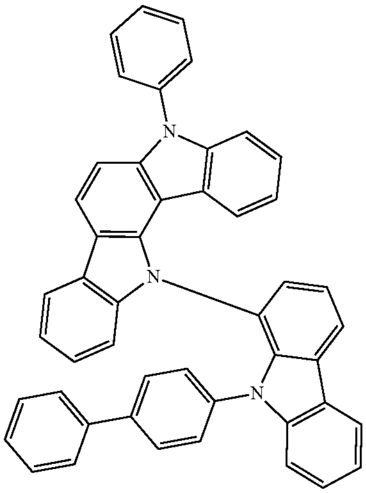
3-63
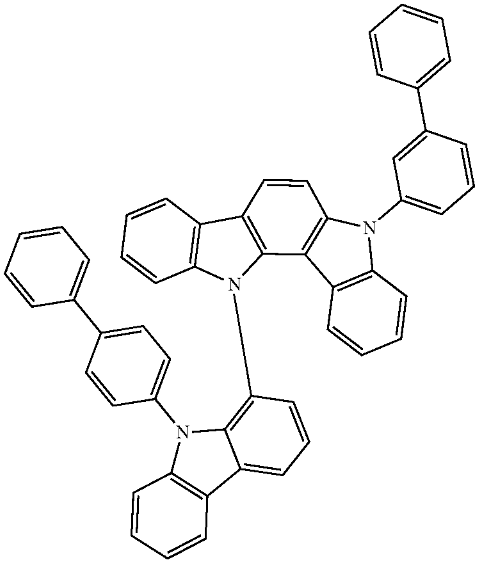
3-64
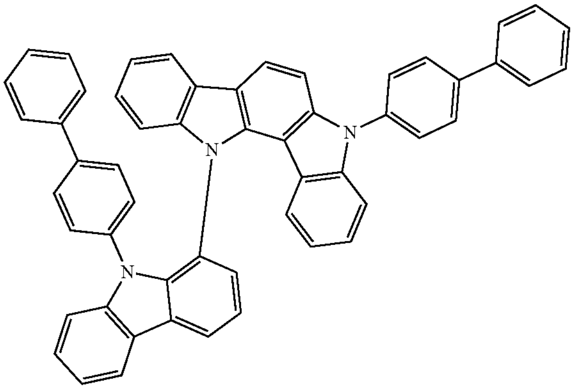

-continued
3-65
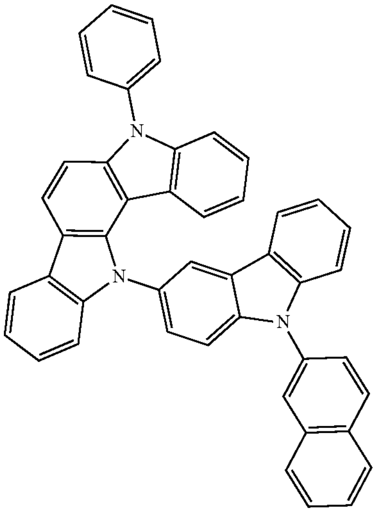
3-66
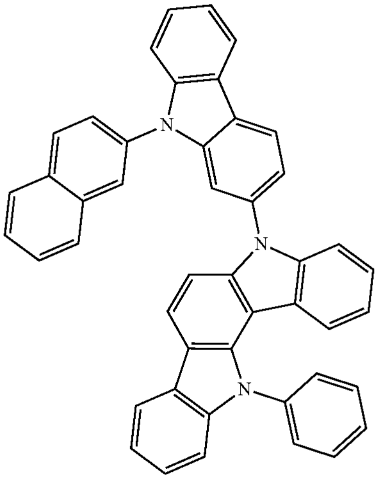
3-67
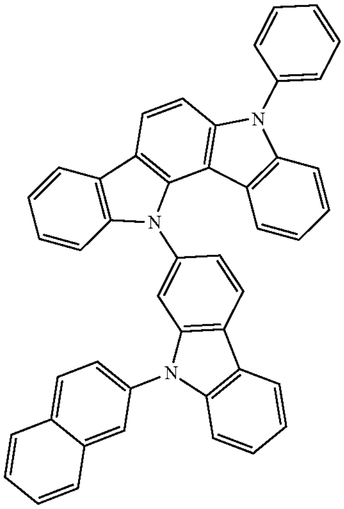
-continued
3-68
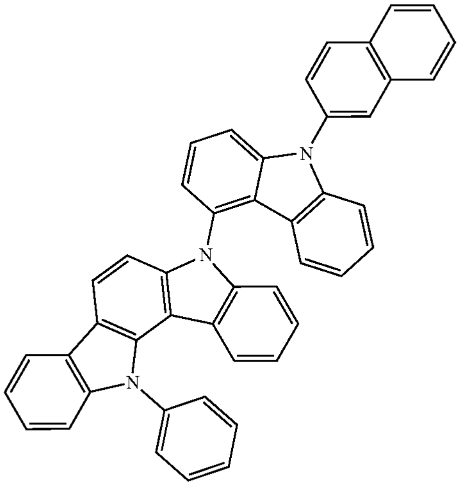
3-69
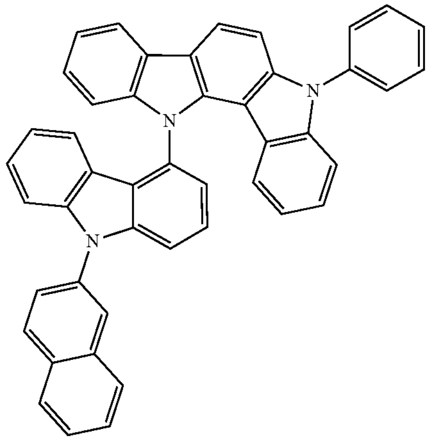
3-70
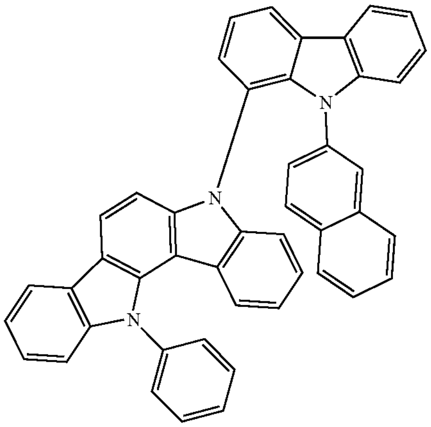

-continued
3-71
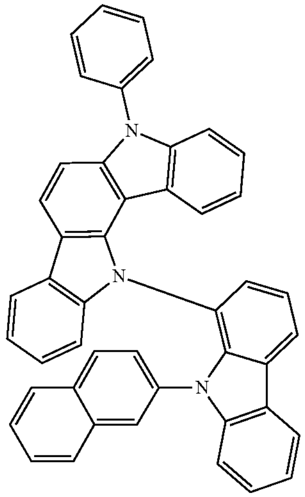
3-72
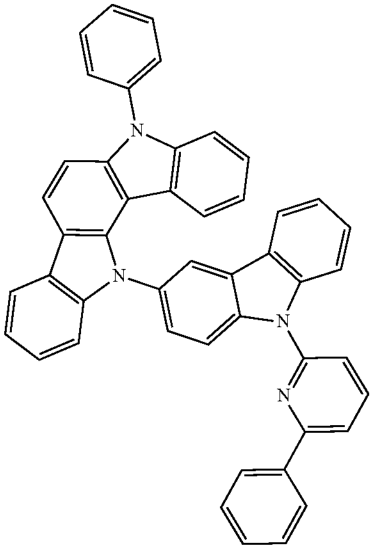
3-73
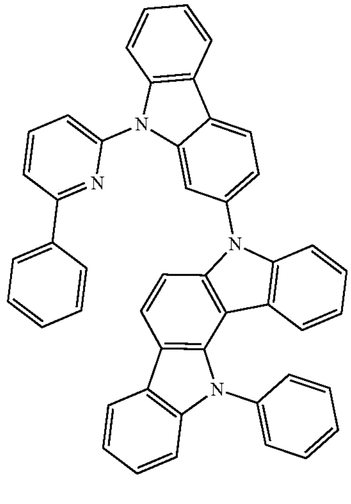
-continued
3-74
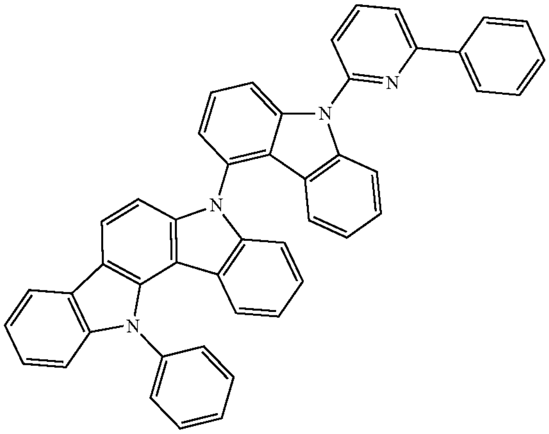
3-75
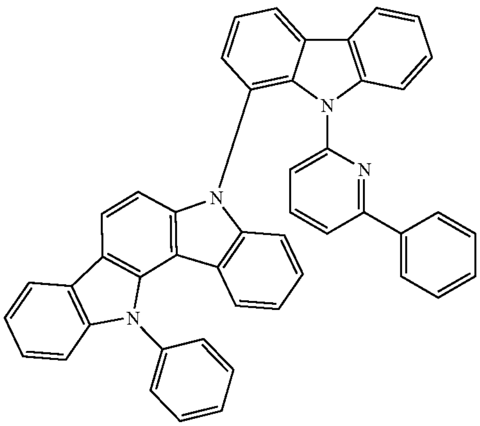
3-76
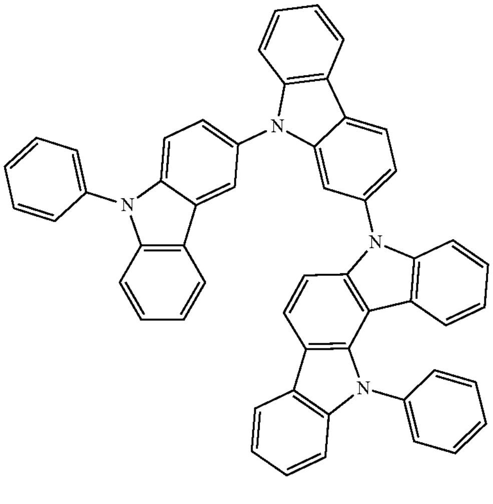

-continued 3-77

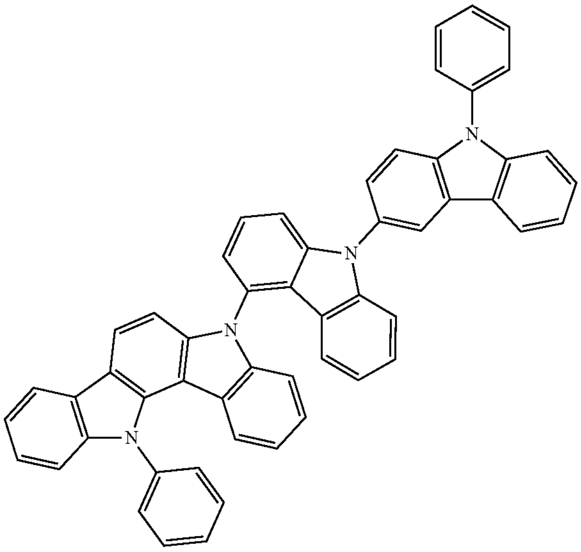

3-78

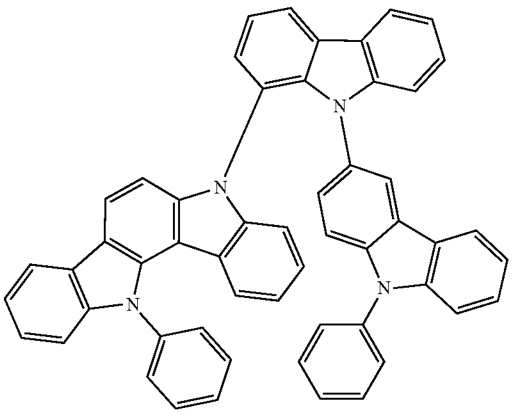

3-79

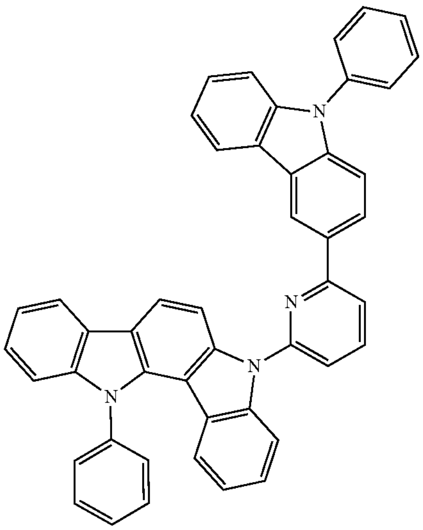

-continued 3-80

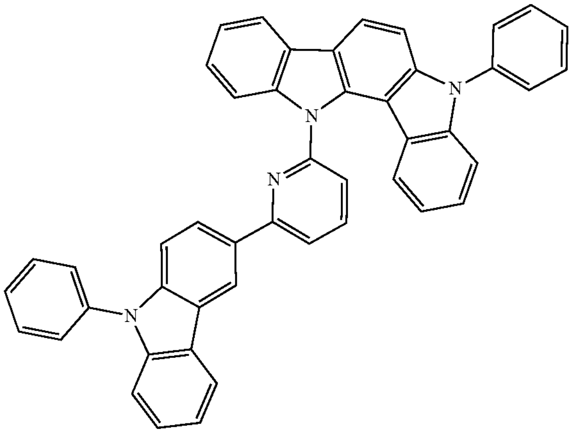

Next, the general formula (4) will be described.

In the general formula (4), $L^7$ represents an aromatic hydrocarbon group having 6 to 30 carbon atoms or an aromatic heterocyclic group having 3 to 30 carbon atoms, or a linked aromatic group in which these aromatic rings are linked. The linked aromatic group is a group having a structure wherein 2 to 10 of aromatic rings of the aromatic hydrocarbon group or aromatic heterocyclic group are linked by a single bond.

$L^7$ is a group of m-valence, in which an aromatic hydrocarbon group, an aromatic heterocyclic group or a linked aromatic group may have a substituent.

In the above, $L^7$ is not a group containing a carbazole ring.

Specific examples of the aromatic hydrocarbon group or the aromatic heterocyclic group include groups generated by removing m H atoms from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, indolizine, indole, isoindole, indazole, purine, quinolizine, isoquinoline, imidazole, naphthyridine, phthalazine, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisooxazole, benzisothiazole, and aromatic compounds in which a plurality of these aromatic rings is linked, and others.

In the case of the linked aromatic group, the number of linked rings is preferably 2 to 10, more preferably 2 to 7; and aromatic rings to be linked may be the same or different. In that case, in formula (3), the binding position which m carbazolyl groups bind to is not limited, and it may be either a ring at an end of linked aromatic rings and a ring at a center thereof. The aromatic ring herein collectively refers to an aromatic hydrocarbon ring and an aromatic heterocyclic ring.

Specific examples of the linked aromatic group include groups generated by removing hydrogen from biphenyl, terphenyl, quaterphenyl, binaphthalene, phenyltriphenylene, phenyldibenzofuran, phenyldibenzothiophene, bisdibenzofuran, bisdibenzothiophene, and others.

Specific examples of preferred $L^7$ include groups generated from benzene, naphthalene, anthracene, biphenyl, terphenyl, dibenzofuran, dibenzothiophene, phenyldibenzofuran or phenyldibenzothiophene. More preferred examples include groups generated from benzene, biphenyl or terphenyl.

m represents an integer of 1 to 3. Preferably, m is 1 or 2, and more preferably 1.

n is the number of repetitions, and each independently represent an integer of 1 to 4. Preferably, n is 1 to 3. However, at least one n is an integer of 2 to 4.

The general formula (4) preferably has at least one binding structure represented by formula (c1) or formula (c2) therein. It is more preferred that all of the binding structures among carbazolyl groups should be a binding structure represented by formula (c1) or formula (c2).

The sum of n (total number of carbazolyl groups) is an integer of 2 to 12, preferably 2 to 9, and more preferably 2 to 6.

In the general formula (4), formula (c1) and formula (c2), $R^{13}$ each independently represents hydrogen, an alkyl group having 1 to 10 carbon atoms, or a cycloalkyl group having 3 to 11 carbon atoms. Preferred is hydrogen, an alkyl group having 1 to 8 carbon atoms or a cycloalkyl group having 3 to 8 carbon atoms. More preferred is hydrogen, an alkyl group having 1 to 4 carbon atoms, or a cycloalkyl group having 5 to 7 carbon atoms.

Specific examples of the alkyl group include a methyl group, an ethyl group, a propyl group, a butyl group, a pentyl group, a hexyl group, a heptyl group, an octyl group, a nonyl group, and a decyl group. Preferred are a methyl group, an ethyl group, a propyl group, a butyl group, a pentyl group, a hexyl group, a heptyl group, and an octyl group. The alkyl group may be either of a linear chain and a branched chain.

Specific examples of the cycloalkyl group include a cyclopropyl group, a cyclobutyl group, a cyclopentyl group, a cyclohexyl group, a cycloheptyl group, a cyclooctyl group, and a methylcyclohexyl group; and preferred are a cyclohexyl group and a methylcyclohexyl group.

Specific examples of the carbazole compound represented by the general formula (4) are described below, but the compound is not limited thereto.

[C24]

4-1

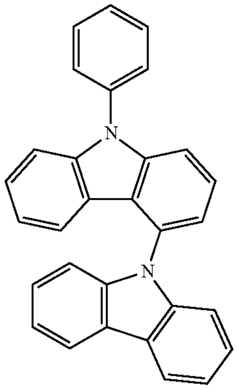

-continued 4-2

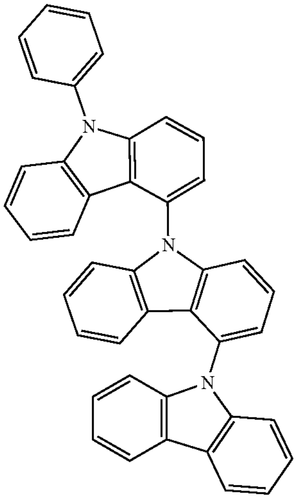

4-3

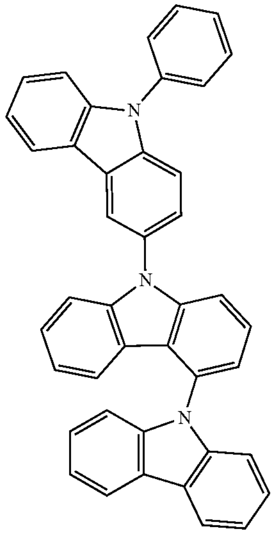

4-4

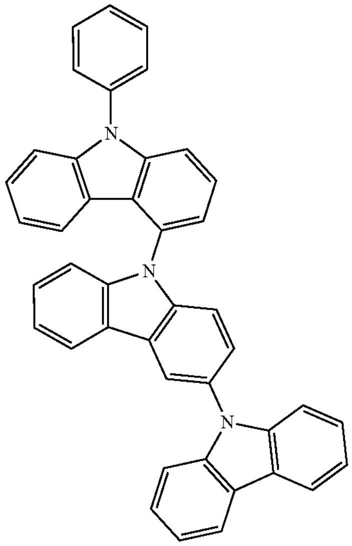

-continued
4-5
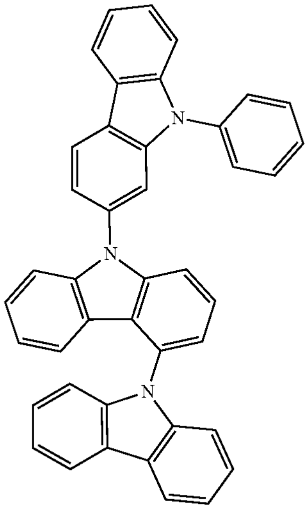
4-6
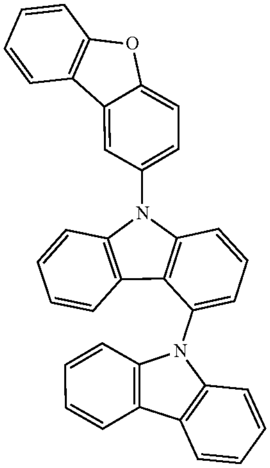
4-7
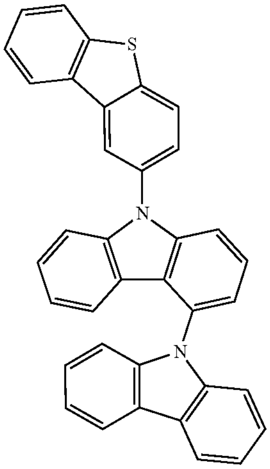
-continued
4-8
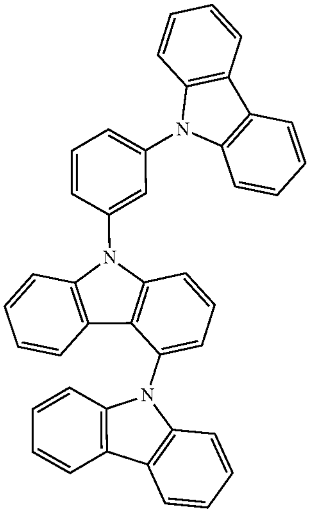
4-9
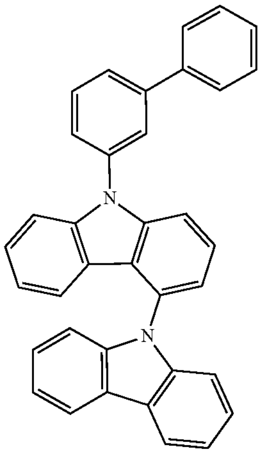
4-10
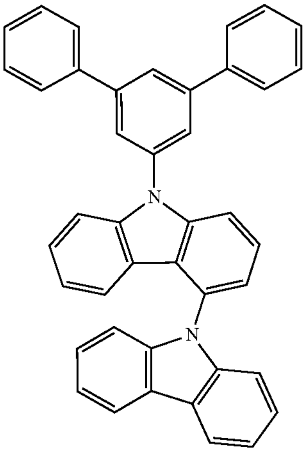

-continued
4-11
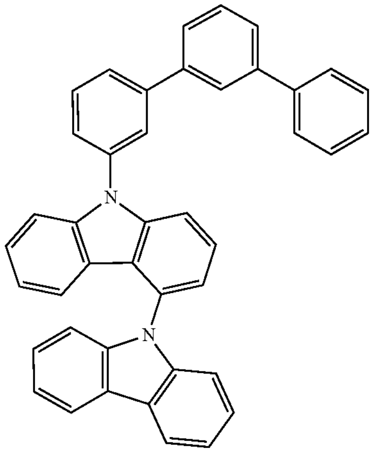
4-12
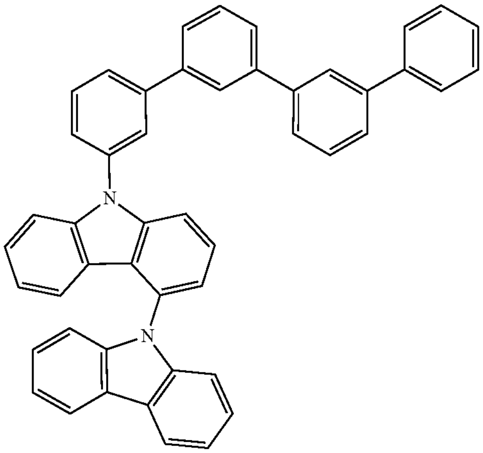
4-13
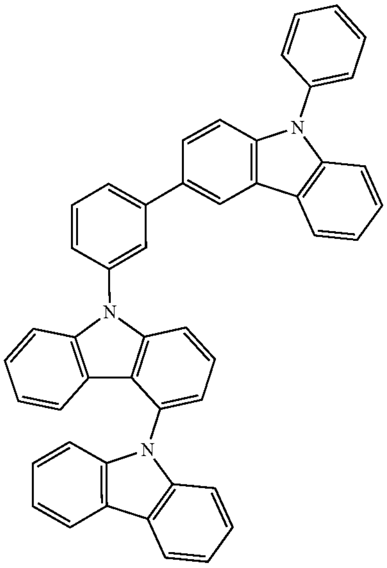
-continued
4-14
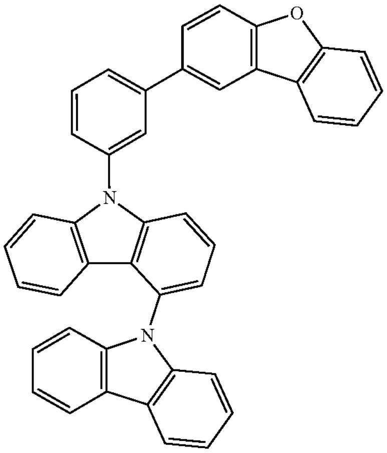
4-15
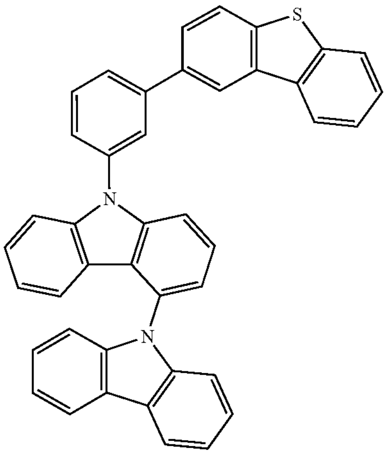
4-16
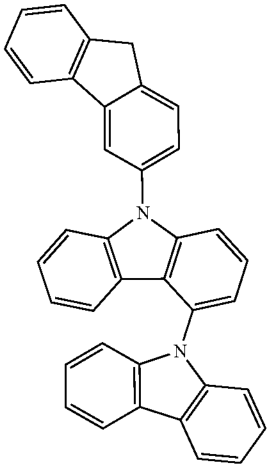

-continued
4-17
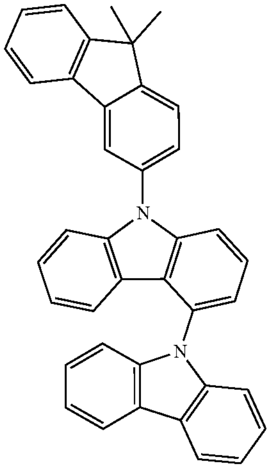
4-18
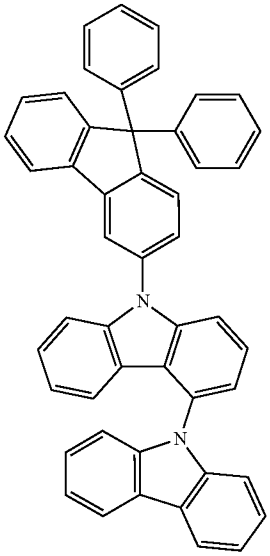
4-19
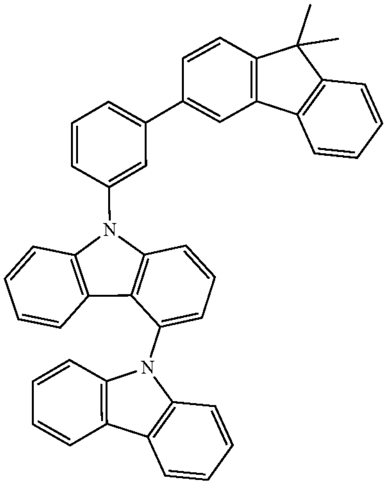
-continued
[C25]
4-119
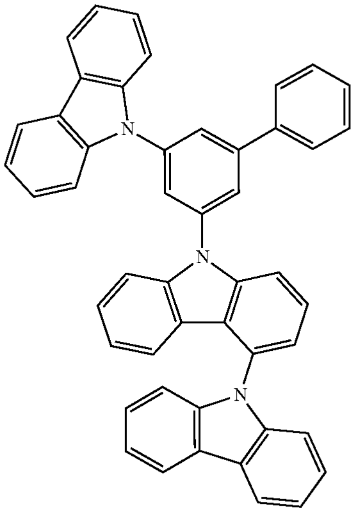
4-20
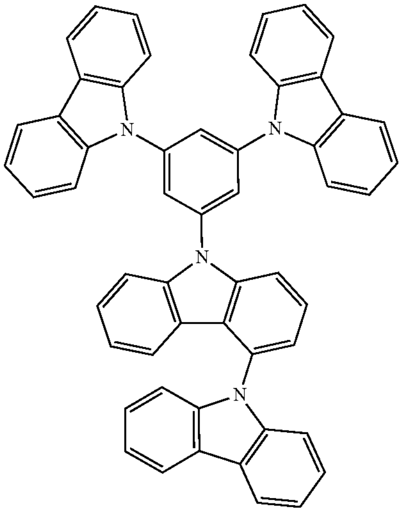
4-21
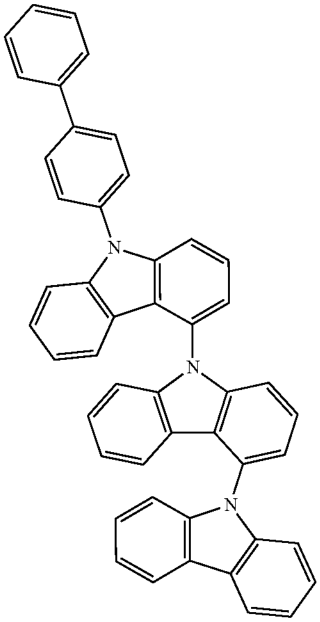

-continued
4-22
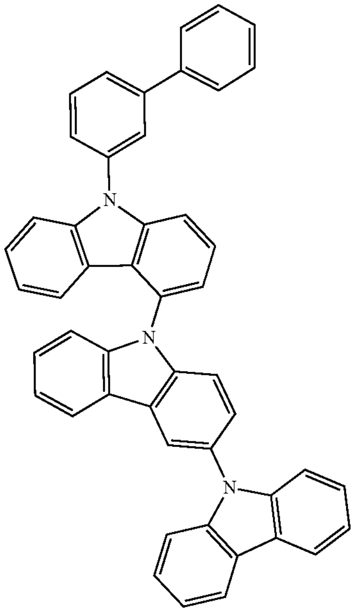
4-23
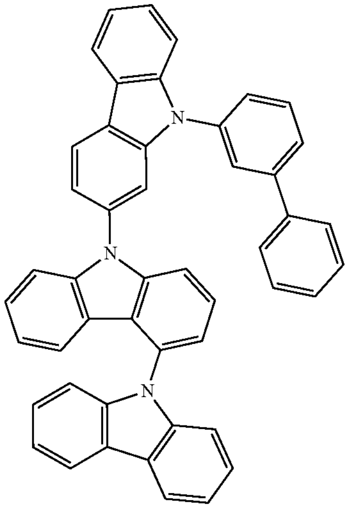
-continued
4-24
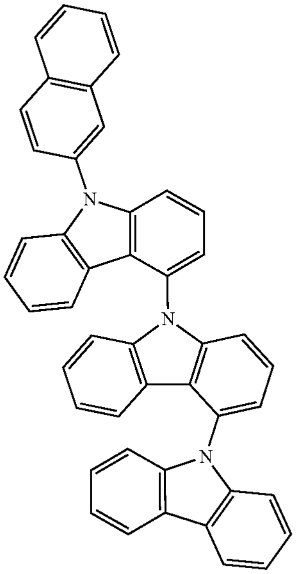
4-25
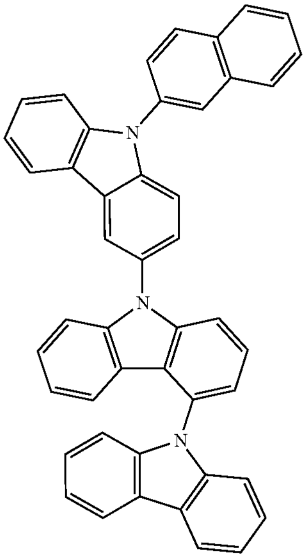

4-26
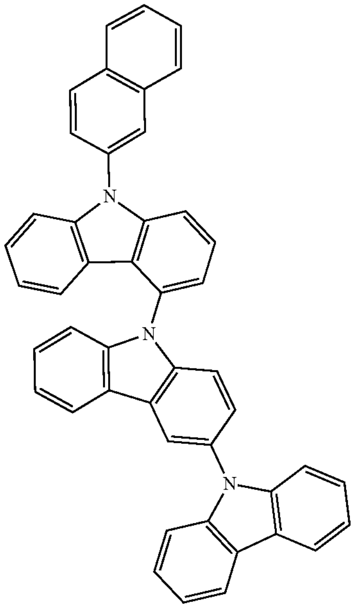
4-27
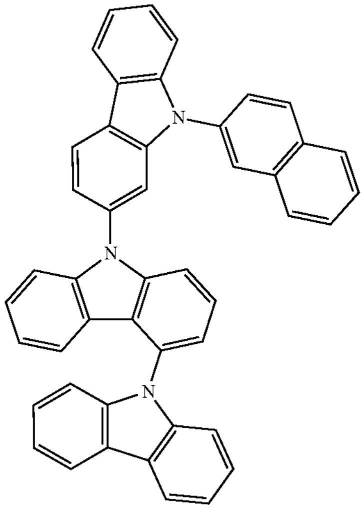
4-28
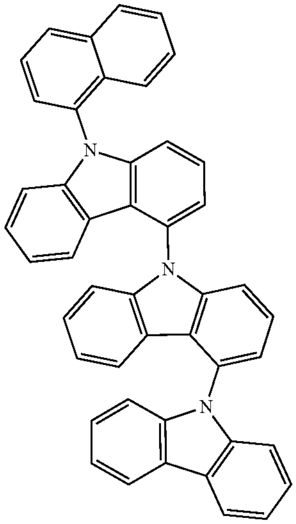
4-29
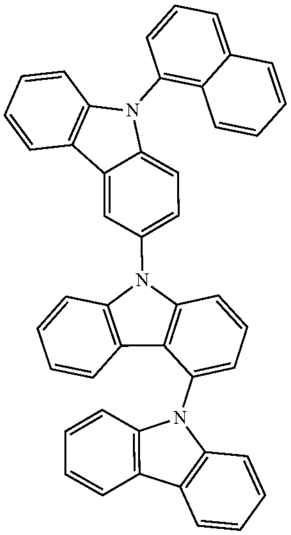
4-30
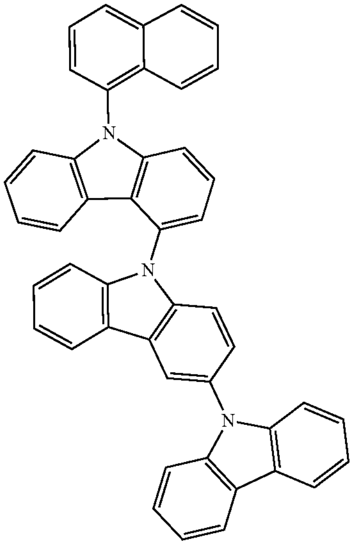
4-31
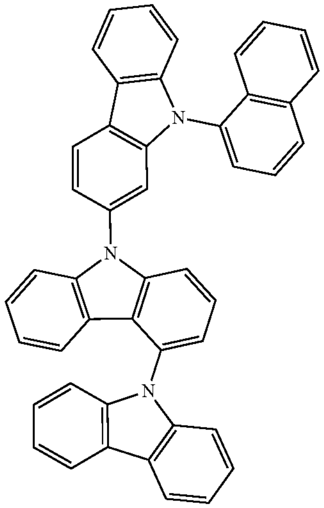

-continued
4-32
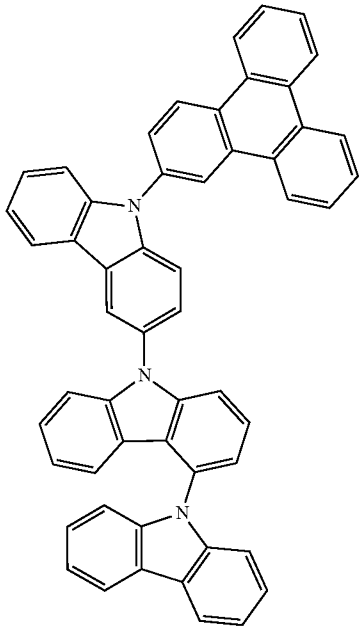
[C26]
4-33
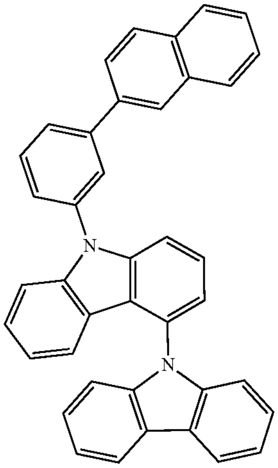
4-34
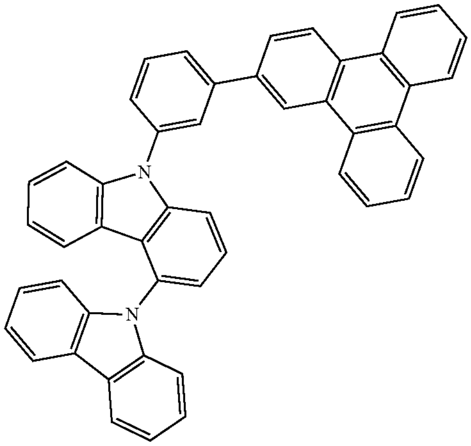
-continued
4-35
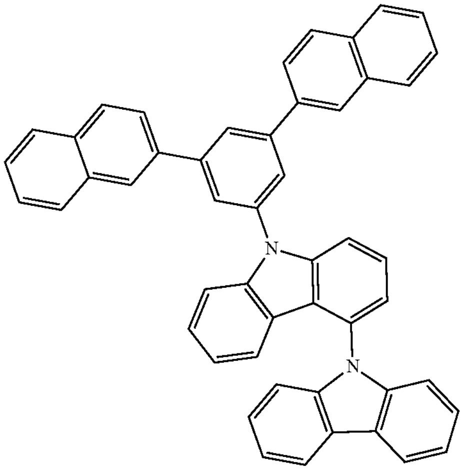
4-36
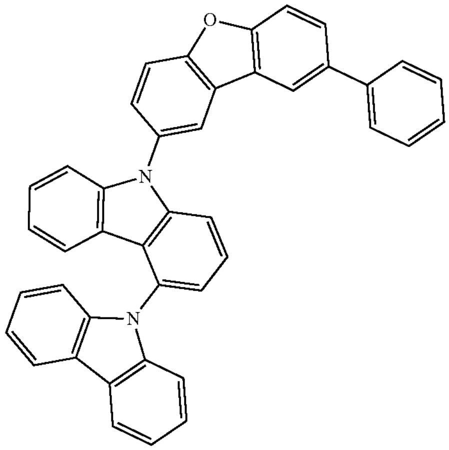
4-37
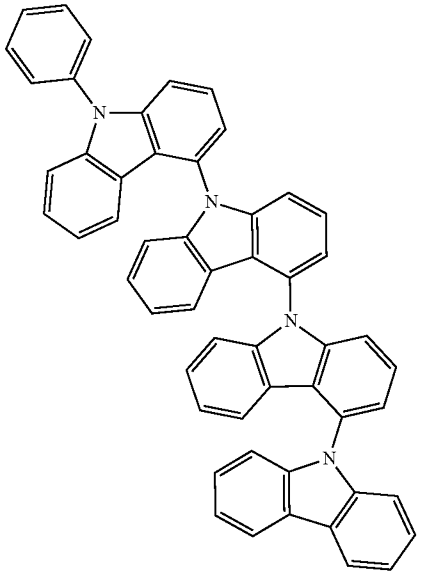

4-38
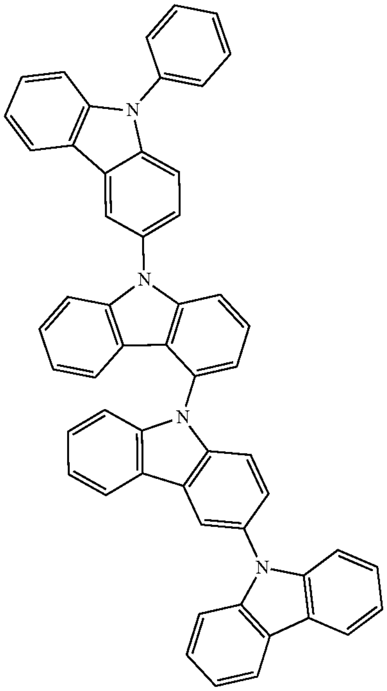
4-39
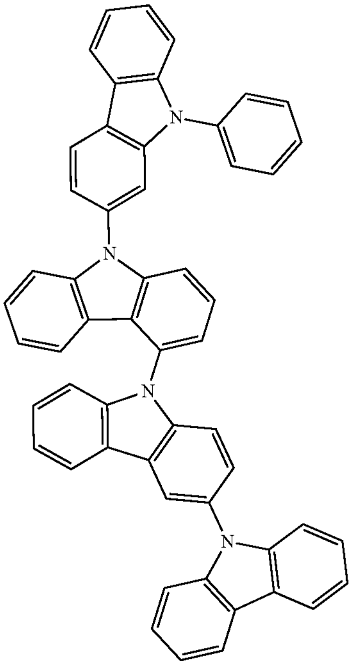
4-40
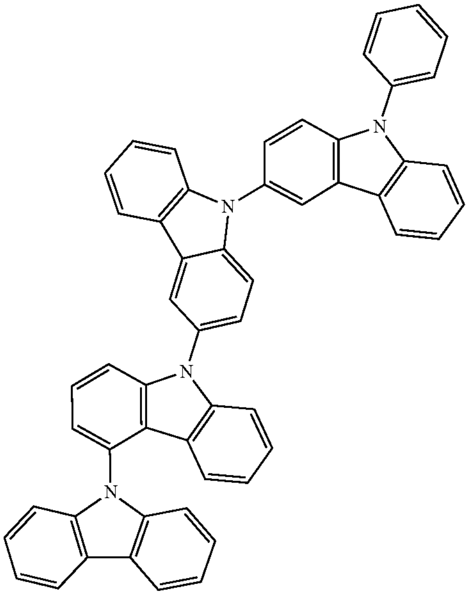
4-41
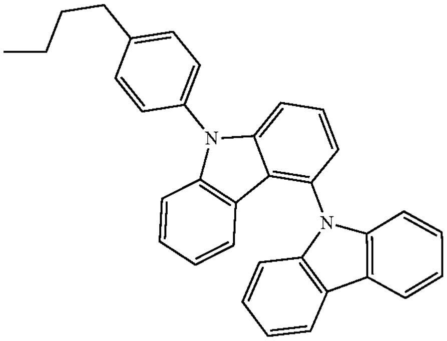
4-42
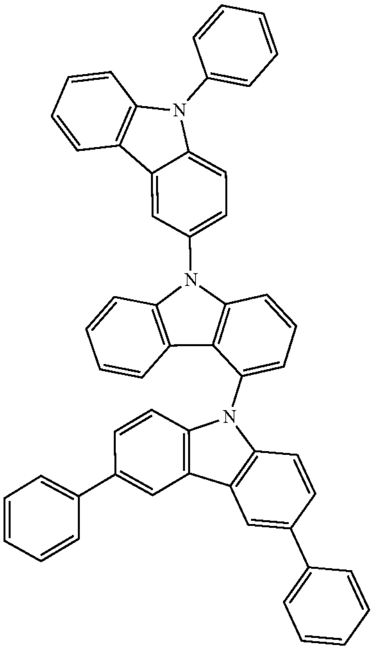

-continued
4-43
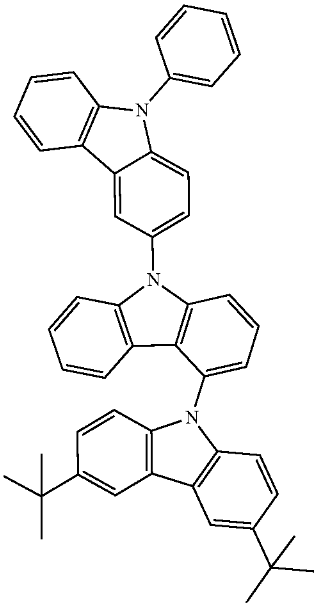
[C27]
4-44
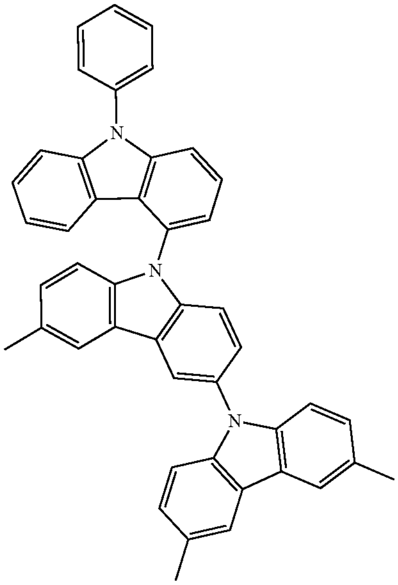
-continued
4-45
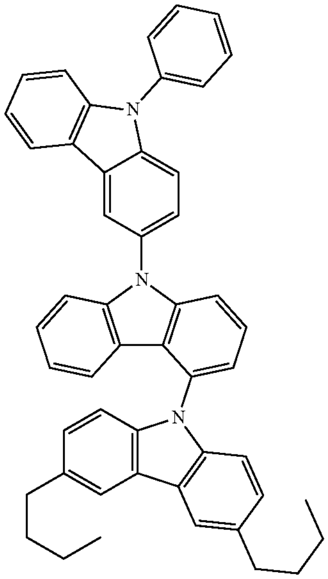
4-46
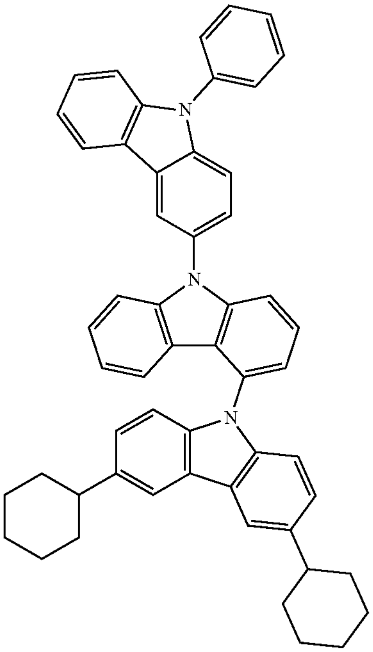

-continued
4-47
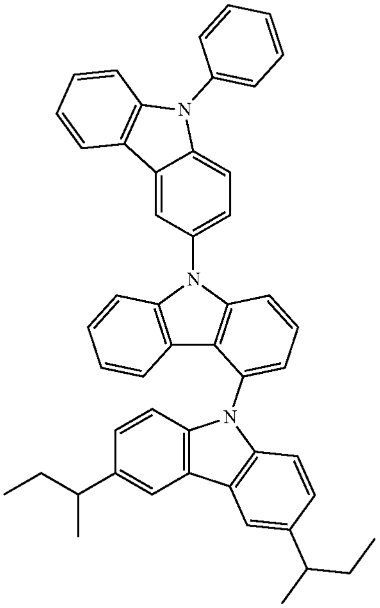
4-48
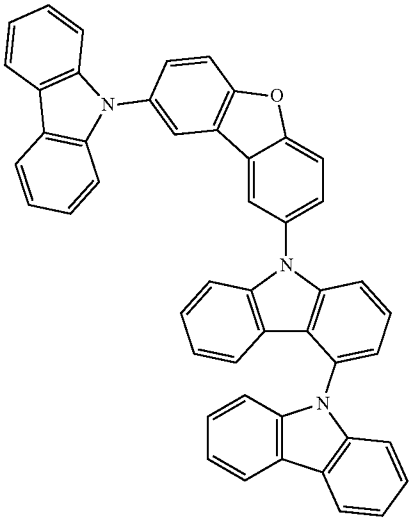
4-49
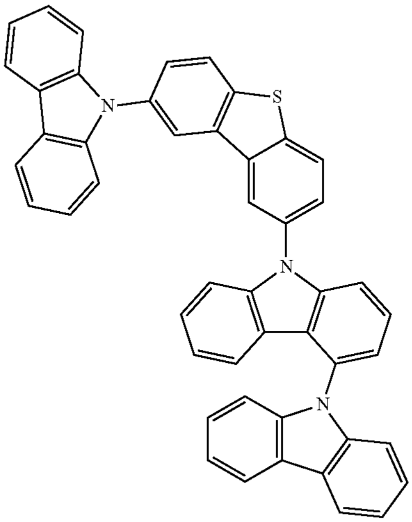
-continued
4-50
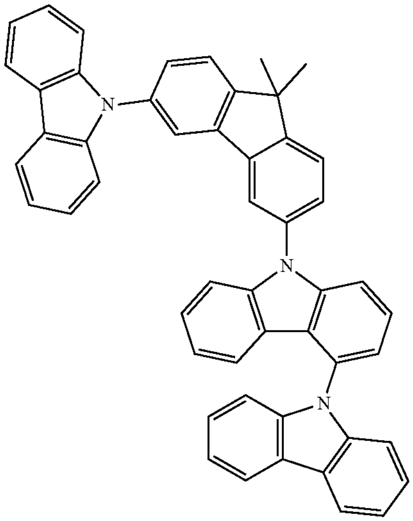
4-51
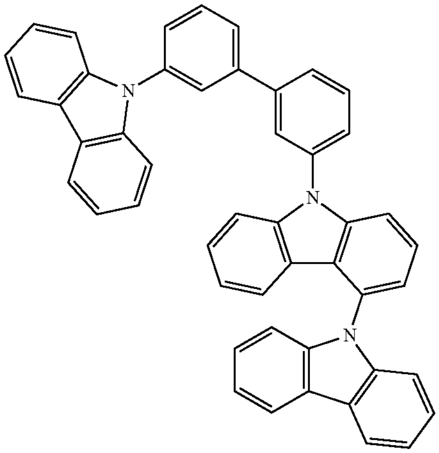
4-52
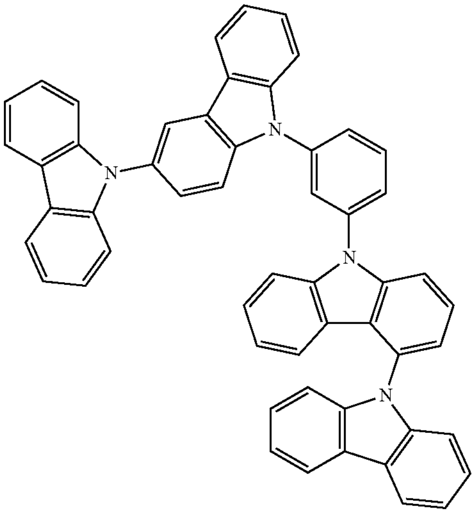

4-53
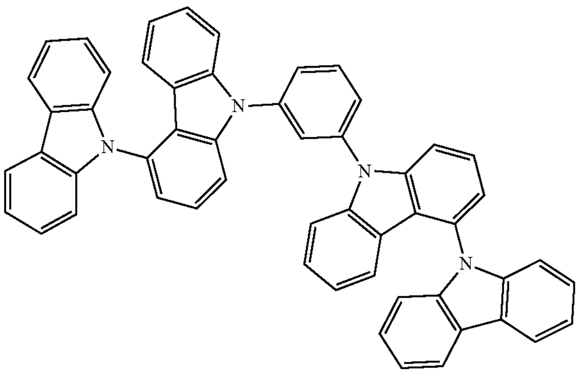
4-54
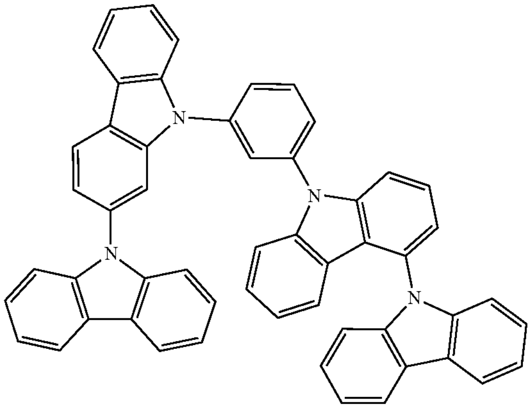
4-55
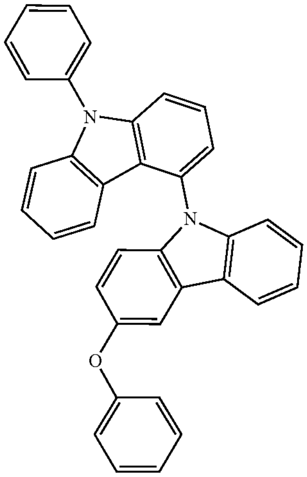
4-56
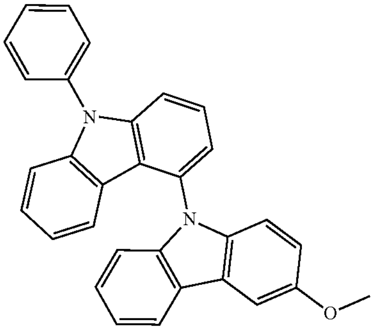
4-57
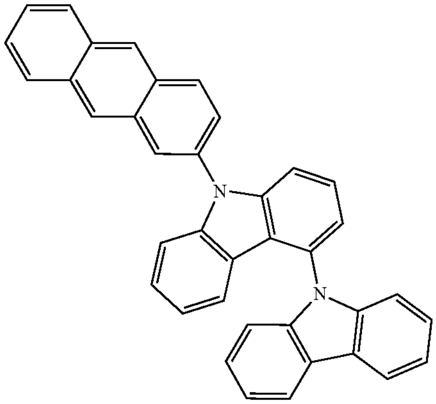
4-58
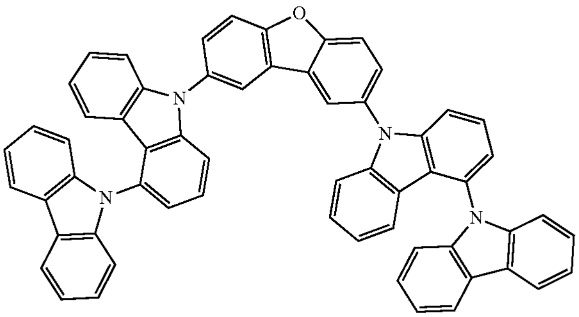
4-59
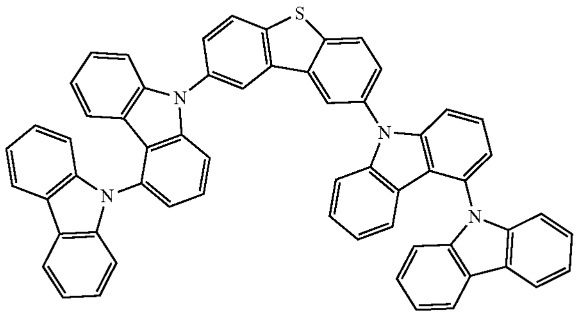
[C28]
4-60
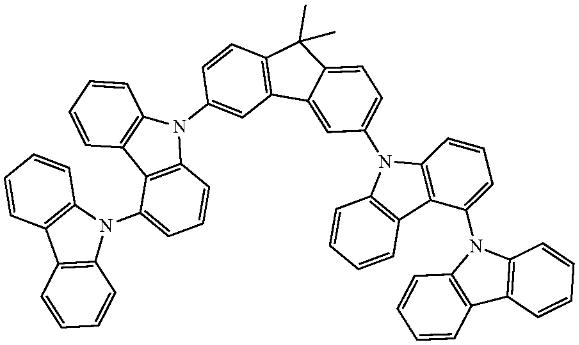

-continued
4-61
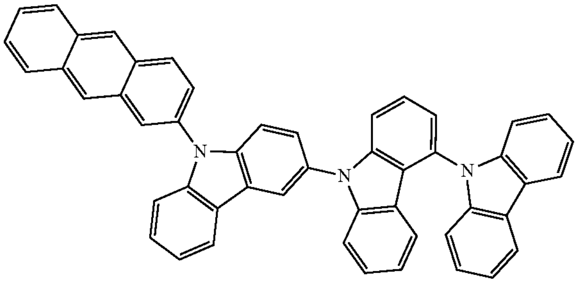
4-62
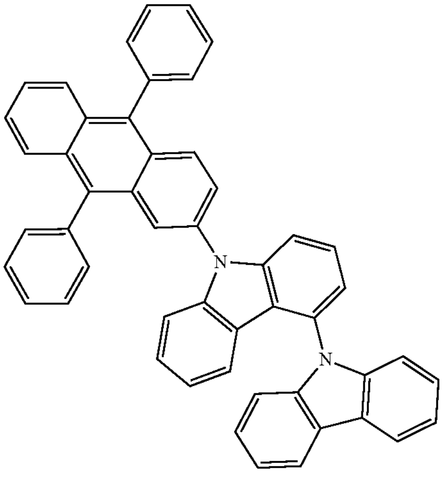
4-63
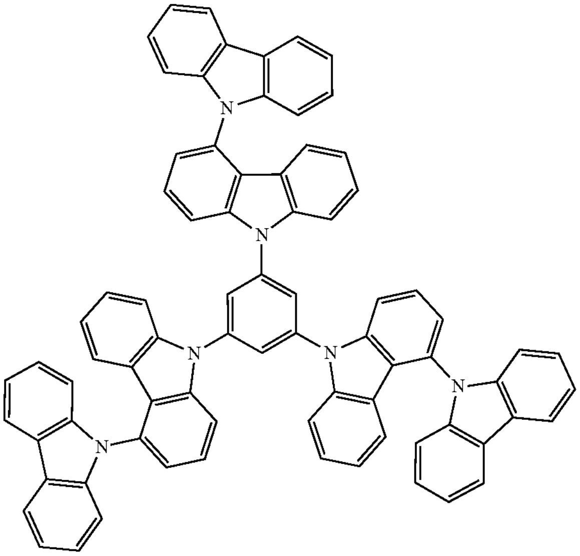
-continued
4-64
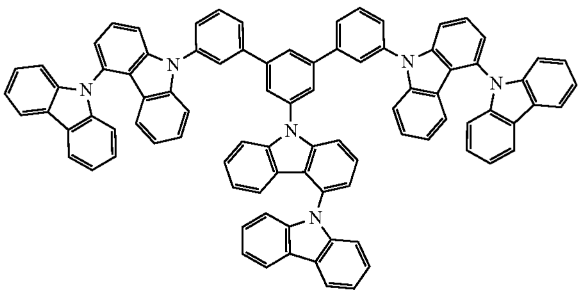
4-65
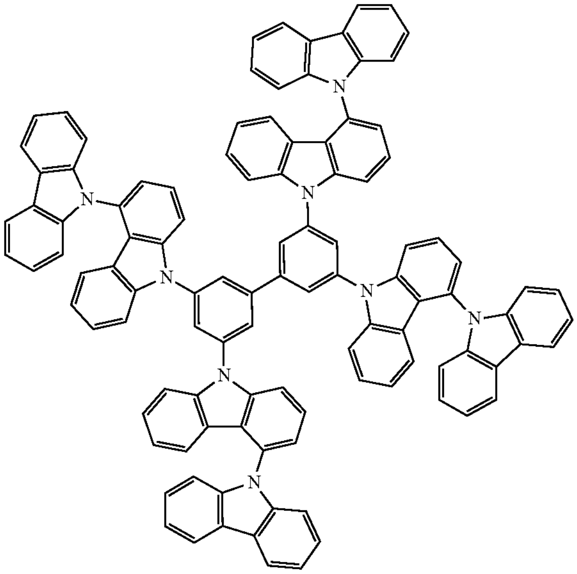
4-66
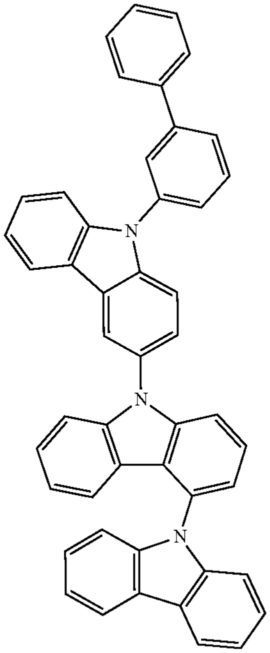

-continued
4-67
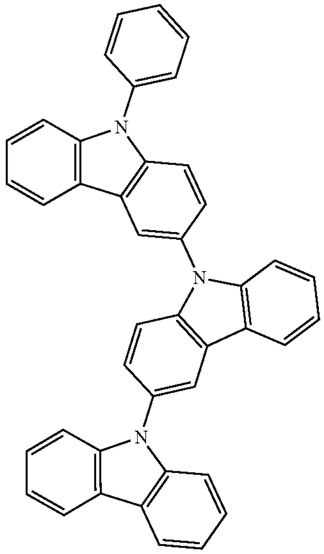
4-68
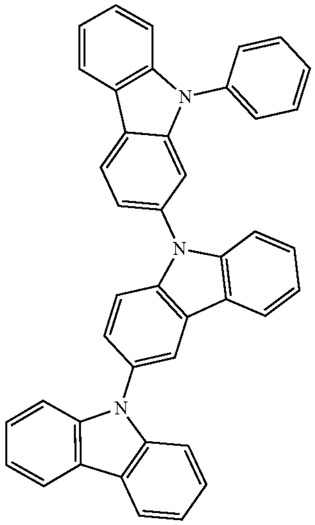
4-69
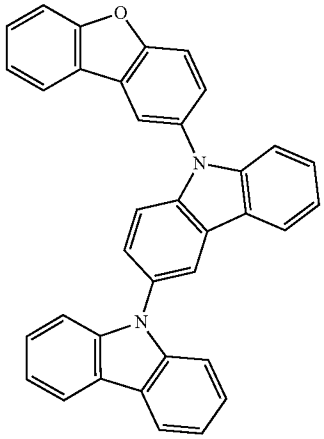
-continued
4-70
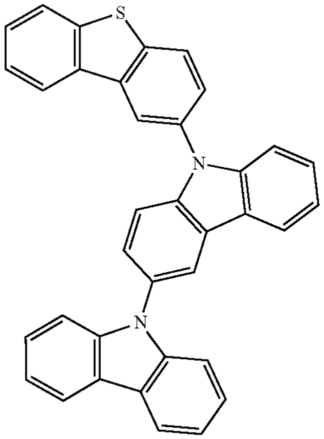
4-71
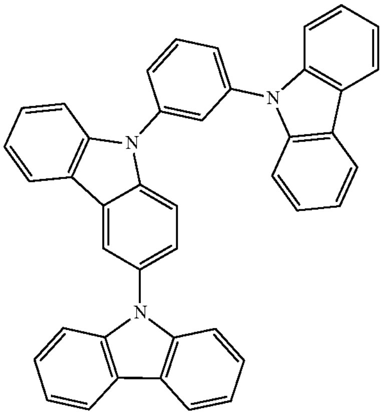
4-72
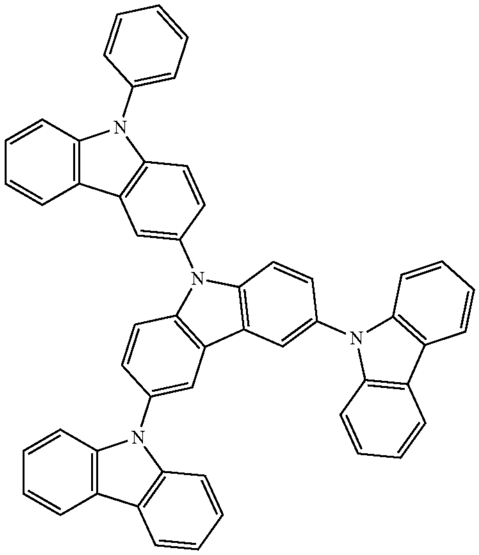

-continued
4-73
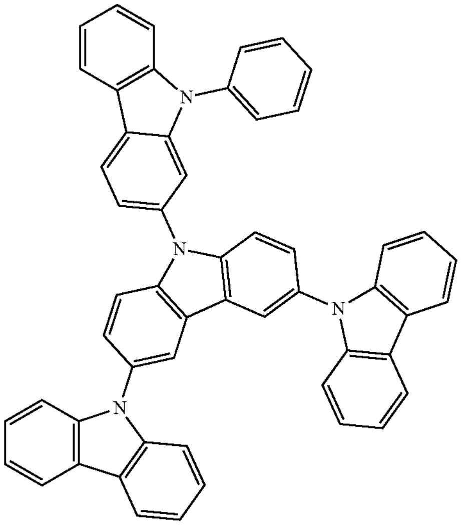
4-74
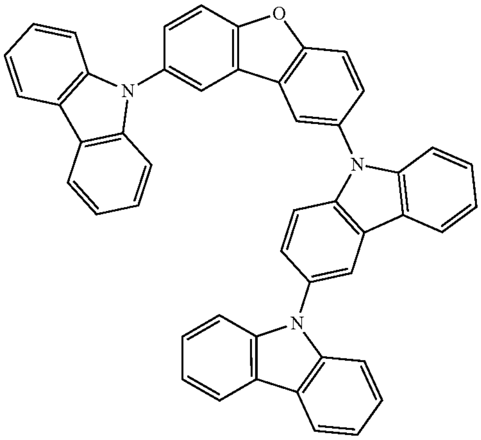
[C29]
4-75
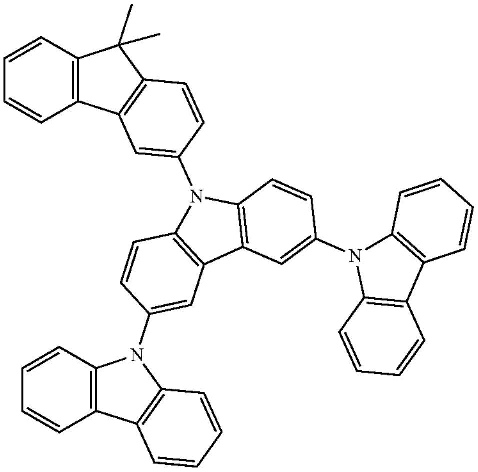
-continued
4-76
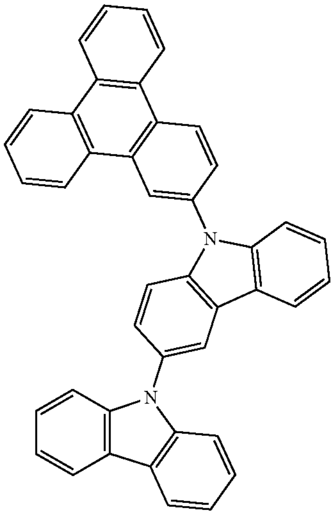
4-77
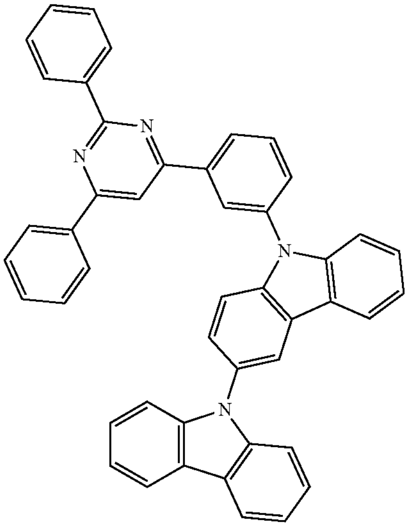

-continued
4-78
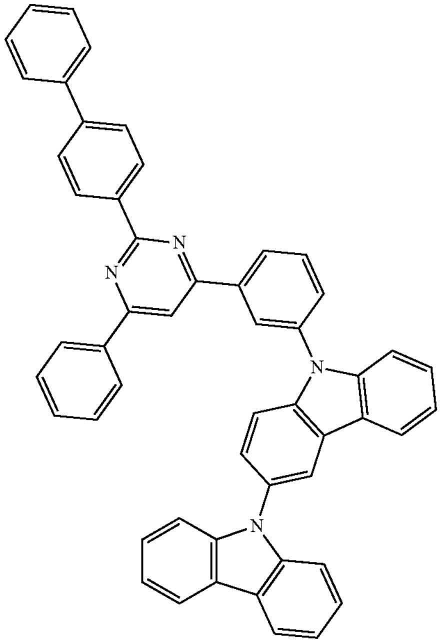
4-79
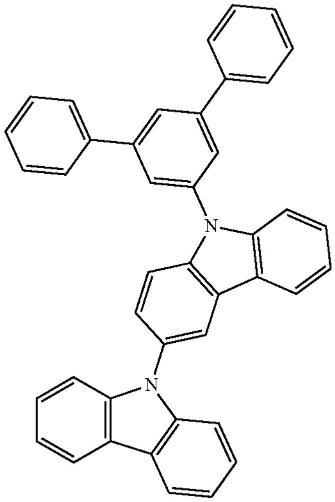
4-80
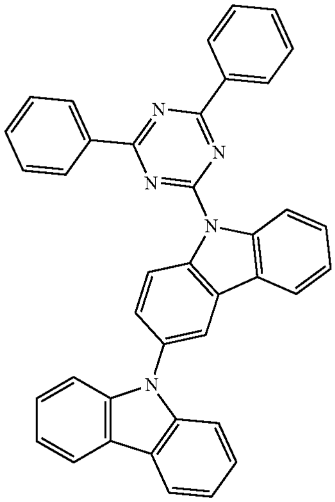
-continued
4-81
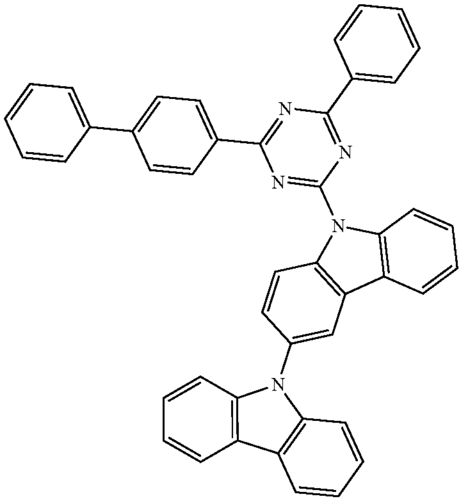
4-82
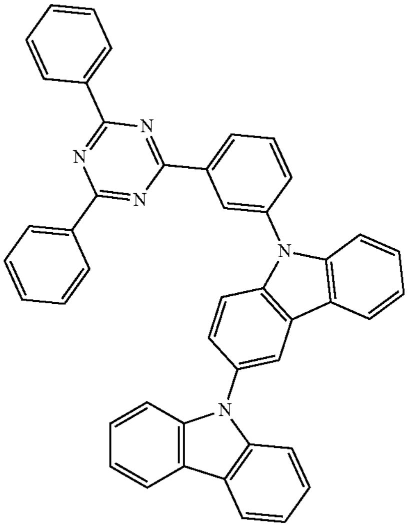
4-83
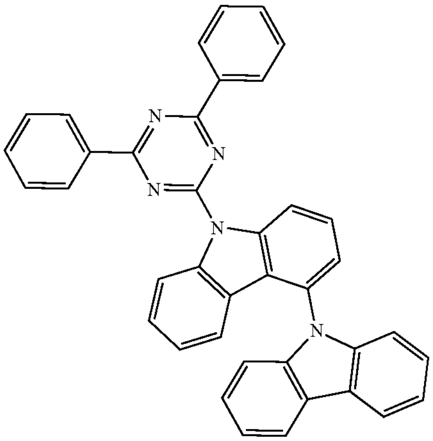

-continued 4-84

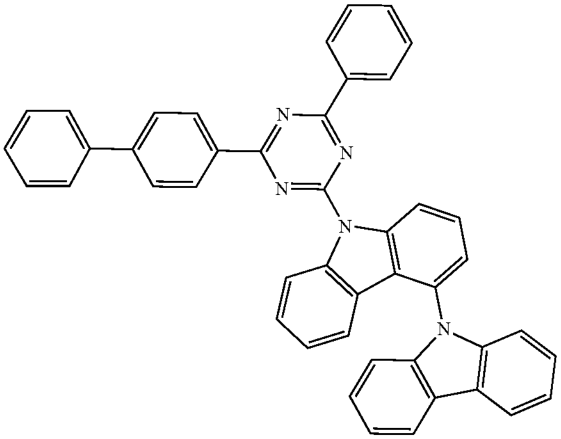

4-85

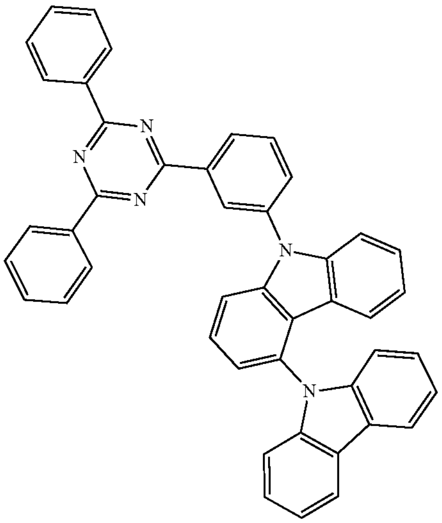

-continued 4-86

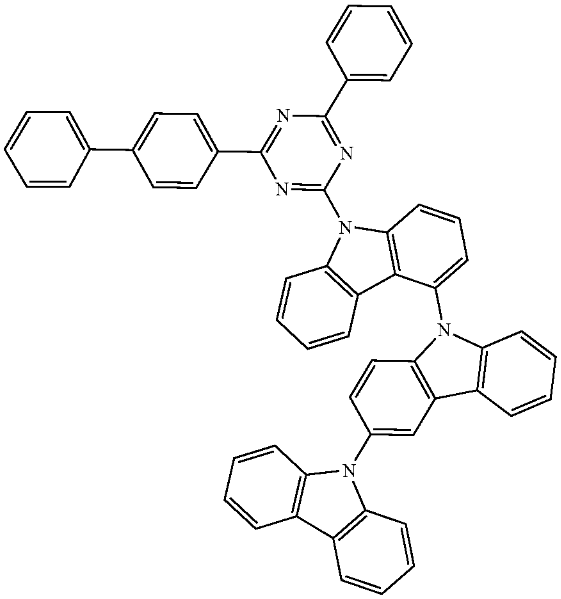

Next, the general formula (5) will be described.

In the general formula (5), a ring D is a heterocycle represented by formula (5a), and the ring D is fused to an adjacent ring at any position.

$R^{14}$ to $R^{16}$ are independently hydrogen, deuterium, an aliphatic hydrocarbon group having 1 to 10 carbon atoms, an aromatic hydrocarbon group having 6 to 30 carbon atoms, or an aromatic heterocyclic group having 3 to 12 carbon atoms. The aliphatic hydrocarbon group, aromatic hydrocarbon group and aromatic heterocyclic group are the same as in the case where $R^{10}$ to $R^{12}$ of the general formula (3) are of these groups, and preferred ranges therefor are also the same.

$L^8$ is independently a single bond, an aromatic hydrocarbon group having 6 to 10 carbon atoms, or a linked aromatic group in which 2 to 10 thereof are linked to each other. The aromatic hydrocarbon groups are the same as in the case where $L^6$ of the general formula (3) is of these groups, and a preferred range is also the same.

$Ar^2$ is an aromatic hydrocarbon group having 6 to 30 carbon atoms. Examples of the aromatic hydrocarbon group are the same as in the case where $L^7$ of the general formula (4) is of these groups, and a preferred range is also the same.

i, j and k each independently represent an integer of 0 to 3.

Specific examples of the indolocarbazole compound represented by the general formula (5) are described below, but the compound is not limited thereto.

[C30]
5-1
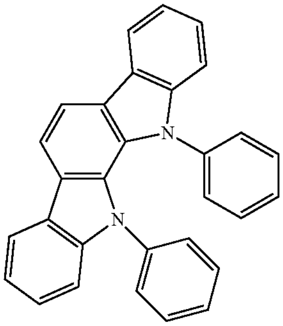
5-2
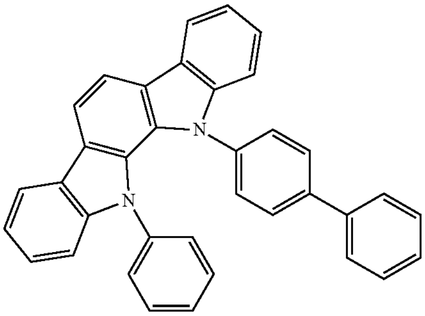
5-3
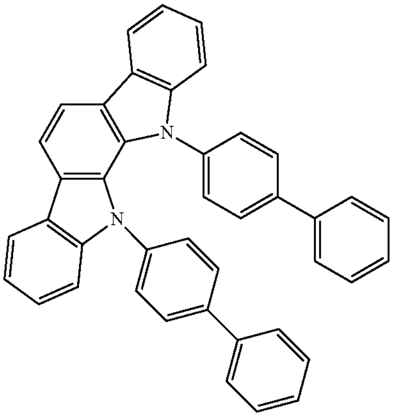
5-4
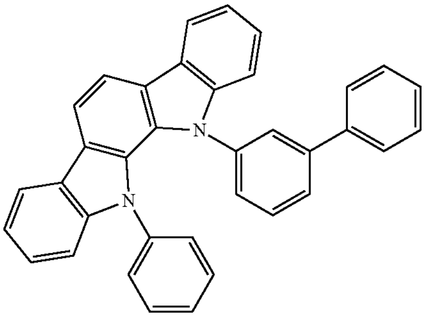
-continued
5-5
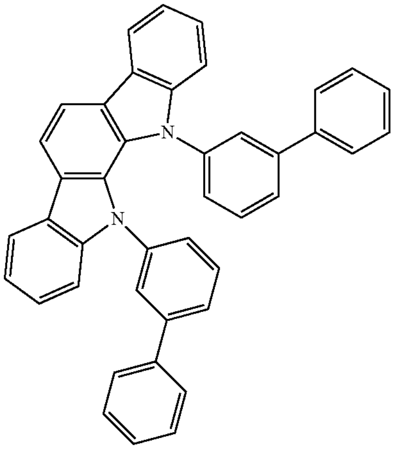
5-6
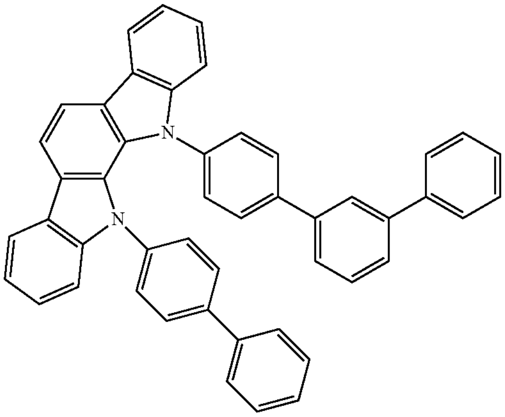
5-7
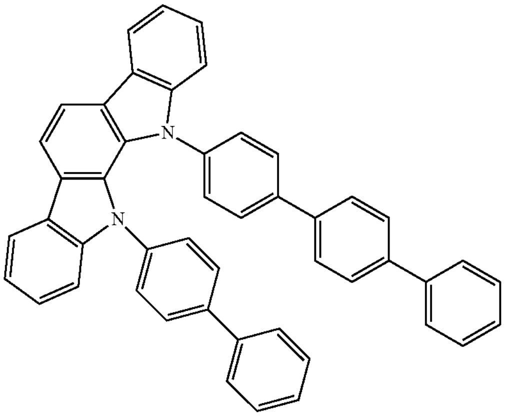

-continued
5-8
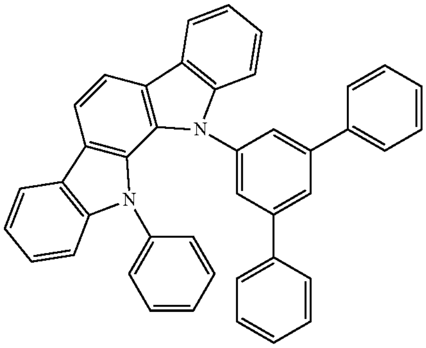
5-9
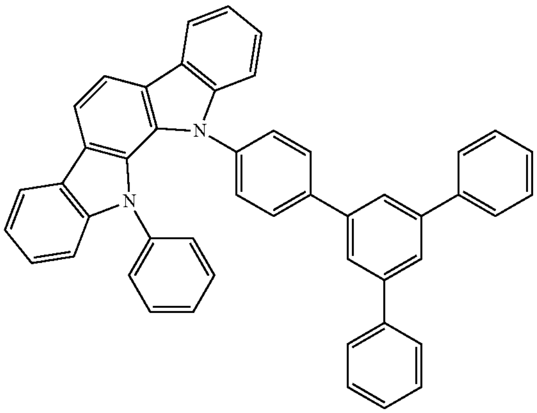
5-10
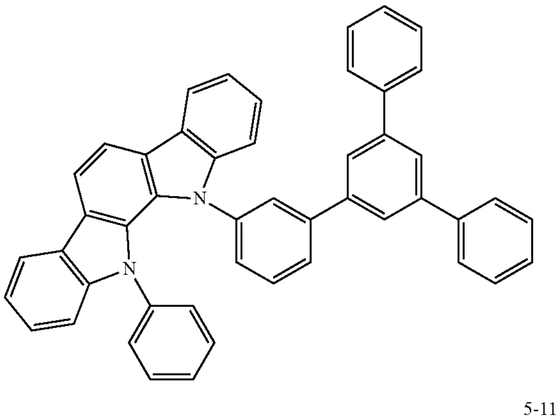
5-11
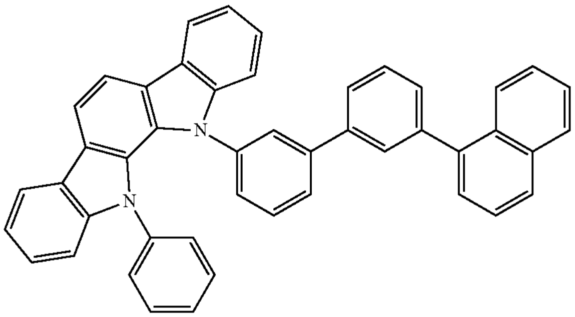
-continued
5-12
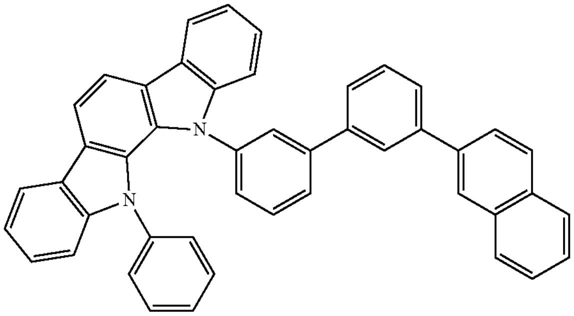
5-13
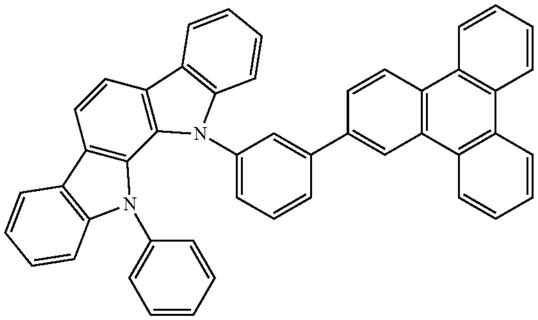
5-111
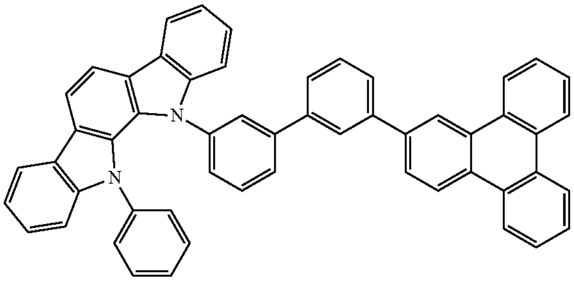
5-112
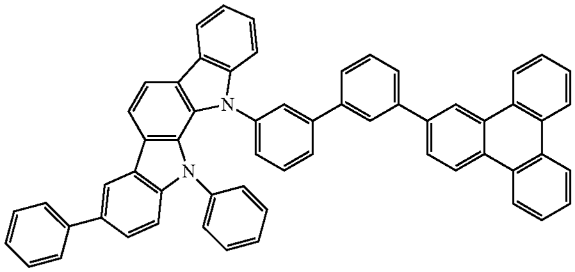
5-113
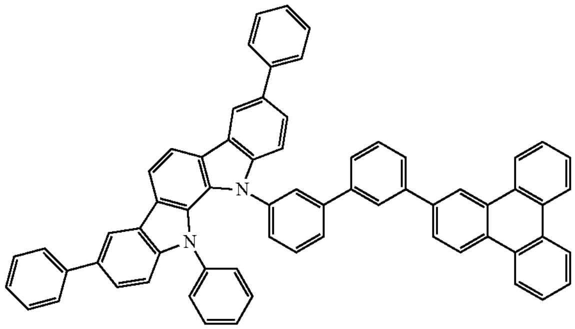

-continued
5-14
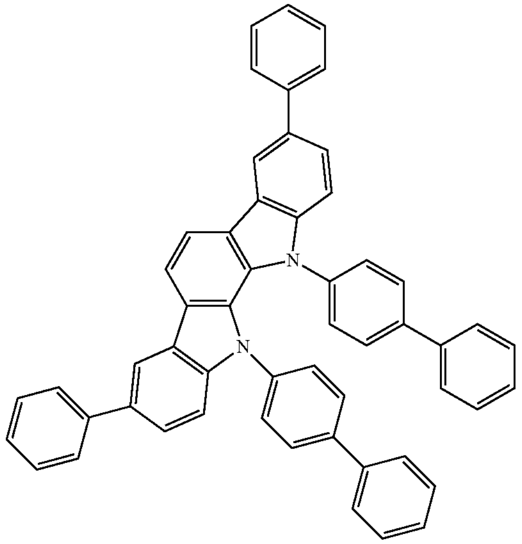
5-15
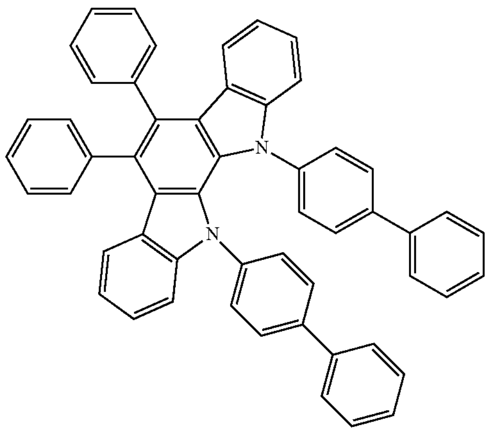
5-16
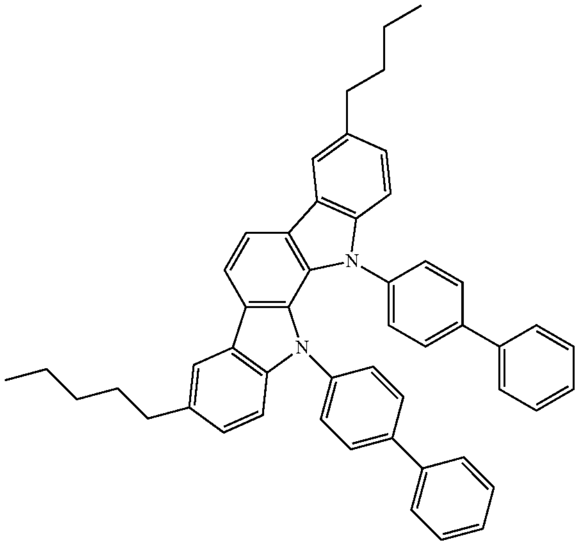
-continued
5-17
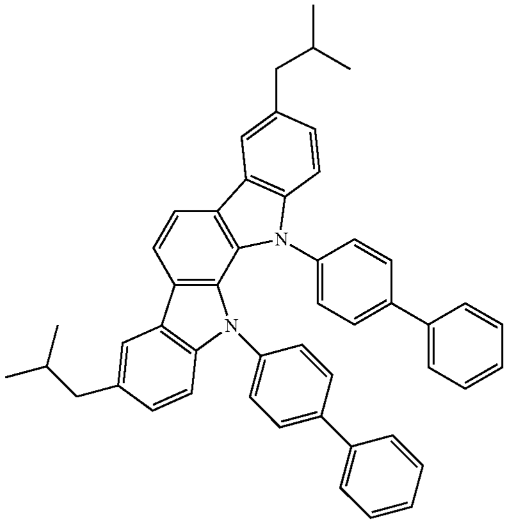
5-18
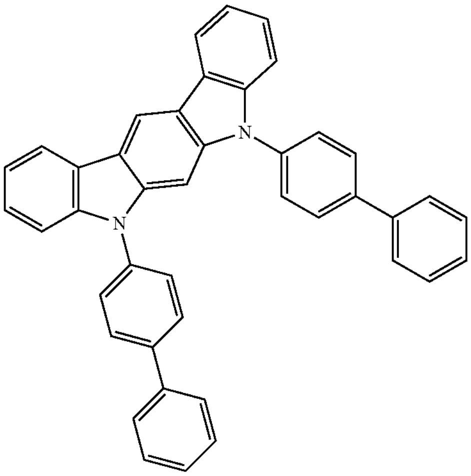
5-19
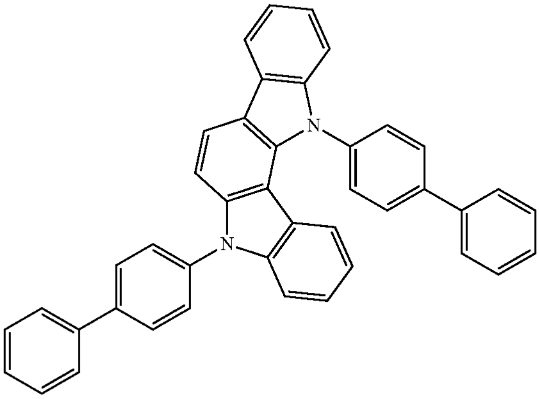

-continued 5-20

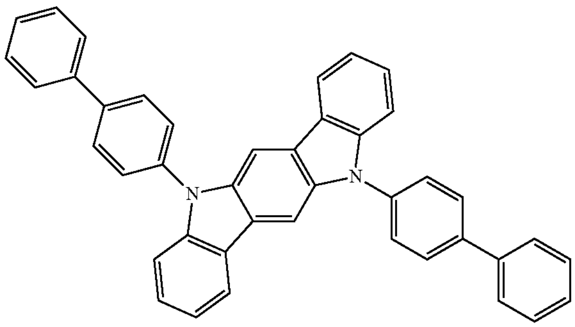

5-21

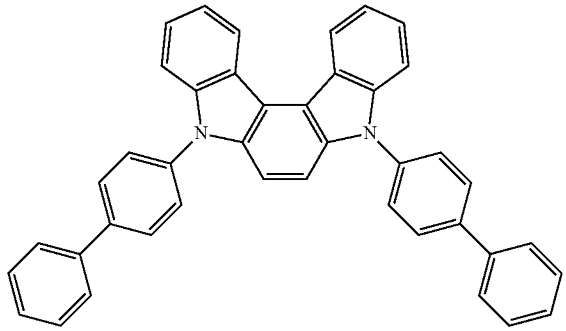

5-22

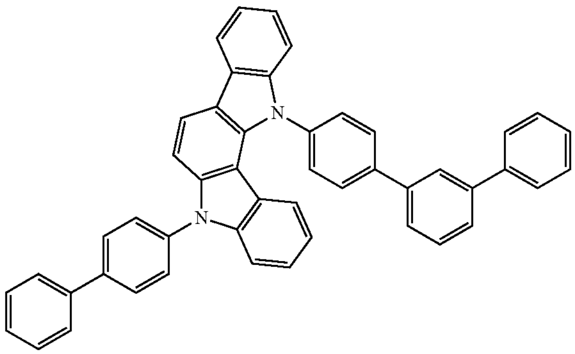

5-23

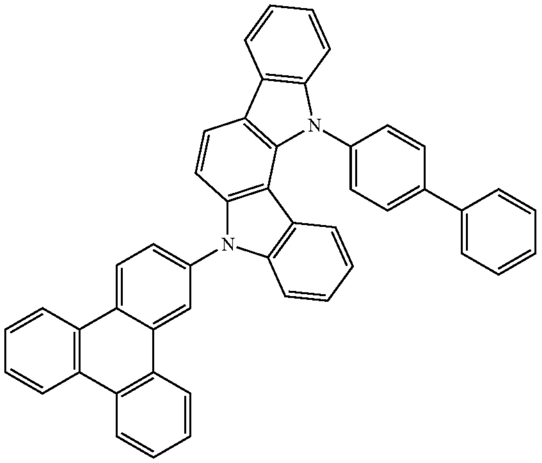

-continued 5-24

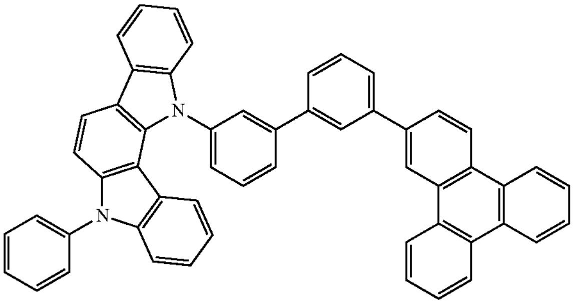

5-25

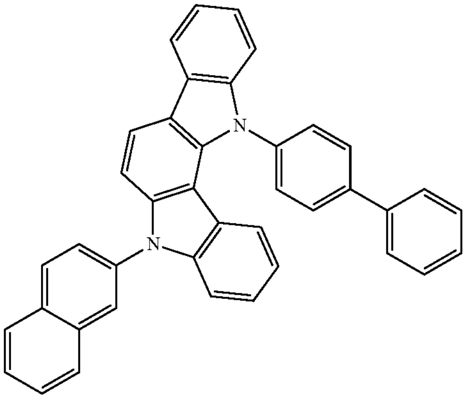

Use of the first host selected from the compounds represented by the general formula (1); and the second host selected from the compounds represented by the general formula (2), (3), (4) or (5) as host materials for a light-emitting layer can provide an excellent organic electroluminescent device.

The first host and the second host which are vapor-deposited from different individual vapor deposition sources can be used; however, it is preferable to premix them as a premixture before vapor deposition and to vapor-deposit the premixture simultaneously from one vapor deposition source to thereby form a light-emitting layer. In this case, the premixture may be mixed with a light-emitting dopant material necessary for formation of a light-emitting layer, or another host to be used as necessary. However, when there is a large difference in temperatures to provide desired vapor pressure, vapor deposition may be performed from another vapor deposition source.

In addition, regarding the mixing ratio (weight ratio) between the first host and the second host, the proportion of the first host is 20 to 60%, preferably more than 20% and less than 55%, and more preferably 40 to 50% based on the first host and the second host in total.

Next, the structure of the organic electroluminescent device of the present invention will be described by referring to the drawing, but the structure of the organic electroluminescent device of the present invention is not limited thereto.

The drawing FIGURE is a cross-sectional view showing a structure example of an organic electroluminescent device generally used for the present invention, in which there are indicated a substrate 1, an anode 2, a hole injection layer 3, a hole transport layer 4, a light-emitting layer 5, an electron transport layer 6, and a cathode 7. The organic electroluminescent device of the present invention may have an exciton blocking layer adjacent to the light-emitting layer and may have an electron blocking layer between the light-emitting layer and the hole injection layer. The exciton blocking layer can be inserted into either of the anode side and the cathode side of the light-emitting layer and inserted into both sides at the same time. The organic electroluminescent device of the present invention has the anode, the light-emitting layer, and the cathode as essential layers, and preferably has a hole injection transport layer and an electron injection transport layer in addition to the essential layers, and further preferably has a hole blocking layer between the light-emitting layer and the electron injection transport layer. Note that the hole injection transport layer refers to either or both of a hole injection layer and a hole transport layer, and the electron injection transport layer refers to either or both of an electron injection layer and an electron transport layer.

A structure reverse to that of the drawing FIGURE is applicable, in which a cathode 7, an electron transport layer 6, a light-emitting layer 5, a hole transport layer 4, and an anode 2 are laminated on a substrate 1 in this order. In this case, layers may be added or omitted as necessary.

—Substrate—

The organic electroluminescent device of the present invention is preferably supported on a substrate. The substrate is not particularly limited, and those conventionally used in organic electroluminescent devices may be used, and substrates made of, for example, glass, a transparent plastic, or quartz may be used.

—Anode—

Regarding an anode material for an organic electroluminescent device, it is preferable to use a material having a large work function (4 eV or more), selected from a metal, an alloy, an electrically conductive compound or a mixture thereof. Specific examples of such an electrode material include a metal such as Au, and a conductive transparent material such as CuI, indium tin oxide (ITO), $SnO_2$, and ZnO. In addition, an amorphous material such as IDIXO ($In_2O_3$—ZnO), which is capable of forming a transparent conductive film, may be used. Regarding the anode, such an electrode material is used to form a thin film by, for example, a vapor-deposition or sputtering method, and a desired shape pattern may be formed by a photolithographic method; or if the pattern accuracy is not particularly required (about 100 μm or more), a pattern may be formed via a desired shape mask when the electrode material is vapor-deposited or sputtered. Alternatively, when a coatable substance such as an organic conductive compound is used, a wet film formation method such as a printing method or a coating method may be used. For taking emitted light from the anode, it is desired to have a transmittance of more than 10%, and the sheet resistance for the anode is preferably several hundreds Ω/or less. The film thickness is selected usually within 10 to 1000 nm, preferably within 10 to 200 nm though depending on the material.

—Cathode—

Meanwhile, regarding a cathode material, preferable to a material having a small work function (4 eV or less), selected from a metal (an electron injection metal), an alloy, an electrically conductive compound, or a mixture thereof are used.

Specific examples of such an electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among these, from the viewpoint of the electron injectability and the durability against oxidation and the like, a mixture of an electron injection metal and a second metal which is a stable metal having a larger work function value is suitable, and examples thereof include a magnesium/silver mixture, a magnesium/aluminum mixture, a magnesium/indium mixture, an aluminum/aluminum oxide mixture, a lithium/aluminum mixture and aluminum. The cathode can be produced by forming a thin film by a method such as vapor-depositing or sputtering of such a cathode material. In addition, the sheet resistance of cathode is preferably several hundreds Ω/or less. The film thickness is selected usually within 10 nm to 5 μm, preferably within 50 to 200 nm. Note that for transmission of emitted light, if either one of the anode and cathode of the organic electroluminescent device is transparent or translucent, emission luminance is improved, which is convenient.

In addition, formation of a film of the above metal with a thickness of 1 to 20 nm on the cathode, followed by formation of a conductive transparent material described in the description on the anode thereon, enables production of a transparent or translucent cathode, and application of this enables production of a device wherein an anode and a cathode both have transmittance.

—Light-Emitting Layer—

The light-emitting layer is a layer that emits light after excitons are generated when holes and electrons injected from the anode and the cathode, respectively, are recombined. The light-emitting layer contains an organic light-emitting dopant material and a host.

As a host, the first host and the second host are used.

Regarding the compound represented by the general formula (1) as the first host, one kind thereof may be used, or two or more kinds thereof may be used. Likewise, regarding the carbazole compound or indolocarbazole compound represented by the general formulas (2) to (5) as the second host, one kind thereof may be used, or two or more kinds thereof may be used.

If necessary, one, or two or more known host materials may be used in combination; however, it is preferable that an amount thereof to be used be 50 wt % or less, preferably 25 wt % or less based on the host materials in total.

Other material may be used as the host.

The first host and the second host may be vapor-deposited from different vapor deposition sources, or alternatively, may be premixed before vapor deposition to prepare a premixture and thus the first host and the second host may be vapor-deposited from one vapor deposition source at the same time.

When the first host and the second host are premixed and used, it is desirable that a difference in 50% weight reduction temperature ($T_{50}$) be small in order to produce an organic electroluminescent device having favorable characteristics with high reproducibility. The 50% weight reduction temperature is a temperature at which the weight is reduced by 50% when the temperature is raised to 550° C. from room temperature at a rate of 10° C./min in TG-DTA measurement under a nitrogen stream reduced pressure (50 Pa). It is considered that vaporization due to evaporation or sublimation the most vigorously occurs around this temperature.

The difference in 50% weight reduction temperatures of the first host and the second host is preferably within 20° C. and more preferably within 15° C. Regarding a premixing method, a known method such as pulverization and mixing can be used, and it is desirable to mix them as uniformly as possible.

When a phosphorescent dopant is used as a light-emitting dopant material, preferred is a phosphorescent dopant including an organic metal complex containing at least one metal selected from ruthenium, rhodium, palladium, silver, rhenium, osmium, iridium, platinum and gold. Specifically, iridium complexes described in J. Am. Chem. Soc. 2001, 123, 4304 and Japanese Translation of PCT International Application Publication No. 2013-53051 are preferably used, but the phosphorescent dopant is not limited thereto.

Regarding the phosphorescent dopant material, only one kind thereof may be contained in the light-emitting layer, or two or more kinds thereof may be contained. A content of the phosphorescent dopant material is preferably 0.1 to 30 wt % and more preferably 1 to 20 wt % with respect to the host material.

The phosphorescent dopant material is not particularly limited, and specific examples thereof include the following.

[C31]

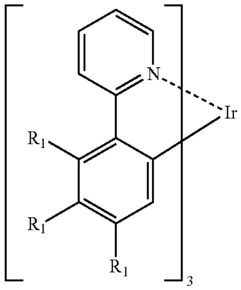

$R_1$: H, $CH_3$, $CF_3$, F

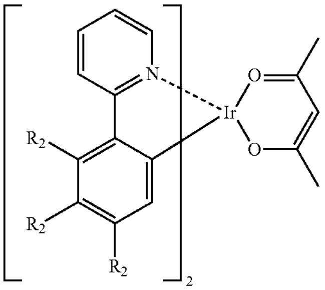

$R_2$: H, F

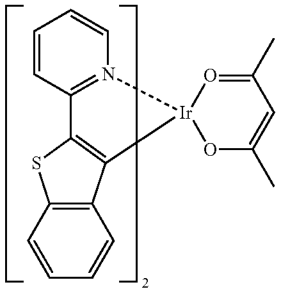

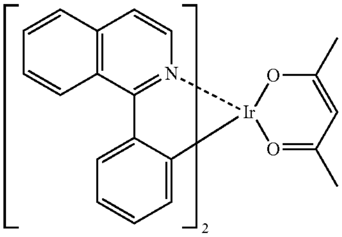

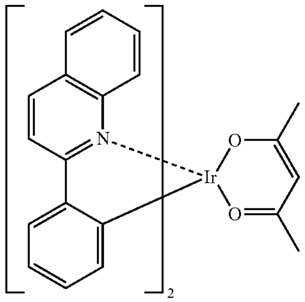

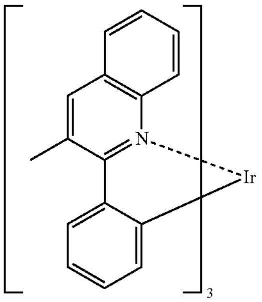

-continued

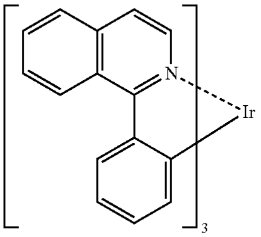

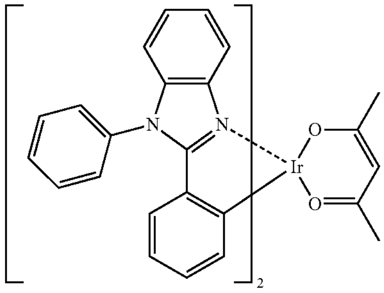

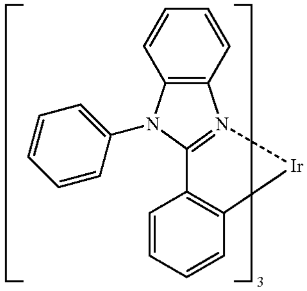

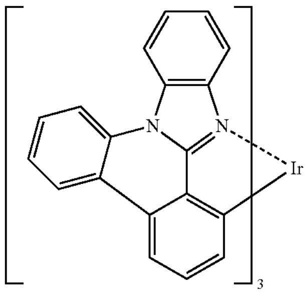

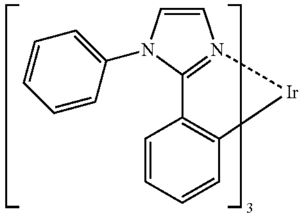

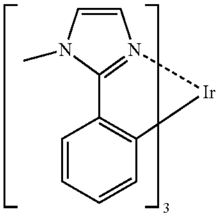

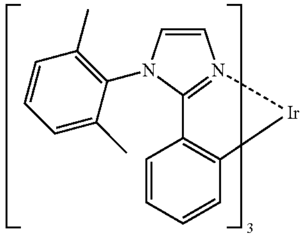

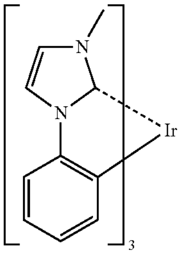

-continued

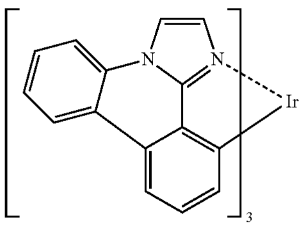

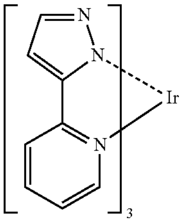

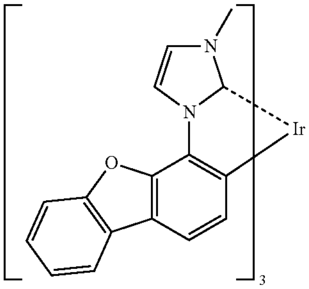

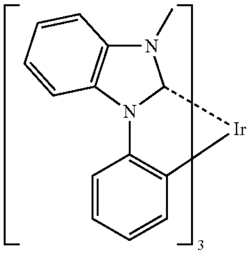

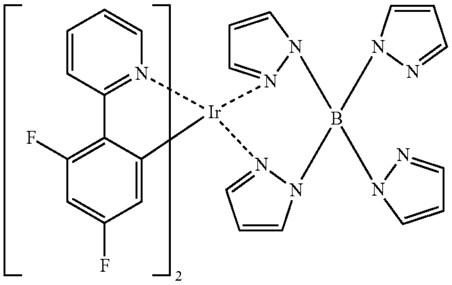

[C32]

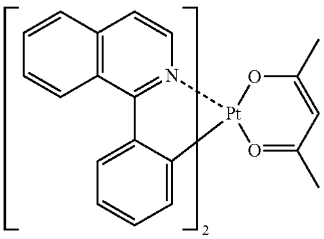

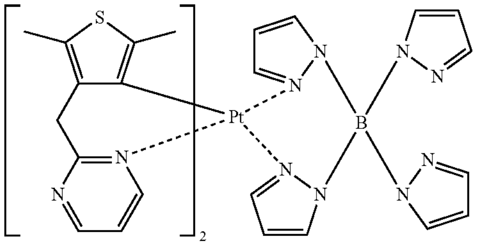

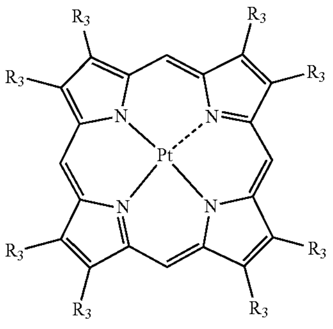

$R_3$: $CH_3$, $CH_2CH_3$

-continued

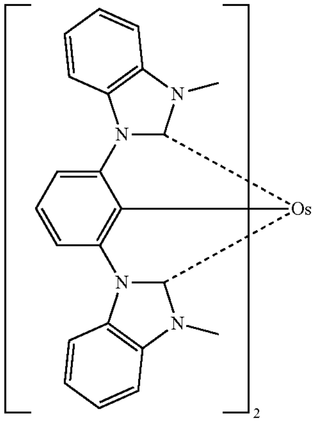

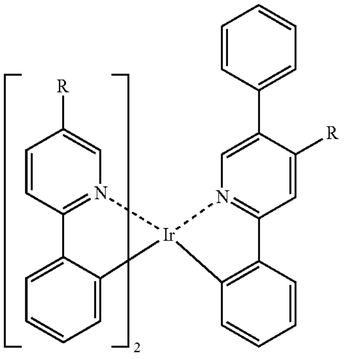

R: H, $CH_3$, $CD_3$

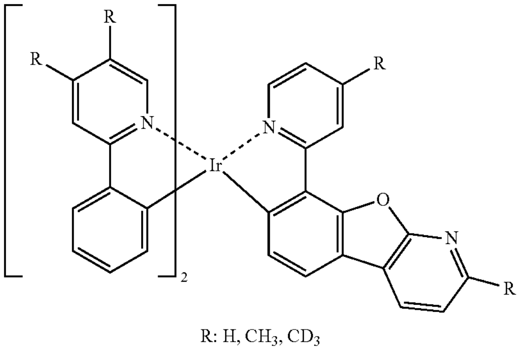

R: H, $CH_3$, $CD_3$

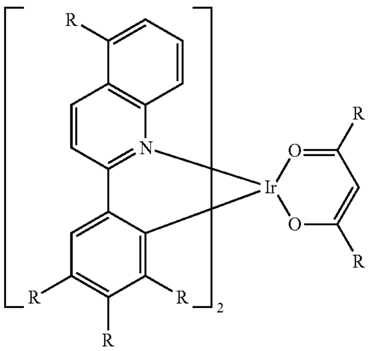

R: H, $CH_3$, $C_4H_9$, $CD_3$

When a fluorescence-emitting dopant is used as the light-emitting dopant material, the fluorescence-emitting dopant is not particularly limited. Examples thereof include benzoxazole derivatives, benzothiazole derivatives, benzimidazole derivatives, styrylbenzene derivatives, polyphenyl derivatives, diphenylbutadiene derivatives, tetraphenyl butadiene derivatives, naphthalimido derivatives, coumarin derivatives, fused aromatic compounds, perinone derivatives, oxadiazole derivatives, oxazine derivatives, aldazine derivatives, pyrrolidine derivatives, cyclopentadiene derivatives, bisstyryl anthracene derivatives, quinacridone derivatives, pyrrolopyridine derivatives, thiadiazolopyridine derivatives, styrylamine derivatives, diketopyrrolopyrrole derivatives, aromatic dimethylidine compounds, metal complexes of 8-quinolinol derivatives or metal complexes of pyromethene derivatives, rare earth complexes, various metal complexes represented by transition metal complexes, polymer compounds such as polythiophene, polyphenylene, and polyphenylene vinylene, and organosilane derivatives. Preferred examples thereof include fused aromatic derivatives, styryl derivatives, diketopyrrolopyrrole derivatives, oxazine derivatives, pyromethene metal complexes, transition metal complexes, and lanthanoid complexes. More preferable examples thereof include naphthalene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthalene, hexacene, naphtho[2,1-f]isoquinoline, α-naphthaphenanthridine, phenanthrooxazole, quinolino[6,5-f]quinoline, and benzothiophanthrene. These may have an alkyl group, an aryl group, an aromatic heterocyclic group, or a diarylamino group as a substituent.

Regarding the fluorescence-emitting dopant material, only one kind thereof may be contained in the light-emitting layer, or two or more kinds thereof may be contained. A content of the fluorescence-emitting dopant material is preferably 0.1% to 20% and more preferably 1% to 10% with respect to the host material.

When a thermally activated delayed fluorescence-emitting dopant is used as the light-emitting dopant material, the thermally activated delayed fluorescence-emitting dopant is not particularly limited. Examples thereof include: metal complexes such as a tin complex and a copper complex; indolocarbazole derivatives described in WO2011/070963; cyanobenzene derivatives and carbazole derivatives described in Nature 2012, 492, 234; and phenazine derivatives, oxadiazole derivatives, triazole derivatives, sulfone derivatives, phenoxazine derivatives, and acridine derivatives described in Nature Photonics 2014, 8,326.

The thermally activated delayed fluorescence-emitting dopant material is not particularly limited, and specific examples thereof include the following.

[C33]

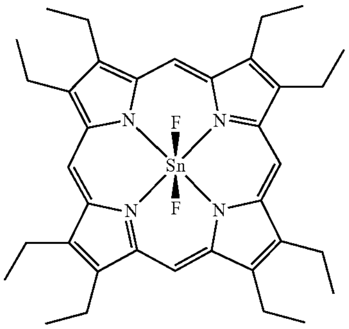

-continued

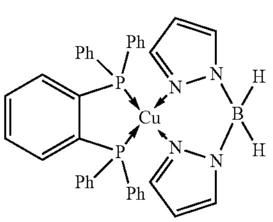

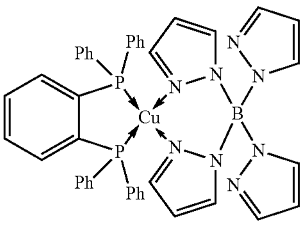

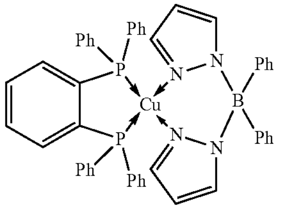

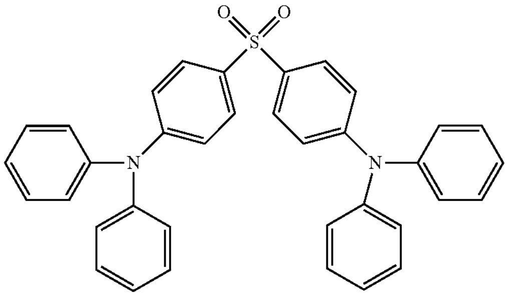

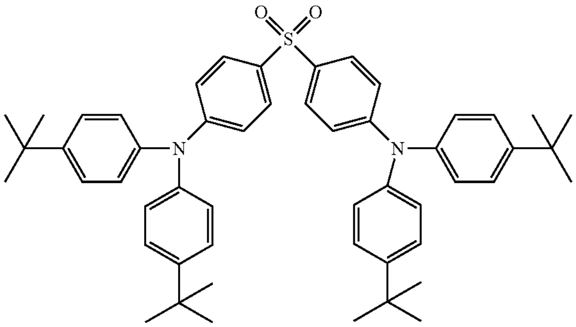

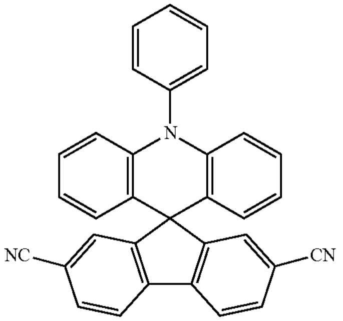

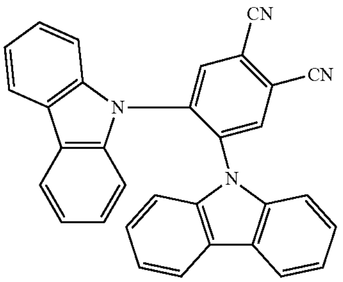

-continued

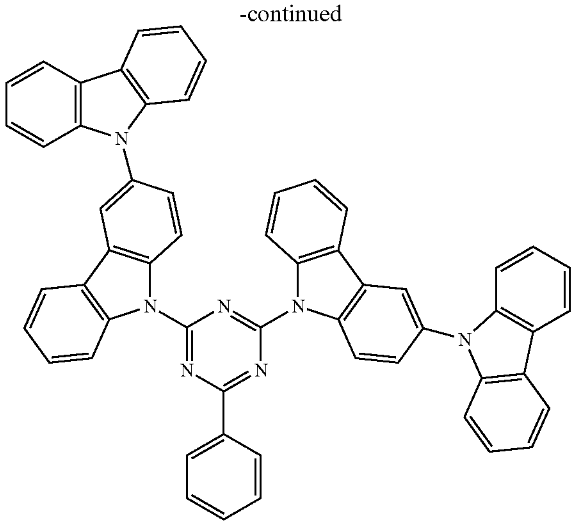

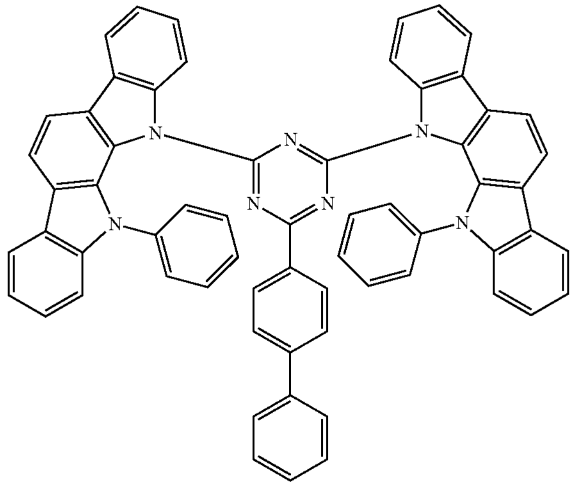

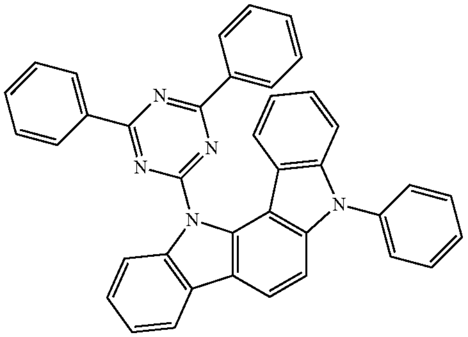

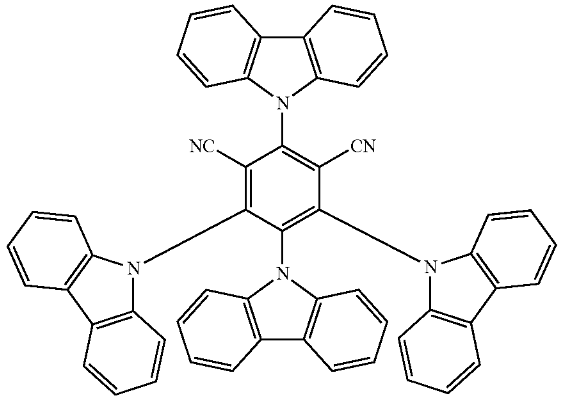

-continued

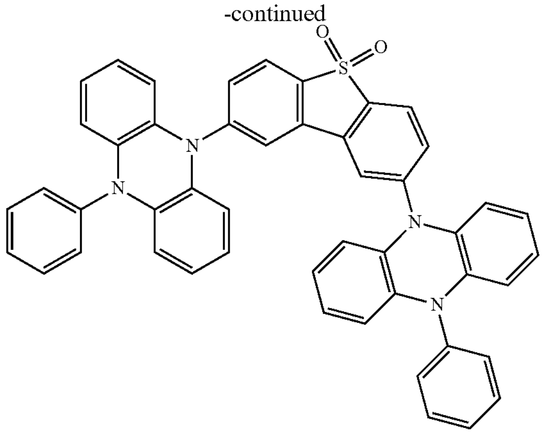

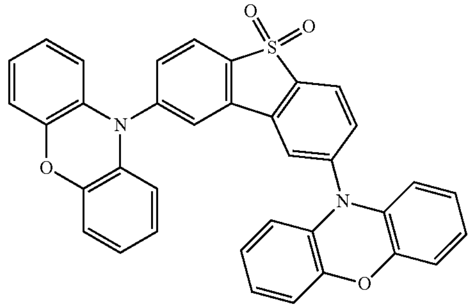

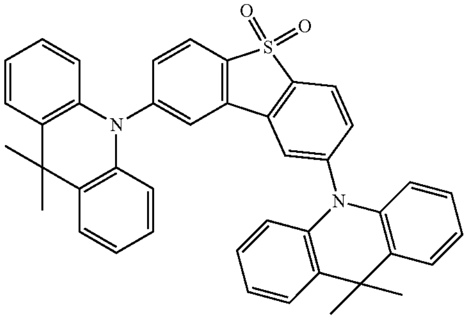

Regarding the thermally activated delayed fluorescence-emitting dopant material, only one kind thereof may be contained in the light-emitting layer, or two or more kinds thereof may be contained. In addition, the thermally activated delayed fluorescence-emitting dopant may be used by mixing with a phosphorescent dopant and a fluorescence-emitting dopant. A content of the thermally activated delayed fluorescence-emitting dopant material is preferably 0.1% to 50% and more preferably 1% to 30% with respect to the host material.

—Injection Layer—

The injection layer is a layer that is provided between an electrode and an organic layer in order to lower a driving voltage and improve emission luminance, and includes a hole injection layer and an electron injection layer, and may be present between the anode and the light-emitting layer or the hole transport layer, and between the cathode and the light-emitting layer or the electron transport layer. The injection layer can be provided as necessary.

—Hole Blocking Layer—

The hole blocking layer has a function of the electron transport layer in a broad sense, and is made of a hole blocking material having a function of transporting electrons and a significantly low ability to transport holes, and can block holes while transporting electrons, thereby improving a probability of recombining electrons and holes in the light-emitting layer.

For the hole blocking layer, a known hole blocking layer material can be used, but it is preferred for the layer to contain the compound represented by the general formula (1).

—Electron Blocking Layer—

The electron blocking layer has a function of a hole transport layer in a broad sense and blocks electrons while transporting holes, thereby enabling a probability of recombining electrons and holes in the light-emitting layer to be improved.

Regarding the material of the electron blocking layer, a known electron blocking layer material can be used and a material of the hole transport layer to be described below can be used as necessary. A film thickness of the electron blocking layer is preferably 3 to 100 nm, and more preferably 5 to 30 nm.

—Exciton Blocking Layer—

The exciton blocking layer is a layer for preventing excitons generated by recombination of holes and electrons in the light-emitting layer from being diffused in a charge transport layer, and insertion of this layer allows excitons to be efficiently confined in the light-emitting layer, enabling the luminous efficiency of the device to be improved. The exciton blocking layer can be inserted, in a device having two or more light-emitting layers adjacent to each other, between two adjacent light-emitting layers.

Regarding the material of the exciton blocking layer, a known exciton blocking layer material can be used. Examples thereof include 1,3-dicarbazolyl benzene (mCP) and bis(2-methyl-8-quinolinolato)-4-phenylphenolato aluminum (III) (BAlq).

—Hole Transport Layer—

The hole transport layer is made of a hole transport material having a function of transporting holes, and the hole transport layer can be provided as a single layer or a plurality of layers.

The hole transport material has either hole injection, transport properties or electron barrier properties, and may be an organic material or an inorganic material. For the hole transport layer, any one selected from conventionally known compounds can be used. Examples of such a hole transport material include porphyrin derivatives, arylamine derivatives, triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styryl anthracene derivatives, fluorenone derivatives, hydrazone derivatives, stilbene derivatives, silazane derivatives, an aniline copolymer, and a conductive polymer oligomer, and particularly a thiophene oligomer. Use of porphyrin derivatives, arylamine derivatives, or styrylamine derivatives preferred. Use of arylamine compounds is more preferred.

—Electron Transport Layer—

The electron transport layer is made of a material having a function of transporting electrons, and the electron transport layer can be provided as a single layer or a plurality of layers.

The electron transport material (which may also serve as a hole blocking material) may have a function of transferring electrons injected from the cathode to the light-emitting layer. For the electron transport layer, any one selected from conventionally known compounds can be used, and examples thereof include polycyclic aromatic derivatives such as naphthalene, anthracene, and phenanthroline, tris(8-quinolinolato)aluminum(III) derivatives, phosphine oxide derivatives, nitro-substituted fluorene derivatives, diphenylquinone derivatives, thiopyrandioxide derivatives, carbodiimide, fluorenylidene methane derivatives, anthraquinodimethane and anthrone derivatives, bipyridine derivatives, quinoline derivatives, oxadiazole derivatives, benzimidazole derivatives, benzothiazole derivatives, and indolocarbazole derivatives. In addition, a polymer material in which the above material is introduced into a polymer chain or the above material is used for a main chain of a polymer can be used.

EXAMPLES

Hereafter, the present invention will be described in detail by referring to Examples, but the present invention is not limited these Examples and can be implemented in various forms without departing from the gist thereof.

Example 1

On a glass substrate on which an anode made of ITO with a film thickness of 110 nm was formed, respective thin films were laminated by a vacuum evaporation method at a degree of vacuum of $4.0\times10^{-5}$ Pa. First, HAT-CN was formed with a thickness of 25 nm as a hole injection layer on ITO, and next, NPD was formed with a thickness of 30 nm as a hole transport layer. Next, HT-1 was formed with a thickness of 10 nm as an electron blocking layer. Then, compound 1-1 as a first host, compound 2-4 as a second host and $Ir(ppy)_3$ as a light-emitting dopant were co-vapor-deposited from different vapor deposition sources, respectively, to form a light-emitting layer with a thickness of 40 nm. In this case, co-vapor deposition was performed under vapor deposition conditions such that the concentration of $Ir(ppy)_3$ was 10 wt % and the weight ratio between the first host and the second host was 30:70. Next, ET-1 was formed with a thickness of 20 nm as an electron transport layer. Further, LiF was formed with a thickness of 1 nm as an electron injection layer on the electron transport layer. Finally, Al was formed with a thickness of 70 nm as a cathode on the electron injection layer to produce an organic electroluminescent device.

Examples 1 to 88

Organic electroluminescent devices were produced in the same manner as in Example 1 except that compounds shown in Tables 1 and 2 were used as the first host and the second host instead of those of Example 1.

Example 89 to 96

The first host and the second host were mixed in advance to prepare a premixture, and the premixture was co-vapor-deposited from one vapor deposition source.

Organic electroluminescent devices were produced in the same manner as in Example 1 except for use of a premixture obtained by weighing a first host (0.30 g) and a second host (0.70 g) and mixing them while grinding in a mortar.

Evaluation results of the produced organic electroluminescent devices are shown in Tables 1 to 4.

In the tables, the luminance, driving voltage, and luminous efficiency are values at the time when the driving current was 20 mA/cm$^2$, and they exhibit initial characteristics. LT70 is a time period needed for the initial luminance to be reduced to 70% thereof, and it represents lifetime characteristics.

TABLE 1

| Example | First host compound | Second host compound | Luminance (cd/m2) | Voltage (V) | Power efficiency (lm/W) | LT70 (h) |
|---|---|---|---|---|---|---|
| 1 | 1-1 | 2-4 | 11000 | 4.0 | 43.2 | 1100 |
| 2 | 1-1 | 2-5 | 10000 | 3.8 | 41.3 | 1300 |
| 3 | 1-1 | 2-6 | 10000 | 3.8 | 41.3 | 1300 |
| 4 | 1-1 | 2-9 | 10000 | 3.9 | 40.3 | 1000 |
| 5 | 1-1 | 2-10 | 10000 | 3.9 | 40.3 | 1000 |
| 6 | 1-1 | 2-13 | 10000 | 3.9 | 40.3 | 1000 |
| 7 | 1-1 | 2-21 | 11000 | 4.2 | 41.1 | 1000 |
| 8 | 1-1 | 2-22 | 11000 | 3.9 | 44.3 | 1000 |
| 9 | 1-1 | 2-23 | 11000 | 3.9 | 44.3 | 1000 |
| 10 | 1-1 | 2-24 | 11000 | 4.3 | 40.2 | 1000 |
| 11 | 1-1 | 2-27 | 11000 | 4 | 43.2 | 1000 |
| 12 | 1-1 | 2-28 | 11000 | 4 | 43.2 | 1000 |
| 15 | 1-1 | 3-1 | 10000 | 4.1 | 38.3 | 1000 |
| 16 | 1-1 | 3-5 | 10000 | 4 | 39.3 | 1000 |
| 17 | 1-1 | 3-8 | 10000 | 4 | 39.3 | 1000 |
| 18 | 1-1 | 3-12 | 10000 | 3.9 | 40.3 | 1000 |
| 19 | 1-1 | 3-16 | 10000 | 3.9 | 40.3 | 1000 |
| 20 | 1-1 | 3-24 | 11000 | 3.6 | 48.0 | 1200 |
| 21 | 1-1 | 3-26 | 11000 | 3.5 | 49.4 | 1200 |
| 22 | 1-1 | 3-33 | 10500 | 3.4 | 48.5 | 1200 |
| 23 | 1-1 | 3-45 | 11000 | 3.8 | 45.5 | 1100 |
| 24 | 1-1 | 4-3 | 11000 | 4.5 | 38.4 | 1200 |
| 25 | 1-1 | 4-22 | 11000 | 4.5 | 38.4 | 1200 |
| 26 | 1-1 | 5-3 | 11000 | 4.4 | 39.3 | 1200 |
| 27 | 1-1 | 5-19 | 11000 | 4.5 | 38.4 | 1200 |
| 28 | 1-93 | 2-4 | 11550 | 4.2 | 43.2 | 1200 |
| 29 | 1-93 | 2-5 | 10500 | 4.0 | 41.3 | 1400 |
| 30 | 1-93 | 2-6 | 10500 | 4.0 | 41.3 | 1400 |
| 31 | 1-93 | 2-9 | 10500 | 4.1 | 40.3 | 1100 |

TABLE 2

| Example | First host compound | Second host compound | Luminance (cd/m2) | Voltage (V) | Power efficiency (lm/W) | LT70 (h) |
|---|---|---|---|---|---|---|
| 32 | 1-93 | 2-10 | 10500 | 4.1 | 40.3 | 1200 |
| 33 | 1-93 | 2-13 | 10500 | 4.1 | 40.3 | 1200 |
| 34 | 1-93 | 2-21 | 11550 | 4.4 | 41.1 | 1100 |
| 35 | 1-93 | 2-22 | 11550 | 4.1 | 44.3 | 1100 |
| 36 | 1-93 | 2-23 | 11550 | 4.1 | 44.3 | 1100 |
| 37 | 1-93 | 2-24 | 11550 | 4.5 | 40.2 | 1100 |
| 38 | 1-93 | 2-27 | 11550 | 4.2 | 43.2 | 1100 |
| 39 | 1-93 | 2-28 | 11550 | 4.2 | 43.2 | 1100 |
| 40 | 1-93 | 3-1 | 10500 | 4.3 | 38.3 | 1100 |
| 41 | 1-93 | 3-5 | 10500 | 4.2 | 39.3 | 1100 |
| 42 | 1-93 | 3-8 | 10500 | 4.2 | 39.3 | 1100 |
| 43 | 1-93 | 3-12 | 10500 | 4.1 | 40.3 | 1100 |
| 44 | 1-93 | 3-16 | 10500 | 4.1 | 40.3 | 1100 |
| 45 | 1-93 | 3-24 | 11500 | 3.8 | 47.8 | 1300 |
| 46 | 1-93 | 3-26 | 11500 | 3.7 | 49.2 | 1300 |
| 47 | 1-93 | 3-33 | 11000 | 3.6 | 48.4 | 1300 |
| 48 | 1-93 | 3-45 | 11500 | 4.0 | 45.3 | 1200 |
| 49 | 1-93 | 4-3 | 11500 | 4.7 | 38.2 | 1300 |
| 50 | 1-93 | 4-22 | 11500 | 4.7 | 38.2 | 1300 |
| 51 | 1-93 | 5-3 | 11500 | 4.6 | 39.1 | 1300 |
| 52 | 1-93 | 5-19 | 11500 | 4.7 | 38.2 | 1300 |
| 53 | 1-34 | 2-5 | 10000 | 3.8 | 41.3 | 1200 |
| 54 | 1-34 | 2-6 | 10000 | 3.8 | 41.3 | 1200 |
| 55 | 1-34 | 3-24 | 11000 | 3.4 | 50.8 | 1200 |
| 56 | 1-34 | 3-33 | 10500 | 3.4 | 48.5 | 1200 |
| 57 | 1-34 | 3-45 | 11000 | 3.6 | 48.0 | 1200 |
| 58 | 1-34 | 4-3 | 11000 | 4.3 | 40.2 | 1200 |
| 59 | 1-34 | 4-22 | 11000 | 4.3 | 40.2 | 1200 |
| 60 | 1-34 | 5-3 | 11000 | 4.2 | 41.1 | 1200 |
| 61 | 1-34 | 5-19 | 11000 | 4.3 | 40.2 | 1200 |

TABLE 3

| Example | First host compound | Second host compound | Luminance (cd/m2) | Voltage (V) | Power efficiency (lm/W) | LT70 (h) |
|---|---|---|---|---|---|---|
| 62 | 1-85 | 2-5 | 10000 | 4.0 | 39.3 | 1200 |
| 63 | 1-85 | 2-6 | 10000 | 4.0 | 39.3 | 1200 |
| 64 | 1-85 | 3-24 | 11000 | 3.6 | 48.0 | 1100 |
| 65 | 1-85 | 3-33 | 10500 | 3.4 | 48.5 | 1100 |
| 66 | 1-85 | 3-45 | 11000 | 3.8 | 45.5 | 1100 |
| 67 | 1-85 | 4-3 | 11000 | 4.5 | 38.4 | 1100 |
| 68 | 1-85 | 4-22 | 11000 | 4.5 | 38.4 | 1100 |
| 69 | 1-85 | 5-3 | 11000 | 4.4 | 39.3 | 1100 |
| 70 | 1-85 | 5-19 | 11000 | 4.5 | 38.4 | 1100 |
| 71 | 1-94 | 2-5 | 10000 | 4.0 | 39.3 | 1500 |
| 72 | 1-94 | 2-6 | 10000 | 4.0 | 39.3 | 1500 |
| 73 | 1-94 | 3-24 | 11000 | 3.6 | 48.0 | 1300 |
| 74 | 1-94 | 3-33 | 10500 | 3.4 | 48.5 | 1300 |
| 75 | 1-94 | 3-45 | 11000 | 3.8 | 45.5 | 1200 |
| 76 | 1-94 | 4-3 | 11000 | 4.5 | 38.4 | 1300 |
| 77 | 1-94 | 4-22 | 11000 | 4.5 | 38.4 | 1300 |
| 78 | 1-94 | 5-3 | 11000 | 4.4 | 39.3 | 1300 |
| 79 | 1-94 | 5-19 | 11000 | 4.5 | 38.4 | 1300 |
| 80 | 1-102 | 2-5 | 10000 | 4.0 | 39.3 | 1500 |
| 81 | 1-102 | 2-6 | 10000 | 4.0 | 39.3 | 1500 |
| 82 | 1-102 | 3-24 | 11000 | 3.6 | 48.0 | 1300 |
| 83 | 1-102 | 3-33 | 10500 | 3.4 | 48.5 | 1300 |
| 84 | 1-102 | 3-45 | 11000 | 3.8 | 45.5 | 1200 |
| 85 | 1-102 | 4-3 | 11000 | 4.5 | 38.4 | 1300 |
| 86 | 1-102 | 4-22 | 11000 | 4.5 | 38.4 | 1300 |
| 87 | 1-102 | 5-3 | 11000 | 4.4 | 39.3 | 1300 |
| 88 | 1-102 | 5-19 | 11000 | 4.5 | 38.4 | 1300 |
| 89 | 1-1 | 2-6 | 10000 | 3.8 | 41.3 | 1300 |
| 90 | 1-1 | 3-24 | 11000 | 3.6 | 48.0 | 1200 |
| 91 | 1-1 | 4-22 | 11000 | 4.5 | 38.4 | 1200 |

TABLE 4

| Example | First host compound | Second host compound | Luminance (cd/m2) | Voltage (V) | Power efficiency (lm/W) | LT70 (h) |
|---|---|---|---|---|---|---|
| 92 | 1-1 | 5-19 | 11000 | 4.5 | 38.4 | 1200 |
| 93 | 1-102 | 2-6 | 10000 | 4.0 | 39.3 | 1500 |
| 94 | 1-102 | 3-24 | 11000 | 3.6 | 48.0 | 1300 |
| 95 | 1-102 | 4-22 | 11000 | 4.5 | 38.4 | 1300 |
| 96 | 1-102 | 5-19 | 11000 | 4.5 | 38.4 | 1300 |

Comparative Example 1

An organic electroluminescent device was produced in the same manner as in Example 1 except that compound 1-1 was used alone as the host instead of the hosts of Example 1. The thickness of the light-emitting layer and the concentration of the light-emitting dopant were the same as those in Example 1.

Comparative Examples 2 to 15

Organic electroluminescent devices were produced in the same manner as Comparative Example 1 except that each of compounds shown in Table 5 was used alone instead of the host of Comparative Example 1.

Comparative Examples 16 to 24

Organic electroluminescent devices were produced in the same manner as Example 1 except that compound A was used as the first host and compound 2-5, 2-6, 3-24, 3-33, 3-45, 4-3, 4-22, 5-3 or 5-19 was used as the second host instead of those of Example 1.

Comparative Example 25 to 33

Organic electroluminescent devices were produced in the same manner as in Comparative Examples 16 to 24 except that compound B was used as the first host instead of those of Comparative Examples 16 to 24.

Comparative Example 34 to 42

Organic electroluminescent devices were produced in the same manner as in Comparative Examples 16 to 24 except that compound C was used as the first host instead of those of Comparative Example 16 to 24.

Evaluation results of the produced organic electroluminescent devices are shown in Tables 5 to 6.

TABLE 5

| Comparative Example | First host compound | Second host compound | Luminance (cd/m2) | Voltage (V) | Power efficiency (lm/W) | LT70 (h) |
|---|---|---|---|---|---|---|
| 1 | 1-1 | — | 6000 | 3.4 | 27.7 | 500 |
| 2 | 1-34 | — | 6000 | 3.2 | 29.5 | 500 |
| 3 | 1-85 | — | 6500 | 3.5 | 29.2 | 500 |
| 4 | 1-93 | — | 6500 | 3.6 | 28.4 | 550 |
| 5 | 1-102 | — | 6500 | 3.6 | 28.4 | 550 |
| 6 | — | 2-4 | 9000 | 4.8 | 29.5 | 500 |
| 7 | — | 2-5 | 9000 | 4.8 | 29.5 | 550 |
| 8 | — | 2-6 | 8000 | 4.9 | 25.6 | 500 |
| 9 | — | 3-24 | 6500 | 4.1 | 24.9 | 500 |
| 10 | — | 3-33 | 6500 | 4.0 | 25.5 | 500 |
| 11 | — | 3-45 | 6500 | 4.2 | 24.3 | 400 |
| 12 | — | 4-3 | 8000 | 4.5 | 27.9 | 450 |
| 13 | — | 4-22 | 8000 | 4.4 | 28.6 | 450 |
| 14 | — | 5-3 | 8000 | 4.3 | 29.2 | 450 |
| 15 | — | 5-19 | 8000 | 4.2 | 29.9 | 500 |
| 16 | A | 2-5 | 10000 | 4.5 | 34.9 | 750 |
| 17 | A | 2-6 | 10000 | 4.5 | 34.9 | 750 |
| 18 | A | 3-24 | 10000 | 4.4 | 35.7 | 700 |
| 19 | A | 3-33 | 10000 | 4.4 | 35.7 | 700 |
| 20 | A | 3-45 | 10000 | 4.4 | 35.7 | 700 |
| 21 | A | 4-3 | 10000 | 4.5 | 34.9 | 650 |
| 22 | A | 4-22 | 10000 | 4.5 | 34.9 | 650 |
| 23 | A | 5-3 | 10000 | 4.5 | 34.9 | 650 |
| 24 | A | 5-19 | 10000 | 4.5 | 34.9 | 700 |
| 25 | B | 2-5 | 10500 | 4.4 | 37.5 | 700 |
| 26 | B | 2-6 | 10500 | 4.4 | 37.5 | 750 |
| 27 | B | 3-24 | 10000 | 4.3 | 36.5 | 650 |
| 28 | B | 3-33 | 10000 | 4.3 | 36.5 | 650 |
| 29 | B | 3-45 | 10000 | 4.3 | 36.5 | 650 |
| 30 | B | 4-3 | 10000 | 4.4 | 35.7 | 650 |

TABLE 6

| Comparative Example | First host compound | Second host compound | Luminance (cd/m2) | Voltage (V) | Power efficiency (lm/W) | LT70 (h) |
|---|---|---|---|---|---|---|
| 31 | B | 4-22 | 10000 | 4.4 | 35.7 | 650 |
| 32 | B | 5-3 | 10000 | 4.4 | 35.7 | 650 |
| 33 | B | 5-19 | 10000 | 4.4 | 35.7 | 650 |
| 34 | C | 2-5 | 10000 | 4.4 | 35.7 | 750 |
| 35 | C | 2-6 | 10000 | 4.4 | 35.7 | 750 |
| 36 | C | 3-24 | 10000 | 4.4 | 35.7 | 650 |
| 37 | C | 3-33 | 10000 | 4.3 | 36.5 | 650 |
| 38 | C | 3-45 | 10000 | 4.4 | 35.7 | 650 |
| 39 | C | 4-3 | 10000 | 4.4 | 35.7 | 650 |
| 40 | C | 4-22 | 10000 | 4.5 | 34.9 | 650 |
| 41 | C | 5-3 | 10000 | 4.5 | 34.9 | 650 |
| 42 | C | 5-19 | 10000 | 4.5 | 34.9 | 700 |

From Tables 1 to 4, it is understood that Examples 1 to 96 improved the power efficiency and the lifetime characteristics, and exhibited good characteristics.

Example 97

On a glass substrate on which an anode made of ITO with a film thickness of 110 nm was formed, respective thin films were laminated by a vacuum evaporation method at a degree of vacuum of $4.0\times10^{-5}$ Pa. First, HAT-CN was formed with a thickness of 25 nm as a hole injection layer on ITO, and next, NPD was formed with a thickness of 45 nm as a hole transport layer. Next, HT-1 was formed with a thickness of 10 nm as an electron blocking layer. Then, compound 1-1 as a first host, compound 2-4 as a second host and $Ir(piq)_2acac$ as a light-emitting dopant were co-vapor-deposited from different vapor deposition sources, respectively, to form a light-emitting layer with a thickness of 40 nm. In this case, co-vapor deposition was performed under a vapor deposition condition such that the concentration of $Ir(piq)_2acac$ was 6.0 wt %. Next, ET-1 was formed with a thickness of 37.5 nm as an electron transport layer. Then, LiF was formed with a thickness of 1 nm as an electron injection layer on the electron transport layer. Finally, Al was formed with a thickness of 70 nm as a cathode on the electron injection layer to produce an organic electroluminescent device.

Examples 98 to 182

Organic electroluminescent devices were produced in the same manner as in Example 97 except that compounds shown in Tables 7 to 9 were used as the first host and the second host instead of those of Example 97.

Evaluation results of the produced organic electroluminescent devices are shown in Tables 7 to 9. LT95 used therein is a time period needed for the initial luminance to be reduced to 95% thereof, and it represents lifetime characteristics.

TABLE 7

| Example | First host compound | Second host compound | Luminance (cd/m2) | Voltage (V) | Power efficiency (lm/W) | LT95 (h) |
|---|---|---|---|---|---|---|
| 97 | 1-1 | 2-4 | 5500 | 4.0 | 21.6 | 200 |
| 98 | 1-1 | 2-5 | 5000 | 3.8 | 20.7 | 250 |
| 99 | 1-1 | 2-6 | 5000 | 3.8 | 20.7 | 250 |
| 100 | 1-1 | 2-9 | 5000 | 3.9 | 20.1 | 200 |
| 101 | 1-1 | 2-10 | 5000 | 3.9 | 20.1 | 200 |
| 102 | 1-1 | 2-13 | 5000 | 3.9 | 20.1 | 200 |
| 103 | 1-1 | 2-21 | 5500 | 4.2 | 20.6 | 200 |
| 104 | 1-1 | 2-22 | 5500 | 3.9 | 22.2 | 200 |
| 105 | 1-1 | 2-23 | 5500 | 3.9 | 22.2 | 200 |
| 106 | 1-1 | 2-24 | 5500 | 4.3 | 20.1 | 200 |
| 107 | 1-1 | 2-27 | 5500 | 4 | 21.6 | 200 |
| 108 | 1-1 | 2-28 | 5500 | 4 | 21.6 | 200 |
| 109 | 1-1 | 3-1 | 5000 | 4.1 | 19.2 | 200 |
| 110 | 1-1 | 3-5 | 5000 | 4 | 19.6 | 200 |
| 111 | 1-1 | 3-8 | 5000 | 4 | 19.6 | 200 |
| 112 | 1-1 | 3-12 | 5000 | 3.9 | 20.1 | 200 |
| 113 | 1-1 | 3-16 | 5000 | 3.9 | 20.1 | 200 |
| 114 | 1-1 | 3-24 | 5500 | 3.6 | 24.0 | 250 |
| 115 | 1-1 | 3-26 | 5500 | 3.5 | 24.7 | 250 |
| 116 | 1-1 | 3-33 | 5000 | 3.4 | 23.1 | 250 |
| 117 | 1-1 | 3-45 | 5500 | 3.8 | 22.7 | 200 |
| 118 | 1-1 | 4-3 | 5500 | 4.5 | 19.2 | 250 |
| 119 | 1-1 | 4-22 | 5500 | 4.5 | 19.2 | 250 |
| 120 | 1-1 | 5-3 | 5500 | 4.4 | 19.6 | 250 |
| 121 | 1-1 | 5-19 | 5500 | 4.5 | 19.2 | 250 |
| 122 | 1-93 | 2-4 | 5500 | 4.2 | 20.6 | 250 |
| 123 | 1-93 | 2-5 | 5000 | 4.0 | 19.7 | 300 |
| 124 | 1-93 | 2-6 | 5000 | 4.0 | 19.7 | 300 |
| 125 | 1-93 | 2-9 | 5000 | 4.1 | 19.2 | 200 |
| 126 | 1-93 | 2-10 | 5000 | 4.1 | 19.2 | 250 |

TABLE 8

| Example | First host compound | Second host compound | Luminance (cd/m2) | Voltage (V) | Power efficiency (lm/W) | LT95 (h) |
|---|---|---|---|---|---|---|
| 127 | 1-93 | 2-13 | 5000 | 4.1 | 19.2 | 250 |
| 128 | 1-93 | 2-21 | 5500 | 4.4 | 19.6 | 200 |
| 129 | 1-93 | 2-22 | 5500 | 4.1 | 21.1 | 200 |
| 130 | 1-93 | 2-23 | 5500 | 4.1 | 21.1 | 200 |
| 131 | 1-93 | 2-24 | 5500 | 4.5 | 19.1 | 200 |
| 132 | 1-93 | 2-27 | 5500 | 4.2 | 20.6 | 200 |
| 133 | 1-93 | 2-28 | 5500 | 4.2 | 20.6 | 200 |
| 134 | 1-93 | 3-1 | 5000 | 4.3 | 18.2 | 200 |
| 135 | 1-93 | 3-5 | 5000 | 4.2 | 18.7 | 200 |
| 136 | 1-93 | 3-8 | 5000 | 4.2 | 18.7 | 200 |
| 137 | 1-93 | 3-12 | 5000 | 4.1 | 19.2 | 200 |
| 138 | 1-93 | 3-16 | 5000 | 4.1 | 19.2 | 200 |
| 139 | 1-93 | 3-24 | 5500 | 3.8 | 22.9 | 250 |
| 140 | 1-93 | 3-26 | 5500 | 3.7 | 23.5 | 250 |
| 141 | 1-93 | 3-33 | 5000 | 3.6 | 22.0 | 250 |
| 142 | 1-93 | 3-45 | 5500 | 4.0 | 21.7 | 250 |
| 143 | 1-93 | 4-3 | 5500 | 4.7 | 18.3 | 250 |
| 144 | 1-93 | 4-22 | 5500 | 4.7 | 18.3 | 250 |
| 145 | 1-93 | 5-3 | 5500 | 4.6 | 18.7 | 250 |
| 146 | 1-93 | 5-19 | 5500 | 4.7 | 18.3 | 250 |
| 147 | 1-34 | 2-5 | 5000 | 3.8 | 20.7 | 250 |
| 148 | 1-34 | 2-6 | 5000 | 3.8 | 20.7 | 250 |
| 149 | 1-34 | 3-24 | 5500 | 3.4 | 25.4 | 250 |
| 150 | 1-34 | 3-33 | 5000 | 3.4 | 23.1 | 250 |
| 151 | 1-34 | 3-45 | 5500 | 3.6 | 24.0 | 250 |
| 152 | 1-34 | 4-3 | 5500 | 4.3 | 20.1 | 250 |
| 153 | 1-34 | 4-22 | 5500 | 4.3 | 20.1 | 250 |
| 154 | 1-34 | 5-3 | 5500 | 4.2 | 20.6 | 250 |
| 155 | 1-34 | 5-19 | 5500 | 4.3 | 20.1 | 250 |
| 156 | 1-85 | 2-5 | 5000 | 4.0 | 19.6 | 250 |

TABLE 9

| Example | First host compound | Second host compound | Luminance (cd/m2) | Voltage (V) | Power efficiency (lm/W) | LT95 (h) |
|---|---|---|---|---|---|---|
| 157 | 1-85 | 2-6 | 5000 | 4.0 | 19.6 | 250 |
| 158 | 1-85 | 3-24 | 5500 | 3.6 | 24.0 | 200 |
| 159 | 1-85 | 3-33 | 5000 | 3.4 | 23.1 | 200 |
| 160 | 1-85 | 3-45 | 5500 | 3.8 | 22.7 | 200 |
| 161 | 1-85 | 4-3 | 5500 | 4.5 | 19.2 | 200 |
| 162 | 1-85 | 4-22 | 5500 | 4.5 | 19.2 | 200 |
| 163 | 1-85 | 5-3 | 5500 | 4.4 | 19.6 | 200 |
| 164 | 1-85 | 5-19 | 5500 | 4.5 | 19.2 | 200 |
| 165 | 1-94 | 2-5 | 5000 | 4.0 | 19.6 | 300 |
| 166 | 1-94 | 2-6 | 5000 | 4.0 | 19.6 | 300 |
| 167 | 1-94 | 3-24 | 5500 | 3.6 | 24.0 | 250 |
| 168 | 1-94 | 3-33 | 5000 | 3.4 | 23.1 | 250 |
| 169 | 1-94 | 3-45 | 5500 | 3.8 | 22.7 | 250 |
| 170 | 1-94 | 4-3 | 5500 | 4.5 | 19.2 | 250 |
| 171 | 1-94 | 4-22 | 5500 | 4.5 | 19.2 | 250 |
| 172 | 1-94 | 5-3 | 5500 | 4.4 | 19.6 | 250 |
| 173 | 1-94 | 5-19 | 5500 | 4.5 | 19.2 | 250 |
| 174 | 1-102 | 2-5 | 5000 | 4.0 | 19.6 | 300 |
| 175 | 1-102 | 2-6 | 5000 | 4.0 | 19.6 | 300 |
| 176 | 1-102 | 3-24 | 5500 | 3.6 | 24.0 | 250 |
| 177 | 1-102 | 3-33 | 5000 | 3.4 | 23.1 | 250 |
| 178 | 1-102 | 3-45 | 5500 | 3.8 | 22.7 | 250 |
| 179 | 1-102 | 4-3 | 5500 | 4.5 | 19.2 | 250 |
| 180 | 1-102 | 4-22 | 5500 | 4.5 | 19.2 | 250 |
| 181 | 1-102 | 5-3 | 5500 | 4.4 | 19.6 | 250 |
| 182 | 1-102 | 5-19 | 5500 | 4.5 | 19.2 | 250 |

Comparative Example 43

Organic electroluminescent devices were produced in the same manner as in Example 97 except that compound 1-1 was used alone as the host instead of the hosts of Example 97. The thickness of the light-emitting layer and the concentration of the light-emitting dopant were the same as those in Example 97.

Comparative Example 44 to 57

Organic electroluminescent devices were produced in the same manner as in Comparative Example 43 except that each of compounds shown in Table 10 was used alone instead of the host of Comparative Example 43.

Comparative Example 58 to 66

Organic electroluminescent devices were produced in the same manner as in Example 97 except that compound A was used as the first host, and compound 2-5, compound 2-6, compound 3-24, compound 3-33, compound 3-45, compound 4-3, compound 4-22, compound 5-3 or compound 5-19 was used as the second host instead of those of Example 97.

Comparative Examples 67 to 75

Organic electroluminescent devices were produced in the same manner as in Comparative Examples 58 to 66 except that compound B was used as the first host instead of that of Comparative Examples 58 to 66.

Comparative Examples 76 to 84

Organic electroluminescent devices were produced in the same manner as in Comparative Examples 58 to 66 except that compound C was used as the first host instead of that of Comparative Examples 58 to 66.

Evaluation results of the produced organic electroluminescent devices are shown in in Tables 10 to 11.

Table 10

| Comparative Example | First host compound | Second host compound | Luminance (cd/m2) | Voltage (V) | Power efficiency (lm/W) | LT95 (h) |
|---|---|---|---|---|---|---|
| 43 | 1-1 | — | 3000 | 3.4 | 13.9 | 100 |
| 44 | 1-34 | — | 2500 | 3.2 | 12.3 | 100 |
| 45 | 1-85 | — | 3000 | 3.5 | 13.5 | 100 |
| 46 | 1-93 | — | 3000 | 3.6 | 13.1 | 100 |
| 47 | 1-102 | — | 3000 | 3.7 | 12.7 | 110 |
| 48 | — | 2-4 | 3500 | 4.8 | 11.5 | 90 |
| 49 | — | 2-5 | 3500 | 4.8 | 11.5 | 110 |
| 50 | — | 2-6 | 3500 | 4.9 | 11.2 | 110 |
| 51 | — | 3-24 | 3500 | 4.1 | 13.4 | 100 |
| 52 | — | 3-33 | 3500 | 4.0 | 13.7 | 100 |
| 53 | — | 3-45 | 3000 | 4.2 | 11.2 | 90 |
| 54 | — | 4-3 | 3500 | 4.5 | 12.2 | 100 |
| 55 | — | 4-22 | 3500 | 4.4 | 12.5 | 100 |
| 56 | — | 5-3 | 3500 | 4.3 | 12.8 | 100 |
| 57 | — | 5-19 | 3500 | 4.2 | 13.1 | 100 |
| 58 | A | 2-5 | 4000 | 4.4 | 14.3 | 150 |
| 59 | A | 2-6 | 4000 | 4.4 | 14.3 | 150 |
| 60 | A | 3-24 | 4000 | 4.4 | 14.3 | 150 |
| 61 | A | 3-33 | 4000 | 4.4 | 14.3 | 150 |
| 62 | A | 3-45 | 4000 | 4.4 | 14.3 | 120 |
| 63 | A | 4-3 | 4000 | 4.6 | 13.7 | 150 |
| 64 | A | 4-22 | 4000 | 4.6 | 13.7 | 150 |
| 65 | A | 5-3 | 4000 | 4.6 | 13.7 | 130 |
| 66 | A | 5-19 | 4000 | 4.5 | 14.0 | 130 |
| 67 | B | 2-5 | 4000 | 4.6 | 13.7 | 150 |
| 68 | B | 2-6 | 4000 | 4.6 | 13.7 | 150 |
| 69 | B | 3-24 | 4000 | 4.3 | 14.6 | 150 |
| 70 | B | 3-33 | 4000 | 4.2 | 15.0 | 150 |

Table 10-continued

| Comparative Example | First host compound | Second host compound | Luminance (cd/m2) | Voltage (V) | Power efficiency (lm/W) | LT95 (h) |
|---|---|---|---|---|---|---|
| 71 | B | 3-45 | 4000 | 4.5 | 14.0 | 120 |
| 72 | B | 4-3 | 4000 | 4.6 | 13.7 | 150 |

TABLE 11

| Comparative Example | First host compound | Second host compound | Luminance (cd/m2) | Voltage (V) | Power efficiency (lm/W) | LT95 (h) |
|---|---|---|---|---|---|---|
| 73 | B | 4-22 | 4000 | 4.5 | 14.0 | 150 |
| 74 | B | 5-3 | 4000 | 4.4 | 14.3 | 150 |
| 75 | B | 5-19 | 4000 | 4.4 | 14.3 | 150 |
| 76 | C | 2-5 | 4000 | 4.5 | 14.0 | 150 |
| 77 | C | 2-6 | 4000 | 4.6 | 13.7 | 150 |
| 78 | C | 3-24 | 4000 | 4.4 | 14.3 | 150 |
| 79 | C | 3-33 | 4000 | 4.3 | 14.6 | 150 |
| 80 | C | 3-45 | 4000 | 4.7 | 13.4 | 120 |
| 81 | C | 4-3 | 4000 | 4.6 | 13.7 | 150 |
| 82 | C | 4-22 | 4000 | 4.5 | 14.0 | 150 |
| 83 | C | 5-3 | 4000 | 4.5 | 14.0 | 130 |
| 84 | C | 5-19 | 4000 | 4.5 | 14.0 | 130 |

From Tables 7 to 9, it is understood that Examples 97 to 182 improved the power efficiency and the lifetime characteristics, and exhibited good characteristics.

Compounds used in Examples are shown below.

[C34]

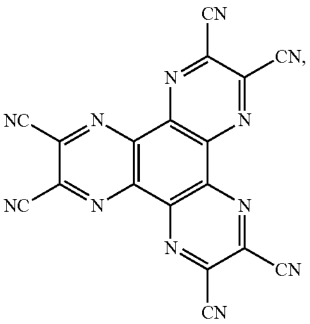

HAT-CN

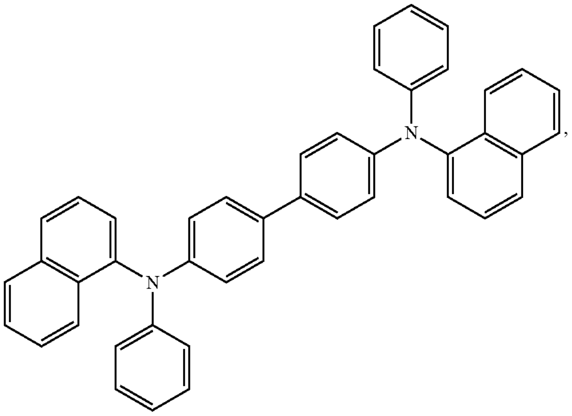

NPD

-continued

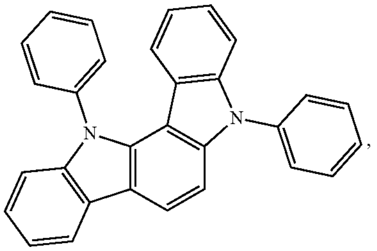

HT-1

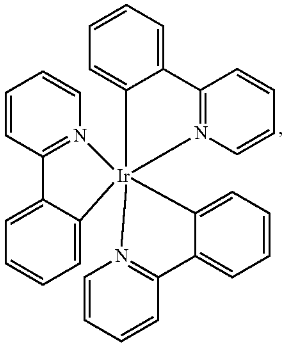

Ir(ppy)3

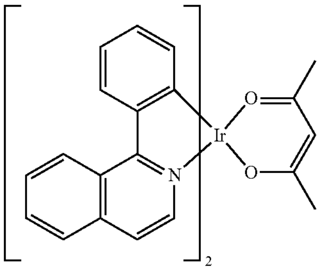

Ir(piq)2acac

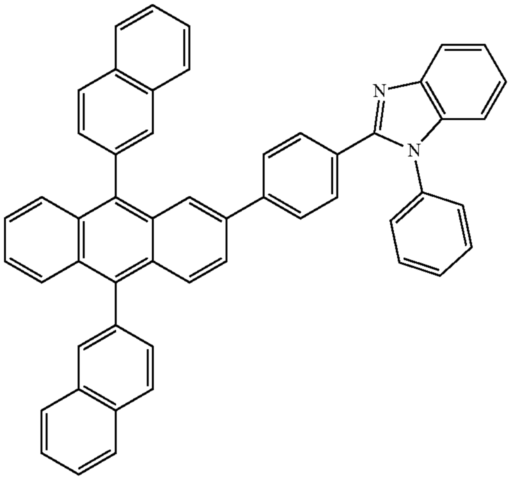

ET-1

A

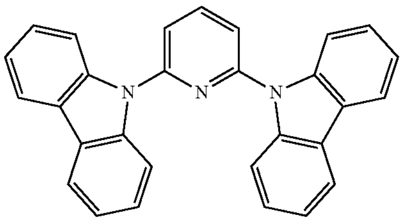

-continued

B

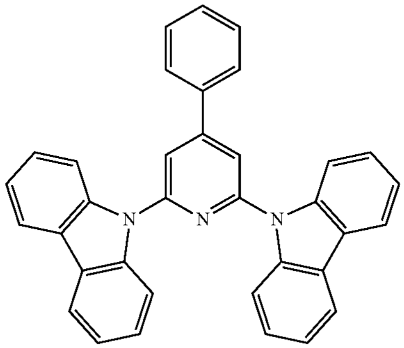

C

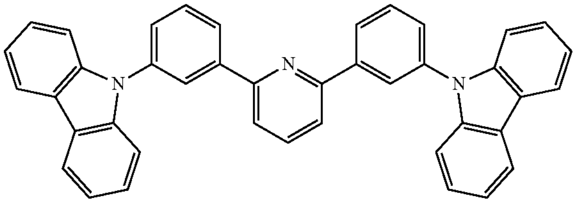

INDUSTRIAL APPLICABILITY

The organic electroluminescent device of the present invention is operable at a low voltage and is able to achieve high efficiency and extended life.

The invention claimed is:

1. An organic electroluminescent device comprising one or more light-emitting layers between an anode and a cathode opposed to each other, wherein at least one of the light-emitting layers is a light-emitting layer comprising a vapor deposition layer containing a mixture of a first host, a second host and a light-emitting dopant material, the first host is selected from a compound represented by the following general formula (1), and the second host is selected from a compound represented by the following general formula (2) or general formula (4):

(1)

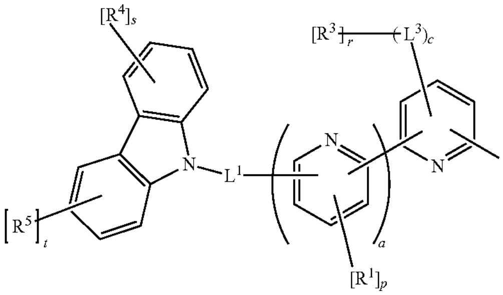

-continued

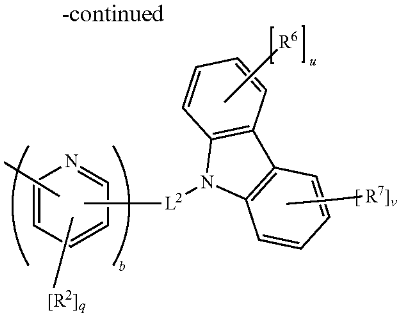

wherein $L^1$ to $L^3$ each represent a single bond, a substituted or unsubstituted aromatic hydrocarbon group having 6 to 30 carbon atoms, or a linked aromatic group in which 2 to 10 thereof are linked to each other, $R^1$ to $R^7$ independently represent hydrogen, deuterium, an aliphatic hydrocarbon group having 1 to 10 carbon atoms, a substituted or unsubstituted aromatic hydrocarbon group having 6 to 10 carbon atoms, or a substituted or unsubstituted aromatic heterocyclic group having 3 to 12 carbon atoms; a, b and c represent the number of repetitions and each independently represent an integer of 0 to 3, wherein a+b≥1; and p, q, r, s, t, u and v represent the number of substitutions and each independently represent an integer of 1 to 3;

(2)

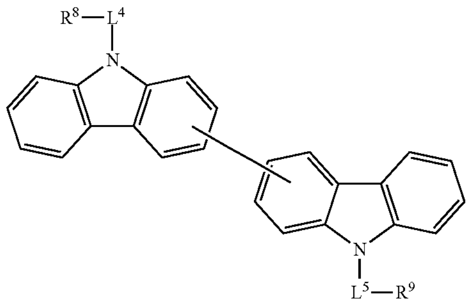

wherein $R^8$ and $R^9$ independently represent hydrogen, an aromatic hydrocarbon group having 6 to 14 carbon atoms, or a group in which two of the aromatic hydrocarbon groups are linked to each other; and $L^4$ and $L^5$ independently represent a phenylene group;

(4)

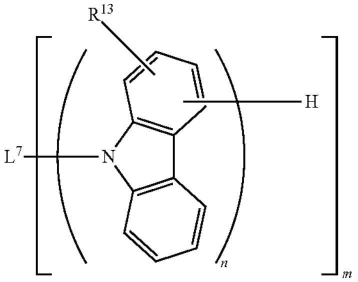

wherein $L^7$ is an m-valent aromatic hydrocarbon group having 6 to 30 carbon atoms, an aromatic heterocyclic group having 3 to 16 carbon atoms, or a linked aromatic group in which 2 to 10 of the aromatic rings are linked to each other, provided that $L^7$ is not a group containing a carbazole ring; $R^{13}$ is each independently hydrogen, an alkyl group having 1 to 10 carbon atoms, or a cycloalkyl group having 3 to 11 carbon atoms; m is the number of substitutions and represents an integer of 1 to 3; and n is the number of repetitions and is each independently an integer of 1 to 4, provided that at least one n is an integer of 2 to 4.

2. The organic electroluminescent device according to claim 1, wherein the compound represented by the general formula (2) is a compound represented by the following formula (6):

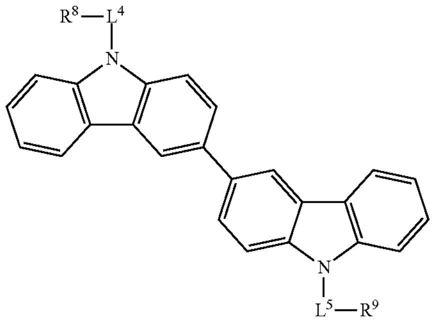

(6)

wherein $R^8$, $R^9$, $L^4$ and $L^5$ are as defined for the general formula (2).

3. The organic electroluminescent device according to claim 1, wherein the general formula (4) has at least one binding structure represented by formula (c1) or (c2),

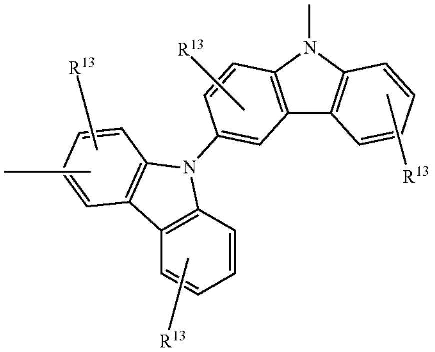

(c1)

wherein $R^{13}$ is as defined for the general formula (4),

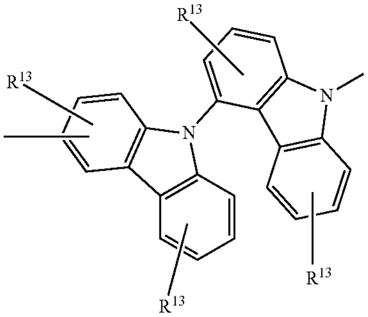

(c2)

wherein $R^{13}$ is as defined for the general formula (4).

4. The organic electroluminescent device according to claim 1, wherein the compound represented by the general formula (1) is a compound represented by any one of formulas (9) to (11):

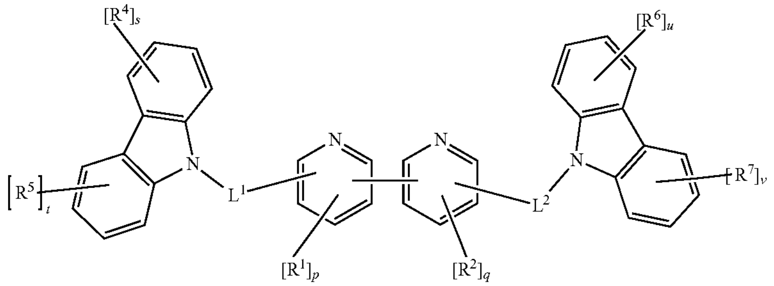

(9)

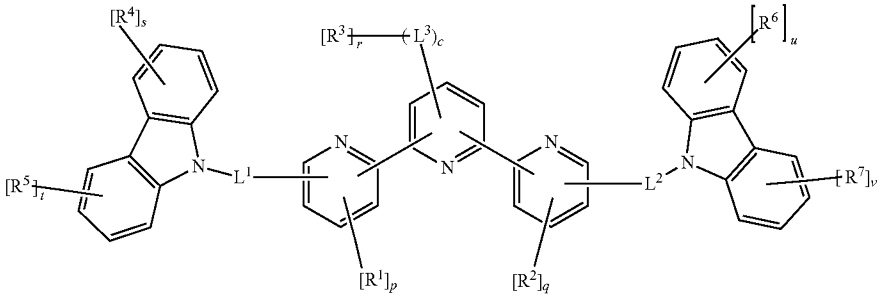

(10)

-continued (11)

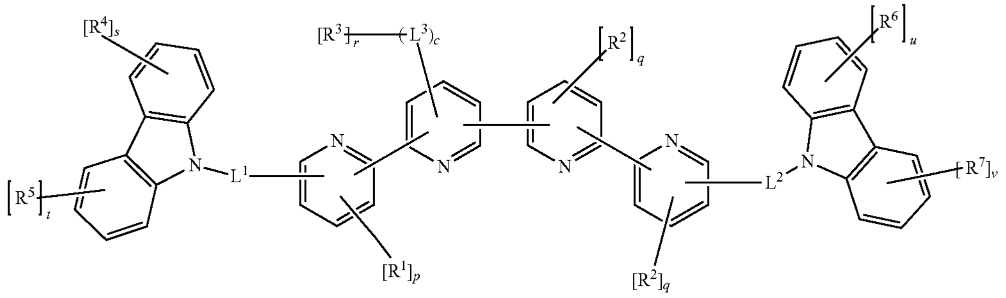

wherein $L^1$ to $L^3$, $R^1$ to $R^7$ and c and p to v are as defined for the general formula (1).

5. The organic electroluminescent device according to claim 1, wherein a proportion of the first host is larger than 20 wt % and less than 55 wt % based on the first host and the second host in total.

6. The organic electroluminescent device according to claim 1, wherein the light-emitting dopant material is an organic metal complex containing at least one metal selected from the group consisting of ruthenium, rhodium, palladium, silver, rhenium, osmium, iridium, platinum and gold.

7. The organic electroluminescent device according to claim 1, wherein the light-emitting dopant material is a thermally activated delayed fluorescence-emitting dopant material.

8. The organic electroluminescent device according to claim 1, wherein a hole blocking layer is provided adjacent to the light-emitting layer, and the compound represented by the general formula (1) is contained in the hole blocking layer.

9. A method for producing the organic electroluminescent device according to claim 1, comprising a step of mixing a first host and a second host to prepare a premixture, and then vapor-depositing a host material containing the premixture to form a light-emitting layer.

10. The method for producing the organic electroluminescent device according to claim 9, wherein a difference in 50% weight reduction temperatures of the first host and the second host is within 20° C.

* * * * *